United States Patent
Park et al.

(10) Patent No.: US 11,925,691 B2
(45) Date of Patent: Mar. 12, 2024

(54) NON-PEPTIDIC POLYMERIC LINKER COMPOUND, CONJUGATE COMPRISING SAME LINKER COMPOUND, AND METHODS FOR PREPARING SAME LINKER COMPOUND AND CONJUGATE

(71) Applicant: HANMI PHARM. CO., LTD., Hwaseong-si (KR)

(72) Inventors: Su Yeon Park, Hwaseong-si (KR); Dae Jin Kim, Hwaseong-si (KR); Sung Youb Jung, Hwaseong-si (KR); Yong Gyu Jung, Hwaseong-si (KR); Hyun Sik Yun, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 1253 days.

(21) Appl. No.: 16/484,290

(22) PCT Filed: Feb. 7, 2018

(86) PCT No.: PCT/KR2018/001660
§ 371 (c)(1),
(2) Date: Oct. 22, 2019

(87) PCT Pub. No.: WO2018/147641
PCT Pub. Date: Aug. 16, 2018

(65) Prior Publication Data
US 2023/0139745 A1    May 4, 2023

(30) Foreign Application Priority Data
Feb. 7, 2017  (KR) .................. 10-2017-0016916

(51) Int. Cl.
A61K 47/68   (2017.01)
A61K 47/54   (2017.01)
(Continued)

(52) U.S. Cl.
CPC ........ *A61K 47/6889* (2017.08); *A61K 47/545* (2017.08); *A61K 47/60* (2017.08); *A61K 47/6803* (2017.08); *C07D 225/08* (2013.01)

(58) Field of Classification Search
None
See application file for complete search history.

(56) References Cited

U.S. PATENT DOCUMENTS 10,435,509 B2   10/2019  Kinbara et al.
2016/0194359 A1  7/2016  Francois et al.
(Continued)

FOREIGN PATENT DOCUMENTS

EP    3020418 A1    5/2016
JP    2017-14371 A   1/2017
(Continued)

OTHER PUBLICATIONS

Colombo et al., Angew. Chem. Int. Ed. 2012, 51, 496-499 (Year: 2012).*
(Continued)

*Primary Examiner* — Karl J Puttlitz
(74) *Attorney, Agent, or Firm* — Sughrue Mion, PLLC

(57) ABSTRACT

One aspect of the present invention provides a compound in which a functional group capable of binding to a globulin Fc region or a physiologically active polypeptide is introduced at one end of a non-peptidic polymer and a functional group capable of a click reaction is introduced at the other end; a polypeptide conjugate in which a physiologically active polypeptide binds to one end of the compound; a physiologically active polypeptide conjugate in which a physiologically active polypeptide and an immunoglobulin Fc region bind to both ends thereof by using the compound as (Continued)

a linker; and methods for preparing the same compound, polypeptide conjugate, and physiologically active polypeptide conjugate.

3 Claims, 17 Drawing Sheets

(51) Int. Cl.
*A61K 47/60* (2017.01)
*C07D 225/08* (2006.01)

(56) References Cited

U.S. PATENT DOCUMENTS

| | | | |
|---|---|---|---|
| 2017/0008950 | A1 | 1/2017 | Capon |
| 2017/0304460 | A1 | 10/2017 | Christie et al. |
| 2018/0177850 | A1 | 6/2018 | Jung et al. |
| 2018/0256731 | A1 | 9/2018 | Hwang et al. |

FOREIGN PATENT DOCUMENTS

| | | |
|---|---|---|
| KR | 10-2014-0018462 A | 2/2014 |
| KR | 10-2015-0008012 A | 1/2015 |
| WO | 2015/138907 A2 | 9/2015 |
| WO | 2016/054315 A1 | 4/2016 |

OTHER PUBLICATIONS

Database Caplus Chemical Abstracts Service, Columbus, Ohio, US; Registry No. 1817769-38-2, Nov. 3, 2015 (Year: 2015).*
Broadpharm, "endo-BCN-PEG4-NHS-ester", BP-22851, dated Oct. 10, 2016, Retrieved from the Internet: URL: https://broadpharm.com/web/product.php?catalog=BP-22851 (Year: 2016).*
Miriam Colombo, et al., "Site-Specific Conjugation of ScFvs Antibodies to Nanoparticles by Bioorthogonal Strain-Promoted Alkyne-Nitrone Cycloaddition", Angew. Chem. Int. Ed., 2012, pp. 496-499, vol. 51.
Noor Faizah Che Harun, et al., "Artificial Control of Gene Silencing Activity Based on siRNA Conjugation with Polymeric Molecule Having Coil-Globule Transition Behavior", Bioconjugate Chemistry, 2016, pp. 1961-1964, vol. 27.
Ke Xiong, et al., "Biomimetic Immuno-Magnetosomes for High-Performance Enrichment of Circulating Tumor Cells", Advanced Materials, 2016, pp. 7929-7935, vol. 28.
International Search Report for PCT/KR2018/001660 dated May 8, 2018 [PCT/ISA/210].
Broadpharm, "BCN-PEG", dated Jan. 1, 2017, XP055752677, Retrieved from the Internet: URL:https://broadpharm.com/web/products.php?category1=PEG+Linkers&category2=bcn-peg[retrieved on Nov. 20, 2020] (5 pages total).
Broadpharm, "DBCO PEG", dated Jan. 1, 2017, XP055752678, Retrieved from the Internet: URL:https://broadpharm.com/web/products.php?category1=PEG%20Linkers&category2=dbco-peg [retrieved on Nov. 20, 2020] (14 pages total).
Conju-Probe, "DBCO-PEG3-ALDEHYDE", dated Jan. 1, 2017, XPO55752700, Retrieved from the Internet: URL:https://conju-probe.com/product/dbco-peg3-aldehyde/ [retrieved on Nov. 20, 2020] (2 pages total).
Currier et al., "Targeted Drug Delivery with an Integrin-Binding Knottin-Fc-MMAF Conjugate Produced by Cell-Free Protein Synthesis", Molecular Cancer Therapeutics, vol. 15, No. 6, Jun. 2016, pp. 1291-1300, XP055511613 (11 pages total) (published online first Mar. 29, 2016).
Thomas et al., "Application of Strain-Promoted Azide-Alkyne Cycloaddition and Tetrazine Ligation to Targeted Fc-Drug Conjugates", Bioconjugate Chemistry, vol. 23, No. 10 (Oct. 17, 2012) pp. 2007-2013, XP055286002 (7 pages total).
Dommerholt et al., "Strain-Promoted 1,3-Dipolar Cycloaddition of Cycloalkynes and Organic Azides", Topics in Current Chemistry, vol. 374, No. 16 (Mar. 22, 2016), XP055345310 (20 pages total).
Borrmann, "Expanding and Exploring the Bioconjugation Toolbox", XP055752642, (Feb. 19, 2016), Retrieved from the Internet: URL:https://repository.ubn.ru.nt/bitstream/handle/2066/150993/150993.pdf (90 pages total).
Broadpharm, "endo-BCN-PEG4-NHS-ester", BP-22851, dated Oct. 10, 2016, Retrieved from the Internet: URL: https://broadpharm.com/web/product.php?catalog=BP-22851 (6 pages total).

* cited by examiner

NON-PEPTIDIC POLYMERIC LINKER COMPOUND, CONJUGATE COMPRISING SAME LINKER COMPOUND, AND METHODS FOR PREPARING SAME LINKER COMPOUND AND CONJUGATE

CROSS REFERENCE TO RELATED APPLICATIONS

This application is a National Stage of International Application No. PCT/KR2018/001660 filed Feb. 7, 2018, claiming priority based on Korean Patent Application No. 10-2017-0016916 filed Feb. 7, 2017.

TECHNICAL FIELD

The present disclosure relates to a non-peptidyl polymeric compound, a conjugate including the compound, and a method of preparing the same. More specifically, the present disclosure relates to a non-peptidyl polymeric compound which may be used as a linker to increase half-life of a physiologically active polypeptide, a conjugate linked with the physiologically active polypeptide via the compound as a linker, and a method of preparing the same.

BACKGROUND ART

Protein drugs have short blood half-lives when administered to the human body. Thus, protein drugs are inconvenient in that they are required to be frequently administered in order to maintain their efficacy. To solve this problem, pegylation which binds polyethylene glycol to a protein drug has been used to increase blood half-life of the protein drug. This pegylation not only increases the blood half-life of the protein drug, but also reduces antigenicity of the protein drug, and thus pegylation is widely employed in protein therapeutic agents.

The polyethylene glycol has a form of a polyethylene glycol derivative that further includes a functional group binding to an immunoglobulin Fc region which is known to improve the half-life of the protein drug, in addition to a functional group binding to the protein drug. Therefore, the polyethylene glycol may be used as a linker that links the protein drug and the immunoglobulin Fc region. Further, as the linker compound for the protein drug and the immunoglobulin Fc region, various non-peptidyl polymers having biocompatibility have been proposed as a linker capable of forming a conjugate together with the protein drug, in addition to the polyethylene glycol derivative (Patent Document 1).

The non-peptidyl polymer may have, each independently at both ends thereof, an aldehyde group, a propionaldehyde group, a butyraldehyde group, a maleimide group, a succinimide derivative (succinimidyl propionate, hydroxy succinimidyl, succinimidyl carboxymethyl, or succinimidyl carbonate), etc., as a functional group to bind with the protein drug and immunoglobulin Fc.

However, the functional groups have a disadvantage in that a conjugate production yield is reduced due to the reason that the entire substances introduced into a reaction may not be converted into conjugates during the reaction targeting a specific amino acid site upon binding with protein drugs, and some reactive groups have reduced stability in the blood.

(Patent Document 1) Korean Patent Publication No. 2014-0018462

DESCRIPTION OF EMBODIMENTS

Technical Problem

An aspect of the present disclosure is to provide a non-peptidyl polymeric compound not only capable of stably binding with a physiologically active polypeptide to increase blood half-life of the physiologically active polypeptide but also capable of binding therewith in a high yield.

Another aspect of the present disclosure is to provide a physiologically active polypeptide linkage, in which a physiologically active polypeptide is linked at one end of the non-peptidyl polymeric compound.

Still another aspect of the present disclosure is to provide a physiologically active polypeptide conjugate, in which a physiologically active polypeptide and an immunoglobulin Fc region are linked to both ends of the non-peptidyl polymeric compound, respectively.

Still another aspect of the present disclosure is to provide a method of preparing the non-peptidyl polymeric compound, the physiologically active polypeptide linkage, and the physiologically active polypeptide conjugate.

Solution to Problem

An aspect of the present disclosure is to provide a compound, in which a functional group capable of binding with an immunoglobulin Fc region or a physiologically active polypeptide is introduced at one end of a non-peptidyl polymer and a functional group capable of undergoing a click reaction is introduced at the other end thereof.

The compound may include a compound of the following Formula 1, a stereoisomer thereof, or a pharmaceutically acceptable salt thereof:

$$\text{R1-non-peptidyl polymer-X—R2} \quad \text{[Formula 1]}$$

in Formula 1,

R1 is an aliphatic hydrocarbon group including a functional group selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, and derivatives thereof;

the non-peptidyl polymer is selected from the group consisting of polyethylene glycol, polypropylene glycol, a copolymer of ethylene glycol and propylene glycol, polyoxyethylated polyol, polyvinyl alcohol, polysaccharide, dextran, polyvinyl ethyl ether, polylactic acid (PLA), poly-lactic-glycolic acid (PLGA), lipid polymers, chitins, hyaluronic acid, and polysaccharides;

X is —$(CH_2)_j$NHCO— or —$(CH_2)_j$NHCS—, wherein j is an integer of 0 to 6;

R2 is —$(R3)_k$-$(Z)_l$—$(R4)_m$-$(CZ)_p$—Y—, wherein R3 and R4 are each independently $C_1$-$C_6$ alkylene, $C_6$-$C_{20}$ arylene, or $C_5$-$C_{20}$ heteroarylene having 1 to 3 heteroatoms selected from N, O, and S, Z is O or S, Y is $C_2$-$C_6$ alkynyl, cycloalkynyl, arylcycloalkynyl, diarylcycloalkynyl, heterocycloalkynyl, or diarylheterocycloalkynyl (wherein each cycloalkynyl has 3 to 8 carbon atoms, each aryl has 5 to 8 carbon atoms, and each heterocycloalkynyl is a saturated ring including 3 to 8 atoms and having heteroatoms selected from N, O, and S in 1 to 3 of ring atoms), k, l, m, and p are each independently an integer of 0 to 3, provided that all of them may not be 0 at the same time, and the alkynyl, cycloalkynyl, arylcycloalkynyl, diarylcycloalkynyl, heterocycloalkynyl, or diarylheterocycloalkynyl is substituted or unsubstituted with $C_1$-$C_6$ alkyl, $C_1$-$C_6$ alkoxy, $C_1$-$C_6$ alkoxycarbonyl, oxo, or halogen.

Another aspect of the present disclosure is to provide a method of preparing the compound according to an aspect of the present disclosure, the method including:

introducing a functional group capable of undergoing a click reaction at one end of the non-peptidyl polymer; and introducing a functional group capable of binding with an immunoglobulin Fc region or a physiologically active polypeptide at the other end of the non-peptidyl polymer.

Still another aspect of the present disclosure is to provide a physiologically active polypeptide linkage in which a physiologically active polypeptide is linked to the functional group capable of undergoing a click reaction at one end of the compound according to an aspect.

Still another aspect of the present disclosure is to provide an immunoglobulin Fc region linkage in which an immunoglobulin Fc region is linked to the functional group capable of undergoing a click reaction at one end of the compound according to an aspect.

Still another aspect of the present disclosure is to provide a physiologically active polypeptide conjugate in which a physiologically active polypeptide and an immunoglobulin Fc region are linked to each other via the compound according to an aspect as a linker.

Advantageous Effects of Disclosure

A compound according to an aspect of the present disclosure may be stably linked to a target site of a physiologically active polypeptide and may form a conjugate with high production yield and stability, as compared with known linker compounds.

BEST MODE

Figure 1:
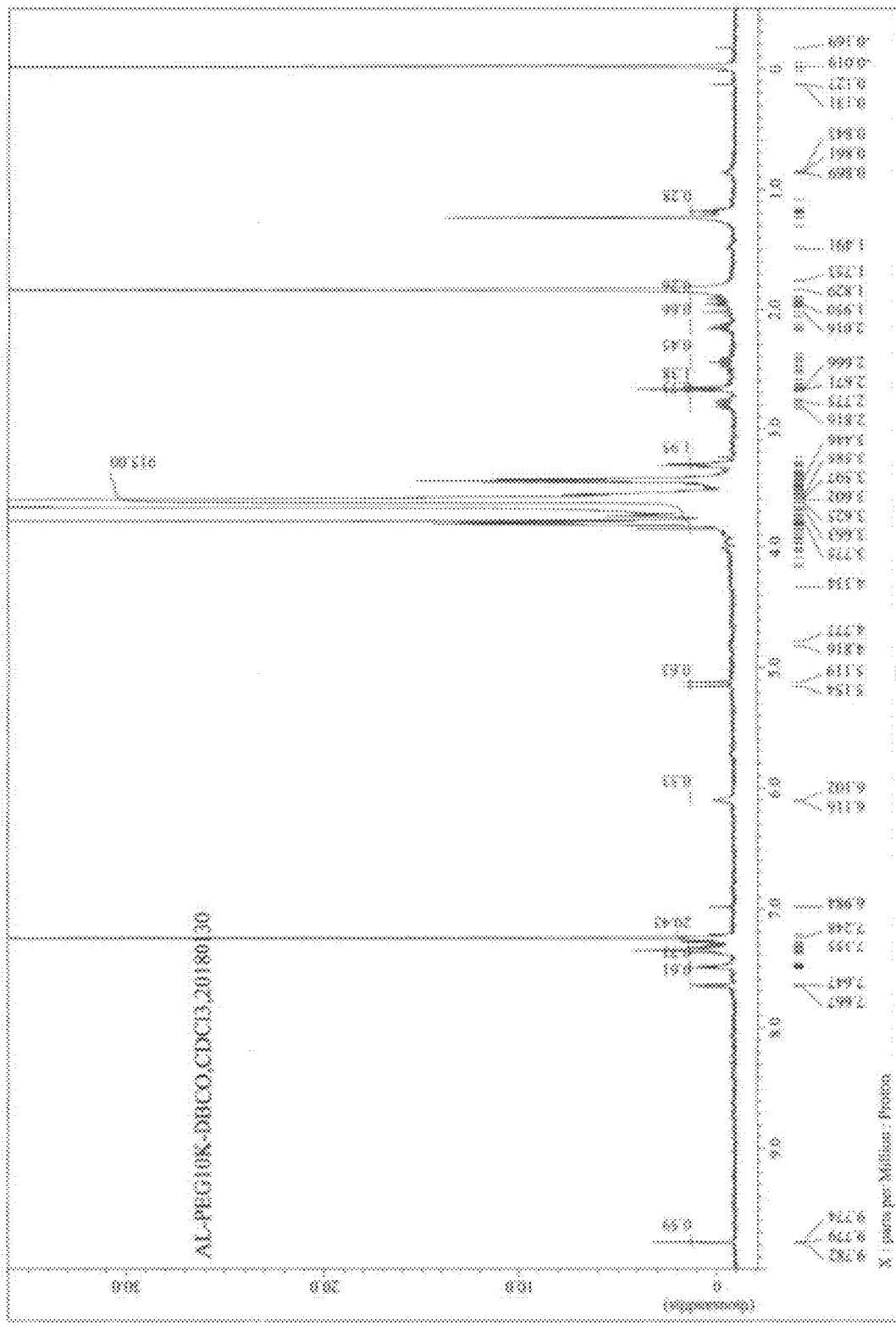
FIG. 1 shows $^1$H NMR result of a linker compound 6 (MW=10000) according to an embodiment.

Hereinafter, the present disclosure will be described in more detail.

Unless defined otherwise, all technical terms used herein have the same meanings as those generally understood by one of ordinary skill in the art to which the present disclosure belongs. Further, although methods or samples are described herein, those similar or equivalent thereto are also incorporated in the scope of the present disclosure. The numerical values described herein are considered to include the meaning of "about", unless otherwise specified. The contents of all the publications disclosed as references herein are incorporated in the present disclosure.

The present inventors have studied to develop a linker compound which may bind with a physiologically active polypeptide to improve in vivo stability of the physiologically active polypeptide, thereby increasing half-life thereof, and as a result, they developed a linker compound capable of more stably binding with a physiologically active polypeptide.

An aspect of the present disclosure provides a linker compound, in which a functional group capable of binding with an immunoglobulin Fc region or a physiologically active polypeptide is introduced at one end of a non-peptidyl polymer and a functional group capable of undergoing a click reaction is introduced at the other end thereof.

As used herein, the "functional group capable of binding with an immunoglobulin Fc region or a physiologically active polypeptide" refers to a functional group capable of binding with a functional group of an amino acid at any region of the immunoglobulin Fc region or the physiologically active polypeptide. The "functional group of an amino acid at any region of the immunoglobulin Fc region or the physiologically active polypeptide" may include, for example, an amino group (—$NH_2$) of lysine, an amine group (—NH—) of proline, a thiol group (—SH) of cysteine, etc. In a specific embodiment, the functional group capable of binding with the immunoglobulin Fc region or the physiologically active polypeptide refers to a functional group capable of binding with a functional group (an amine group, an amino group, or a thiol group) of N-terminal amino acid, lysine, or cysteine. The functional group capable of binding with the immunoglobulin Fc region or the physiologically active polypeptide may be, for example, selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, and derivatives thereof, but is not limited thereto.

As used herein, the term "functional group capable of undergoing a click reaction" refers to a functional group capable of undergoing a so-called click reaction in organic chemistry, and the click reaction may include alkyne-azide or alkyne-nitrone cycloaddition, thiol-ene click reaction (Hoyle, Charles E. et al., 2010, "Thiol-Ene Click Chemistry". Angewandte Chemie International Edition. 49 (9): 1540-1573), Diels-Alder reaction of dienophiles and dienes (Houk et al, 2013, 135, 15642-15649), cycloaddition of isonitriles and tetrazines (Henning et al., 2011, "Exploring isonitrile-based click chemistry for ligation with biomolecules", Organic & Biomolecular Chemistry. 9: 7303), etc., but is not limited thereto. The alkyne-azide or alkyne-nitrone cycloaddition may include Copper(I)-Catalyzed Azide-Alkyne Cycloaddition (CuAAC), Strain-promoted Azide-Alkyne Cycloaddition (SPAAC), or Strain-promoted Alkyne-Nitrone Cycloaddition (SPANC). The click reaction is widely known in the organic chemistry field.

The "functional group capable of undergoing a click reaction" may specifically include alkynyl, dienyl, isonitrile, etc., but is not limited thereto. The alkynyl may include linear or branched alkynyl, cycloalkynyl, arylcycloalkynyl, diarylcycloalkynyl, heterocycloalkynyl, arylheterocycloalkynyl, or diarylheterocycloalkynyl. The functional group capable of undergoing a click reaction which exists at one end of the compound may undergo the click reaction together with a functional group such as azide or nitrone which may be introduced to the physiologically active polypeptide or the immunoglobulin Fc region.

As used herein, "the functional group is introduced" means that any linkable atomic group containing the corresponding functional group is bound.

As used herein, the "non-peptidyl polymer" refers to any polymer known in the art which may bind with a physiologically active polypeptide to increase the in vivo half-life of the physiologically active polypeptide while having no peptidyl structure. The non-peptidyl polymer may be, for example, selected from the group consisting of polyethylene glycol, polypropylene glycol, a copolymer of ethylene glycol and propylene glycol, polyoxyethylated polyol, polyvinyl alcohol, polysaccharide, dextran, polyvinyl ethyl ether, polylactic acid (PLA), polylactic-glycolic acid (PLGA), lipid polymers, chitins, hyaluronic acid, and polysaccharides, but is not limited thereto.

As used herein, the term "halogen" refers to fluoro, chloro, bromo, or iodo.

The compound according to an aspect may include a compound selected from a compound of the following Formula 1, a stereoisomer thereof, a solvate thereof, and a pharmaceutically acceptable salt thereof:

R1-non-peptidyl polymer-X—R2   [Formula 1]

in Formula 1,

R1 is an aliphatic hydrocarbon group including a functional group selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, and derivatives thereof;

the non-peptidyl polymer is selected from the group consisting of polyethylene glycol, polypropylene glycol, a copolymer of ethylene glycol and propylene glycol, polyoxyethylated polyol, polyvinyl alcohol, polysaccharide, dextran, polyvinyl ethyl ether, polylactic acid (PLA), polylactic-glycolic acid (PLGA), lipid polymers, chitins, hyaluronic acid, and polysaccharides;

X is —$(CH_2)_j$NHCO— or —$(CH_2)_j$NHCS—, wherein j is an integer of 0 to 6;

R2 is —$(R3)_k$-$(Z)_l$—$(R4)_m$-$(CZ)_p$—Y—, wherein R3 and R4 is each independently $C_1$-$C_6$ alkylene, $C_6$-$C_{20}$ arylene, or $C_5$-$C_{20}$ heteroarylene having 1 to 3 heteroatoms selected from N, O, and S, Z is be O or S, Y is $C_2$-$C_6$ alkynyl, cycloalkynyl, bicycloalkynyl, arylcycloalkynyl, diarylcycloalkynyl, heterocycloalkynyl, or diarylheterocycloalkynyl (wherein each cycloalkynyl has 3 to 8 carbon atoms, each aryl has 5 to 8 carbon atoms, and each heterocycloalkynyl is a saturated ring including 3 to 8 atoms and having heteroatoms selected from N, O, and S in 1 to 3 of ring atoms), k, l, m, and p are each independently an integer of 0 to 3, provided that all of them may not be 0 at the same time, and the alkynyl, cycloalkynyl, bicycloalkynyl, arylcycloalkynyl, diarylcycloalkynyl, heterocycloalkynyl, or diarylheterocycloalkynyl may be substituted or unsubstituted with $C_1$-$C_6$ alkyl, $C_1$-$C_6$ alkoxy, $C_1$-$C_6$ alkoxycarbonyl, oxo, or halogen.

In R1, the aliphatic hydrocarbon group may include linear or branched alkyl having 1 to 20 carbon atoms, specifically, 1 to 12 carbon atoms, and more specifically 1 to 6 carbon atoms; linear or branched alkenyl containing one or more carbon-carbon double bonds and having 2 to 15 carbon atoms, specifically 2 to 12 carbon atoms, and more specifically 2 to 6 carbon atoms; linear or branched alkynyl containing one or more carbon-carbon triple bonds and having 2 to 15 carbon atoms, specifically 2 to 12 carbon atoms, and more specifically 2 to 6 carbon atoms. The alkyl may be, for example, selected from the group consisting of methyl, ethyl, n-propyl, isopropyl, n-butyl, t-butyl, n-pentyl, heptyl, nonyl, and decyl. The alkenyl may be, for example, selected from the group consisting of ethenyl, propenyl, n-butenyl, 3-methylbut-2-enyl, n-pentenyl, octenyl, and decenyl. The alkynyl may be, for example, selected from the group consisting of ethynyl, propynyl, 2-butynyl, 3-methylbutynyl, n-pentynyl, and decynyl. The alkyl, alkenyl, alkynyl may be substituted or unsubstituted with a group selected from the group consisting of $C_1$-$C_6$ alkyl and halogen.

R1 may be a $C_1$-$C_6$ aliphatic hydrocarbon group containing an aldehyde group. In a specific embodiment, R1 is $C_1$-$C_6$ alkyl (i.e., HC(O)—$C_{1-6}$ alkyl) containing an aldehyde group, for example, n-pentaldehyde, n-butyraldehyde, propionaldehyde, or acetaldehyde.

Y may be selected from the group consisting of bicyclo [6.1.0]nonyne (BCN), dibenzocyclooctyne (DBCO), difluorinated cyclooctyne (DIFO), DIFO2, DIFO3, dibenzoannulated cyclooctyne (DIBO), biarylazacyclooctynone (BARAC), cyclooctyne (OCT), aryl-less cyclooctyne (ALO), monofluorinated cyclooctyne (MOFO), dimethoxyazacyclooctyne (DIMAC), 2,3,6,7-tetramethoxy-DIBO (TMDIBO), carboxymethylmonobenzocyclooctyne (COMBO), pyrrolocyclooctyne (PYRROC), dibenzo-azacyclooctyne (DIBAC), 3,3,6,6-tetramethylthiacycloheptyne (TMTH), Sondheimer diyne, and sulfonylated DIBO (S-DIBO), but is not limited thereto.

In a specific embodiment, the non-peptidyl polymer in Formula 1 may have a structure of the following Formula 1a having a polyethylene glycol structure:

[Formula 1a]

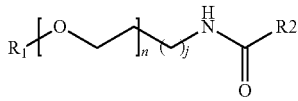

in Formula 1a, n is an integer of 20 to 1000, specifically an integer of 20 to 500, and more specifically an integer of 20 to 250;

j is an integer of 0 to 6, and specifically, an integer of 0 or 2;

R1 is an aliphatic hydrocarbon group including a functional group selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, and derivatives thereof;

R2 is —(R3)$_k$-(Z)$_l$—(R4)$_m$-(CZ)$_p$—Y, wherein R3 and R4 are each independently $C_1$-$C_6$ alkylene, $C_6$-$C_{20}$ arylene, or $C_5$-$C_{20}$ heteroarylene having 1 to 3 heteroatoms selected from N, O, and S, Z is O or S, Y is selected from the group consisting of bicyclo[6.1.0] nonyne (BCN), dibenzocyclooctyne (DBCO), difluorinated cyclooctyne (DIFO), DIFO2, DIFO3, dibenzoannulated cyclooctyne (DIBO), biarylazacyclooctynone (BARAC), cyclooctyne (OCT), aryl-less cyclooctyne (ALO), monofluorinated cyclooctyne (MOFO), dimethoxyazacyclooctyne (DIMAC), 2,3,6,7-tetramethoxy-DIBO (TMDIBO), carboxymethylmonobenzocyclooctyne (COMBO), pyrrolocyclooctyne (PYRROC), dibenzo-aza-cyclooctyne (DIBAC), 3,3,6,6-tetramethylthiacycloheptyne (TMTH), Sondheimer diyne, and sulfonylated DIBO (S-DIBO), k, l, m, and p are each independently an integer of 0 to 3, provided that all of them may not be 0 at the same time.

In Formulae 1 and 1a, $C_6$-$C_{20}$ arylene may be, for example, a divalent form of an aromatic group such as benzene, biphenylene, triphenylene, naphthalene, anthracene, binaphthylene, phenanthrene, pyrene, dihydropyrene, chrysene, perylene, tetracene, pentacene, benzopyrene, fluorene, indene, indenofluorene, or spirobifluorene, and more specifically, a divalent form of benzene, $C_5$-$C_{20}$ heteroarylene may be, for example, a divalent form of a heteroaromatic group such as a 5-membered ring (e.g., pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, and 1,3,4-thiadiazole); a 6-membered ring (e.g., pyridine, pyridazine, pyrimidine, pyrazine, 1,3,5-triazine, 1,2,4-triazine, 1,2,3-triazine, 1,2,4,5-tetrazine, 1,2,3,4-tetrazine, and 1,2,3,5-tetrazine); or a fused group (e.g., carbazole, indole, isoindole, indolizine, indazole, benzimidazole, benzotriazole, purine, naphthimidazole, phenanthrimidazole, pyridimidazole, pyrazineimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3-b]thiophene, thieno[3,2-b]thiophene, dithienothiophene, dithienopyridine, isobenzothiophene, dibenzothiophene, benzothiadiazothiophene, etc).

In a specific embodiment, Formula 1a may have any structure of the following Formulae 2a to 2n:

[Formula 2a]

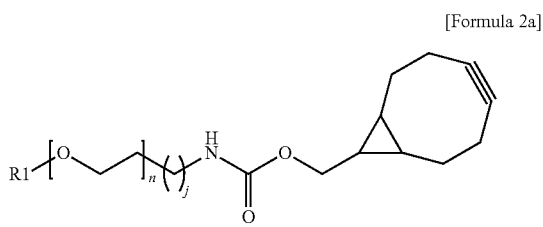

[Formula 2b]

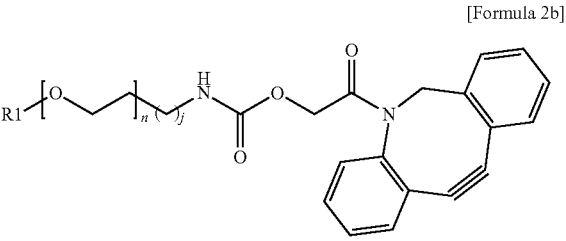

[Formula 2c]

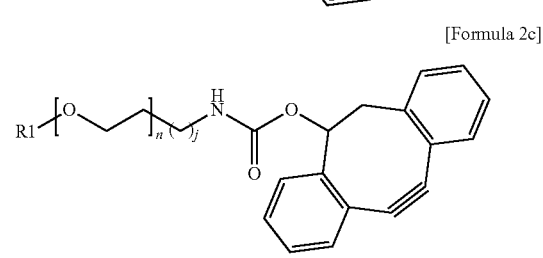

[Formula 2d]

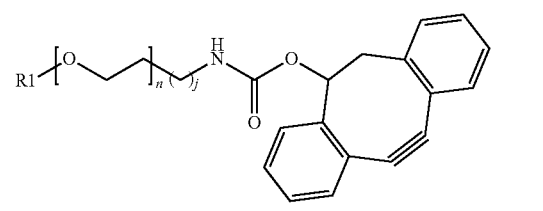

[Formula 2e]

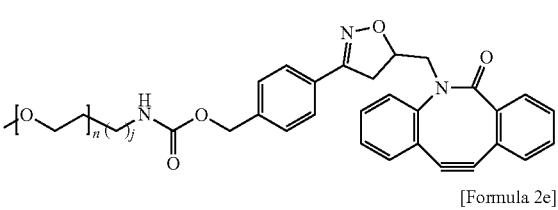

[Formula 2f]

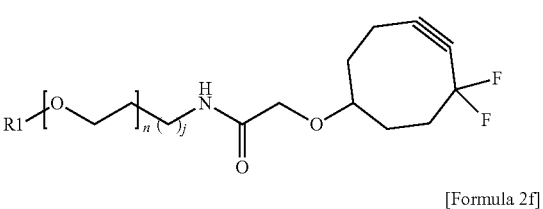

[Formula 2g]

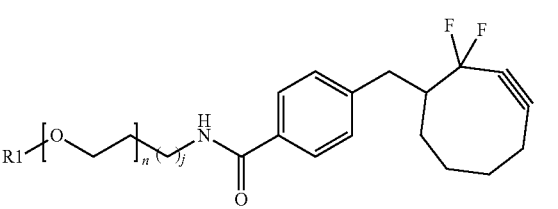

[Formula 2h]

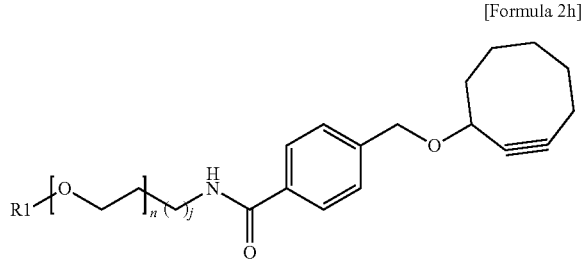

[Formula 2i]

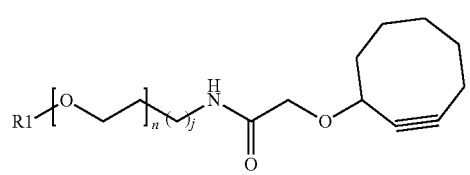

[Formula 2j]

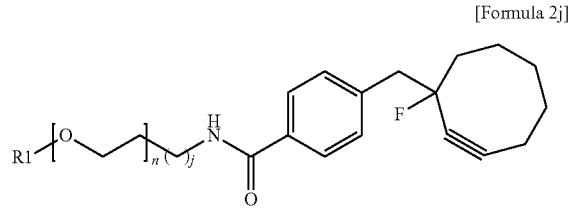

[Formula 2k]

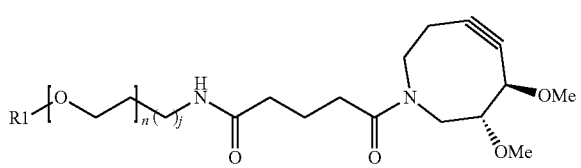

[Formula 2l]

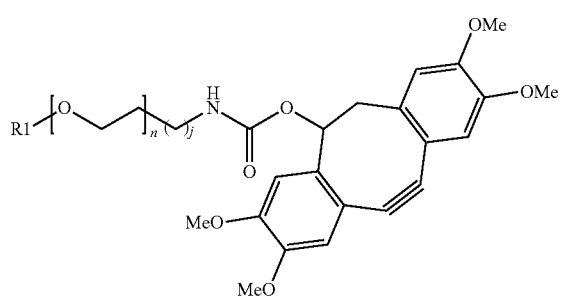

[Formula 2m]

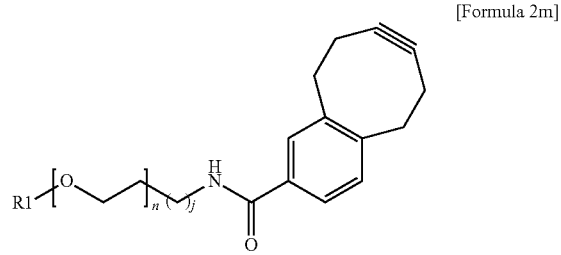

[Formula 2n]

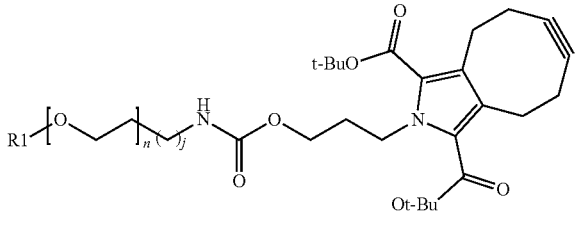

in Formulae 2a to 2n, n may be an integer of 20 to 1000, specifically an integer of 20 to 500, and more specifically an integer of 20 to 250;

j may be an integer of 0 to 6, and specifically, an integer of 0 or 2;

R1 may be a $C_1$-$C_6$ aliphatic hydrocarbon group including an aldehyde group.

The compound according to an aspect may exist in the form of a pharmaceutically acceptable salt. As the salt, an acid addition salt formed by a pharmaceutically acceptable free acid is useful. As used herein, the term "pharmaceutically acceptable salt" refers to any organic or inorganic addition salt of the compound, whose concentration has effective action because it is relatively non-toxic and harmless to patients and whose side effects do not degrade the beneficial efficacy of the compound which is represented by Formula 1, 1a, or 2a to 2n. The acid addition salt may be prepared by a common method, for example, by dissolving the compound in excessive quantity of an aqueous solution of the acid followed by precipitation of the resultant salt using a water-miscible organic solvent, for example, methanol, ethanol, acetone, or acetonitrile. The compound of the same molar amount and acid or alcohol in water (e.g., glycol monomethyl ether) may be heated, and subsequently, the resultant mixture may be dried by evaporating, or precipitated salts may be filtered by suction.

Further, pharmaceutically acceptable metal salts may be prepared using a base. For example, an alkali metal salt or an alkali earth metal salt may be obtained by dissolving the compound in excessive quantity of an alkali metal hydroxide or alkali earth metal hydroxide solution, filtering an undissolved compound salt, and drying the filtrate by evaporation.

Further, the present disclosure may include the compound of Formula 1, 1a, or 2a to 2n and a pharmaceutically acceptable salt thereof as well as a solvate which may be prepared therefrom.

Further, when the compound of Formula 1, 1a, or 2a to 2n has an asymmetric carbon center (chiral carbon) in its substituent, it may exist in the form of an enantiomer (R or S isomer), a racemate, a diastereomer, or a mixture thereof. Further, when the compound of Formula 1, 1a, or 2a to 2n includes a bridged ring, it may exist as an exo or endo isomer, and for example, the compound of Formula 2a may exist as an exo or endo isomer.

The compound according to an aspect may have a molecular weight in the range of 0.1 kDa to 100 kDa, specifically 0.1 kDa to 50 kDa, and more specifically 0.3 kDa to 10 kDa, but is not limited thereto.

Another aspect of the present disclosure provides a method of preparing the compound according to an aspect of the present disclosure, the method including:

introducing a functional group capable of undergoing a click reaction at one end of the non-peptidyl polymer; and introducing a functional group capable of binding with an immunoglobulin Fc region or a physiologically active polypeptide at the other end of the non-peptidyl polymer.

The above description of the compound according to an aspect of the present disclosure may be applied as it is to the preparation method.

The preparation method may include 1) introducing an amino group (—NH$_2$) at one end of the non-peptidyl polymer, and then introducing R2 at one end of the non-peptidyl polymer by an amide bond with the amino group; and 2) introducing an aliphatic hydrocarbon group including a functional group selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, and derivatives thereof at the other end of the non-peptidyl polymer to which R2 is introduced, wherein R2 is the same as defined in Formula 1 or 1a.

In a specific embodiment, the non-peptidyl polymer of 1) may be polyethylene glycol.

In a specific embodiment, the non-peptidyl polymer of 1) may have a molecular weight in the range of 0.1 kDa to 100 kDa, specifically 0.1 kDa to 50 kDa, and more specifically 0.3 kDa to 10 kDa, but is not limited thereto.

In a specific embodiment, 2) may be introducing a $C_1$-$C_6$ aliphatic hydrocarbon group including an aldehyde group at the other end of the non-peptidyl polymer to which R2 is introduced.

Specific reaction conditions for a method of introducing the functional group capable of undergoing a click reaction at one end of the non-peptidyl polymer and a method of introducing the functional group capable of binding with the immunoglobulin Fc region or physiologically active polypeptide at the other end of the non-peptidyl polymer may be appropriately determined by those skilled in the organic chemistry field using a known technology.

The above preparation method is described only for illustrating a method of preparing the compound according to an aspect. The method of preparing the compound according to an aspect is not limited thereto and may be appropriately modified by using a technology known in the art.

Still another aspect of the present disclosure provides a physiologically active polypeptide linkage in which a physiologically active polypeptide is linked to the functional group capable of undergoing a click reaction at one end of the compound according to an aspect.

Still another aspect of the present disclosure provides an immunoglobulin Fc region linkage in which an immunoglobulin Fc region is linked to the functional group capable of undergoing a click reaction at one end of the compound according to an aspect.

As used herein, the term "physiologically active polypeptide linkage" refers to a construct in which the physiologically active polypeptide is linked to the compound according to an aspect, and the term "immunoglobulin Fc region linkage" refers to a construct in which the immunoglobulin Fc region is linked to the compound according to an aspect. The linkage may be a covalent bond, but is not limited thereto. Hereinafter, the physiologically active polypeptide linkage or the immunoglobulin Fc region linkage is also called "physiologically active polypeptide or immunoglobulin Fc region linkage".

The physiologically active polypeptide or immunoglobulin Fc region linkage may include a physiologically active polypeptide or immunoglobulin Fc region linkage in which the physiologically active polypeptide or immunoglobulin Fc region is linked to the compound of Formula 1 or 1a via the functional group Y of the compound of Formula 1 or 1a.

To link the physiologically active polypeptide or immunoglobulin Fc region to the functional group capable of undergoing the click reaction, specifically, the functional group Y of Formula 1, the functional group capable of undergoing the click reaction with the functional group Y are introduced to the physiologically active polypeptide, and then the linkage may be formed by the click reaction. The functional group capable of undergoing the click reaction which may be introduced to the physiologically active polypeptide or immunoglobulin Fc region may be, for example, azide, nitrone, etc. To introduce azide or nitrone to the physiologically active polypeptide or immunoglobulin Fc region, an amino acid bound with azide or nitrone may be linked to the physiologically active polypeptide or immunoglobulin Fc region by amide bonds between amino acids. The amino acid bound with azide or nitrone may be directly prepared or purchased from a commercially available source. In a specific embodiment, azidolysine ($N_3$-lysine) may be linked to the physiologically active polypeptide by amide bonds, and the azidolysine may be purchased from a commercially available source (Sigma Aldrich, Fmoc-azidolysine). In a specific embodiment, azidolysine ($N_3$-lysine) may be linked to the C-terminus of the physiologically active polypeptide by amide bonds.

In another specific embodiment, azide or nitrone may be directly linked to an amino acid in the physiologically active polypeptide or immunoglobulin Fc region without separate amino acids. To this end, a functional group which is linkable with an amino acid to be linked with azide or nitrone may be first linked to azide or nitrone. For example, N-hydroxysuccinimidyl azide (e.g., NHS-azide, NHS-PEG4-azide) may be reacted with the physiologically active polypeptide or immunoglobulin Fc region to be directly linked thereto via an amino acid (e.g., lysine, N-terminal amino acid) present in the physiologically active polypeptide or immunoglobulin Fc region.

In another specific embodiment, azide or nitrone may be linked via an amino acid added or substituted to the physiologically active polypeptide or immunoglobulin Fc region. To this end, an amino acid to be linked with azide or nitrone may be added or substituted to the physiologically active polypeptide or immunoglobulin Fc region, and then a functional group linkable with the added or substituted amino acid may be linked to the azide or nitrone. For example, lysine may be added or substituted to the physiologically active polypeptide or immunoglobulin Fc region, and N-hydroxysuccinimidyl azide (e.g., NHS-azide, NHS-PEG4-azide) may be linked via the added or substituted lysine.

The physiologically active polypeptide or immunoglobulin Fc region to which azide or nitrone is introduced may be linked with the linker compound by forming triazole (reaction of azide and an ethynylene group —C≡C— of Y) or isoxazolidine (reaction of nitrone and an ethynylene group —C≡C— of Y) together with the functional group capable of undergoing click reaction at one end of the linker compound according to an aspect, for example, the functional group Y of the compound of Formula 1 or 1a by cycloaddition by a click reaction. Specific conditions for the preparation method may be appropriately determined by those skilled in the art using the common knowledge.

In a specific embodiment, the physiologically active polypeptide linkage may be a physiologically active polypeptide linkage, in which the azide group is introduced to the physiologically active polypeptide and then the azide group and the ethynylene group of the functional group Y of the compound of Formula 1 or 1a may be bound to each other by forming 1,2,3-triazole by cycloaddition through click reaction.

In a specific embodiment, the physiologically active polypeptide linkage may have any one Formula of the following Formulae 3a to 3l:
[Formula 3a]
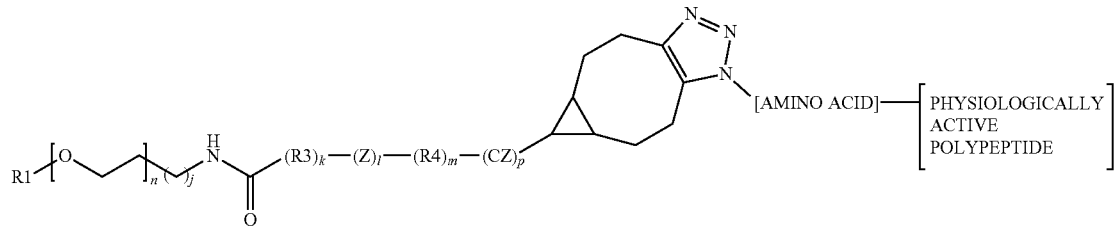
[Formula 3b]
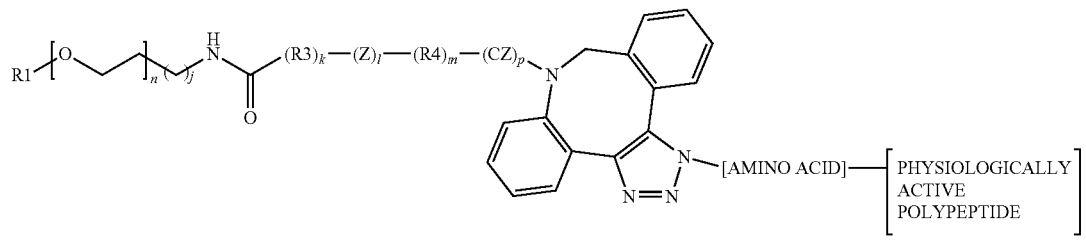
[Formula 3c]
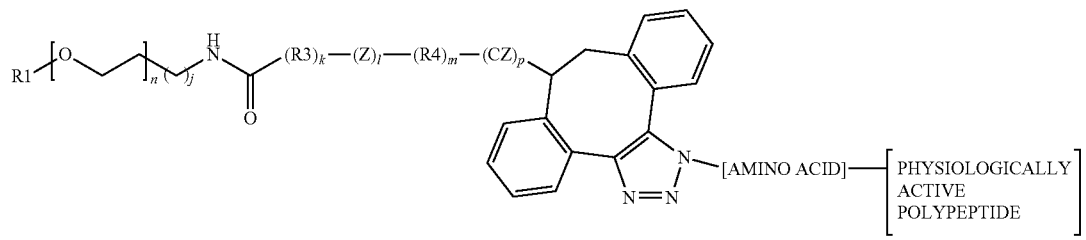
[Formula 3d]
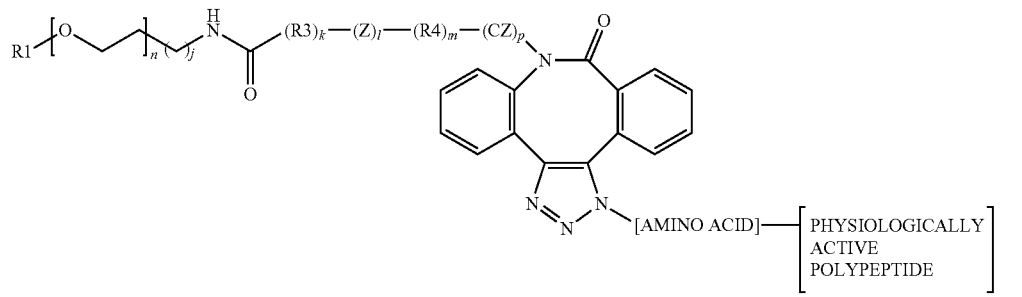
[Formula 3e]
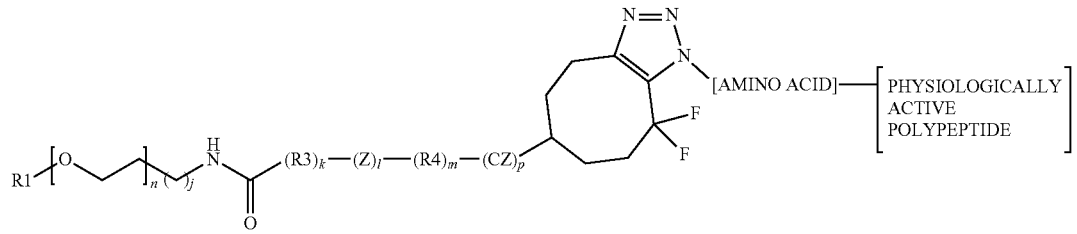
[Formula 3f]
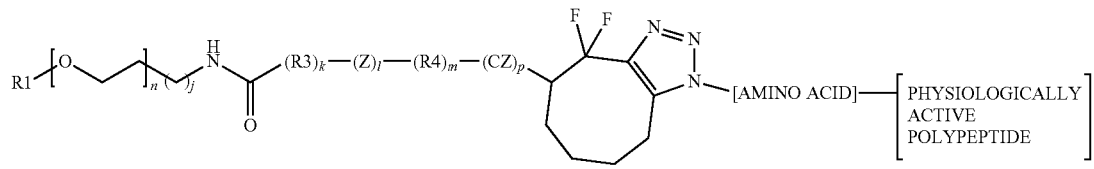

-continued
[Formula 3g]
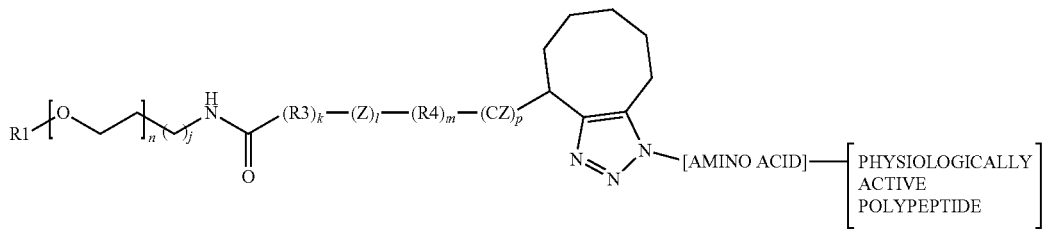
[Formula 3h]
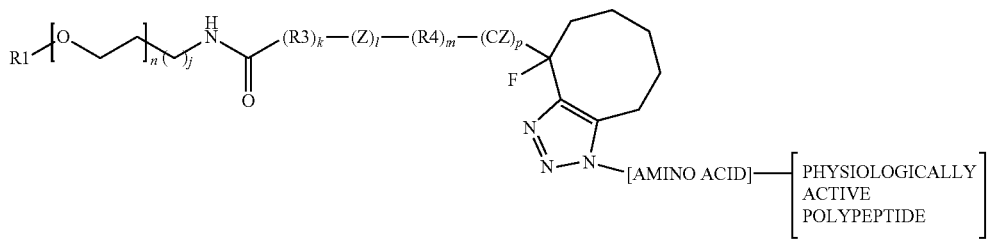
[Formula 3i]
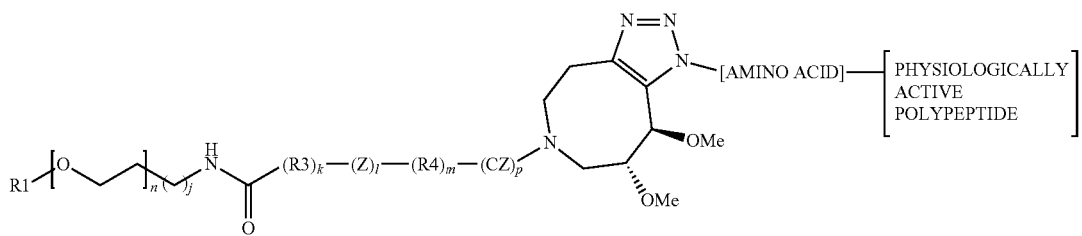
[Formula 3j]
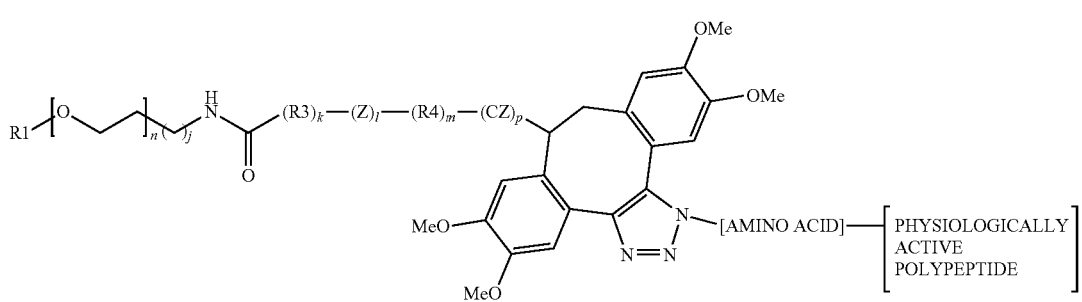
[Formula 3k]
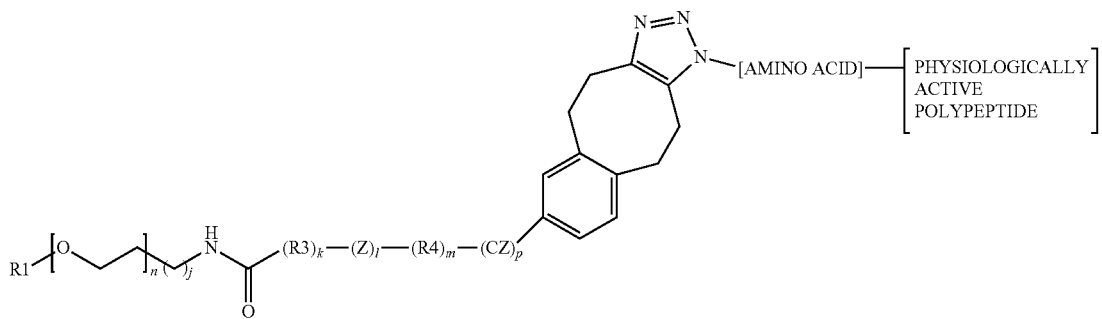

-continued

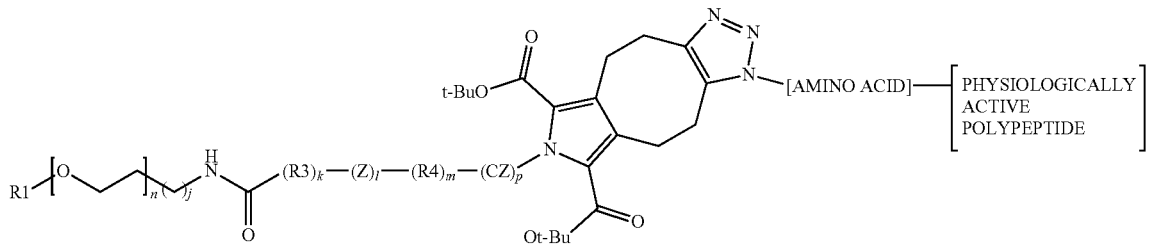

[Formula 3l]

in Formulae 3a to 3l, R1, R3, R4, Z, j, k, l, m, n, and p are the same as defined in Formula 1a; and

[amino acid] is any one of amino acids constituting the physiologically active polypeptide sequence of a natural form, or an added or substituted amino acid that does not belong thereto.

In a specific embodiment, [amino acid] of Formulae 3a to 3l is a moiety excluding an epsilon-amino group from a lysine residue of the natural sequence of the physiologically active polypeptide, and triazole nitrogen of Formulae 3a to 3l may be linked to epsilon carbon of the lysine side chain.

In another specific embodiment, [amino acid] of Formulae 3a to 3l is a moiety excluding the alpha-amino group from the N-terminal amino acid of the natural sequence of the physiologically active polypeptide, and triazole nitrogen of Formulae 3a to 3l may be linked to alpha carbon of the N-terminal amino acid.

In a specific embodiment, the physiologically active polypeptide linkage may be a physiologically active polypeptide linkage having any one structural formula of the following Formulae 4a to 4n:

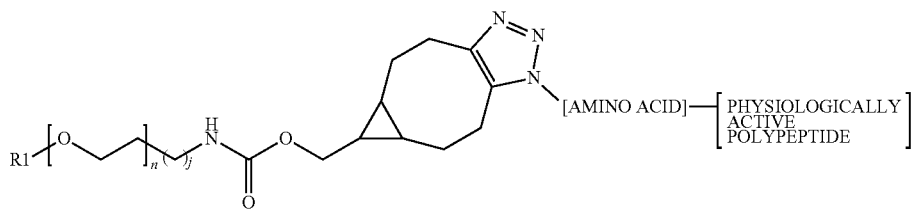

[Formula 4a]

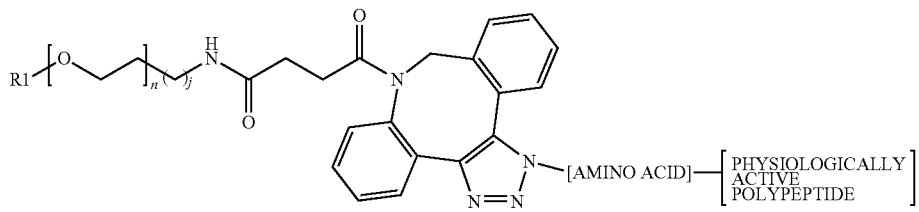

[Formula 4b]

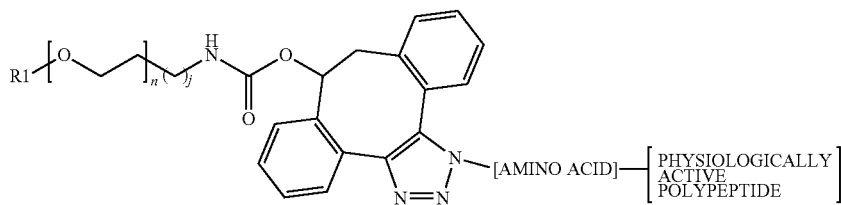

[Formula 4c]

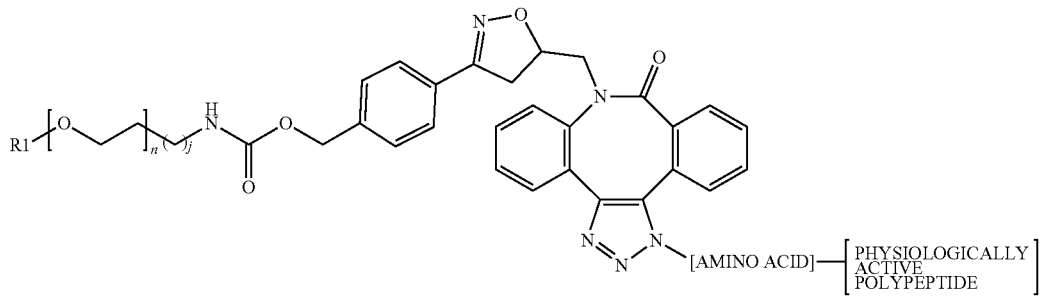

[Formula 4d]

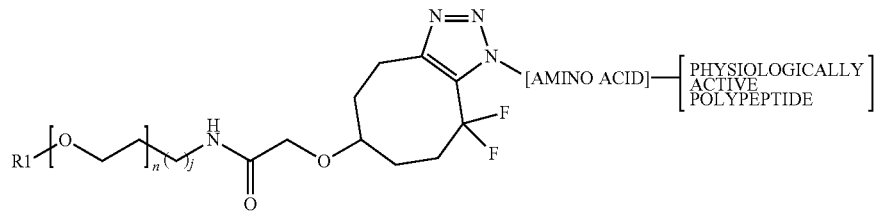
[Formula 4e]
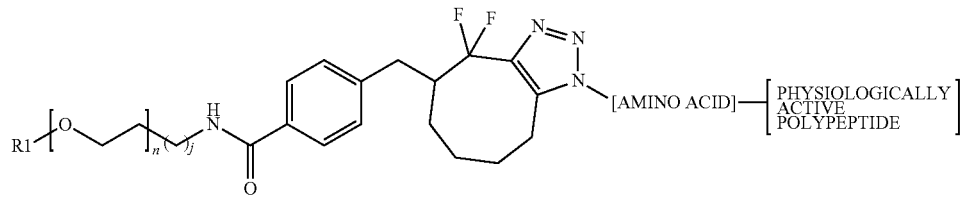
[Formula 4f]
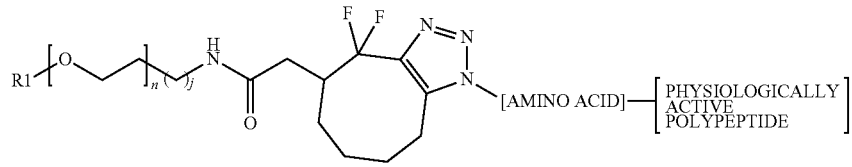
[Formula 4g]
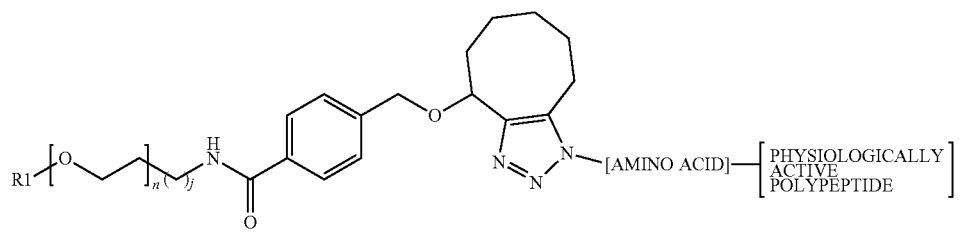
[Formula 4h]
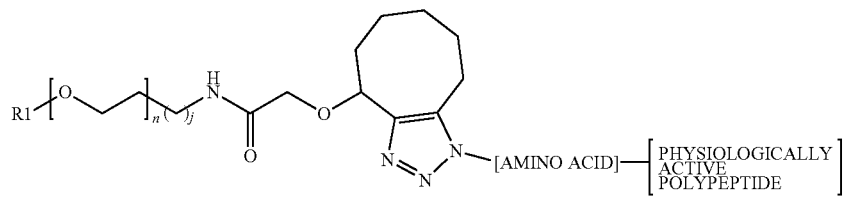
[Formula 4i]
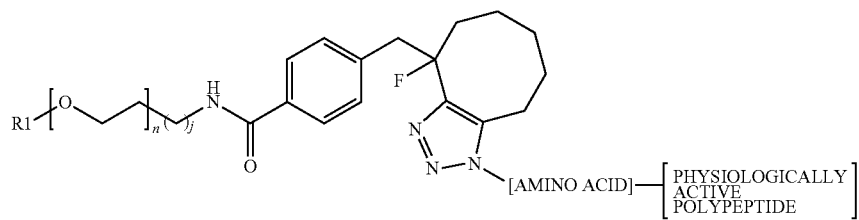
[Formula 4j]
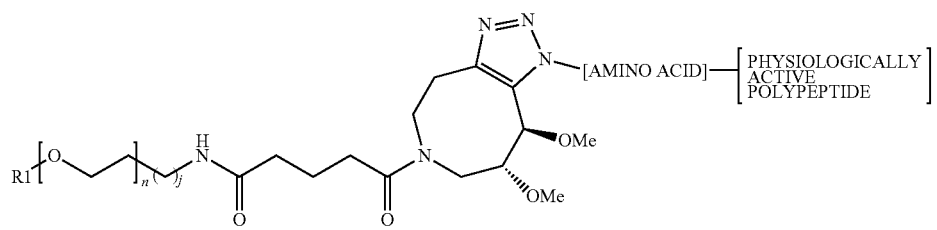
[Formula 4k]

[Formula 4l]

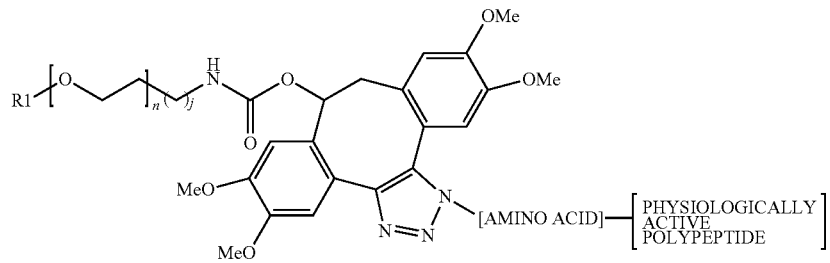

[Formula 4m]

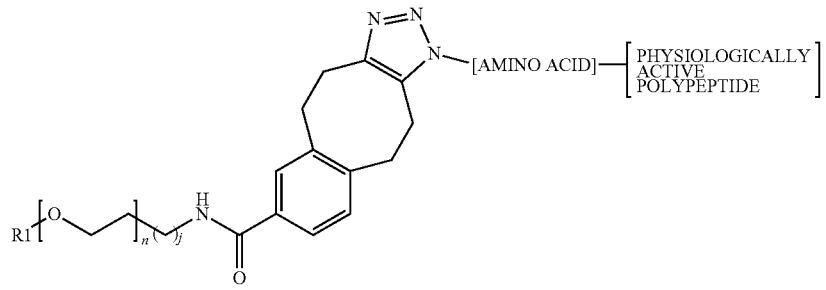

[Formula 4n]

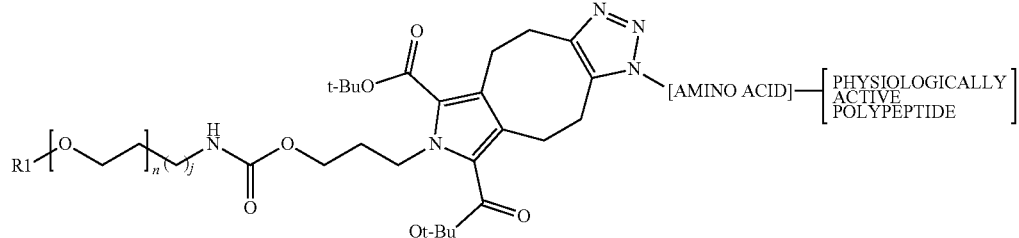

in Formulae 4a to 4n,

R1, j, and n are the same as defined in Formula 1a, and

[amino acid] is any one of amino acids constituting the physiologically active polypeptide sequence of the natural form, or an added or substituted amino acid that does not belong thereto.

In a specific embodiment, [amino acid] of Formulae 4a to 4n is a moiety excluding the epsilon-amino group from the lysine residue of the natural sequence of the physiologically active polypeptide, and triazole nitrogen of Formulae 4a to 4n may be linked to epsilon carbon of the lysine side chain.

In another specific embodiment, [amino acid] of Formulae 4a to 4n is a moiety excluding the alpha-amino group from the N-terminal amino acid of the natural sequence of the physiologically active polypeptide, and triazole nitrogen of Formulae 4a to 4n may be linked to alpha carbon of the N-terminal amino acid.

Still another aspect of the present disclosure provides a physiologically active polypeptide linkage in which a physiologically active polypeptide is linked to the functional group R1 at one end of the compound according to an aspect.

Still another aspect of the present disclosure provides an immunoglobulin Fc region linkage in which an immunoglobulin Fc region is linked to the functional group R1 at one end of the compound according to an aspect.

Any amino acid of the physiologically active polypeptide or the immunoglobulin Fc region may form a covalent bond with the functional group R1 of the compound of Formula 1 or 1a. Specifically, R1 which is an aliphatic hydrocarbon group including a functional group selected from the group consisting of 2,5-dioxopyrrolidinyl, 2,5-dioxopyrrolyl, aldehyde, maleimide, $C_6$-$C_{20}$aryl disulfide, $C_5$-$C_{20}$heteroaryl disulfide, vinyl sulfone, thiol, halogenated acetamide, succinimide, p-nitrophenyl carbonate, and derivatives thereof may be covalently linked to a functional group (e.g., amino (—$NH_2$) of lysine, amine (—NH—) of proline, thiol (—SH) of cysteine, etc.) of any amino acid of the physiologically active polypeptide or the immunoglobulin Fc region, and more specifically, may be covalently linked to a functional group of the N-terminal amino acid. In a specific embodiment, when the N-terminus of the physiologically active polypeptide has an amine group or an amino group, it may form a covalent bond with R1 including the aldehyde functional group by reductive amination. As used herein, the term "reductive amination" refers to a reaction in which an amine group or an amino group of one reactant reacts with aldehyde (i.e., a functional group capable of undergoing reductive amination) of another reactant to form an imine, and then an amine bond is formed by reduction, and the reductive amination is an organic synthetic reaction widely known in the art.

Still another aspect of the present disclosure provides a physiologically active polypeptide conjugate in which a physiologically active polypeptide and an immunoglobulin Fc region are linked to each other via the compound according to an aspect as a linker.

As used herein, the term "physiologically active polypeptide conjugate" refers to a construct in which a physiologically active polypeptide and an immunoglobulin Fc region are linked to each other via the compound according to an aspect as a linker to form a single substance. The linkage may be a covalent bond, but is not limited thereto.

The physiologically active polypeptide conjugate may include a physiologically active polypeptide conjugate in which the physiologically active polypeptide and the immunoglobulin Fc region are linked to each other via the compound of Formula 1 or 1a as a linker.

In the physiologically active polypeptide conjugate, the physiologically active polypeptide may be linked to any one end of both ends of the linker compound including the compound of Formula 1 or 1a and the immunoglobulin Fc region may be linked to the other end of the linker compound including the compound of Formula 1 or 1a.

With regard to the above conjugate, a method of linking the physiologically active polypeptide to any one end of the linker compound including the compound of Formula 1 or 1a may be performed as in the above description of the physiologically active polypeptide linkage formed via the functional group Y or R1 at one end of the compound according to an aspect.

With regard to the above conjugate, a method of linking the immunoglobulin Fc region to any one end of the linker compound including the compound of Formula 1 or 1a may be performed as in the above description of the immunoglobulin Fc region linkage formed via the functional group Y or R1 at one end of the compound according to an aspect.

In a specific embodiment, the physiologically active polypeptide conjugate may be a physiologically active polypeptide conjugate, in which an azide group is introduced to the physiologically active polypeptide and then the azide group and the ethynylene group of R2 of Formula 1 may be bound to each other by forming 1,2,3-triazole by cycloaddition through click reaction, and an amino acid of the immunoglobulin Fc region is linked to R1 of the compound of Formula 1 via a covalent bond. In another specific embodiment, the physiologically active polypeptide conjugate may be a physiologically active polypeptide conjugate, in which an azide group is introduced to the physiologically active polypeptide and then the azide group and the ethynylene group of R2 of Formula 1 may be bound to each other by forming 1,2,3-triazole by cycloaddition through click reaction, and N-terminal proline of the immunoglobulin Fc region may form an amine bond with R1 of Formula 1 by reductive amination.

In a specific embodiment, the physiologically active polypeptide conjugate may be a physiologically active polypeptide conjugate having any one structural formula of the following Formulae 5a to 5l:

[Formula 5a]
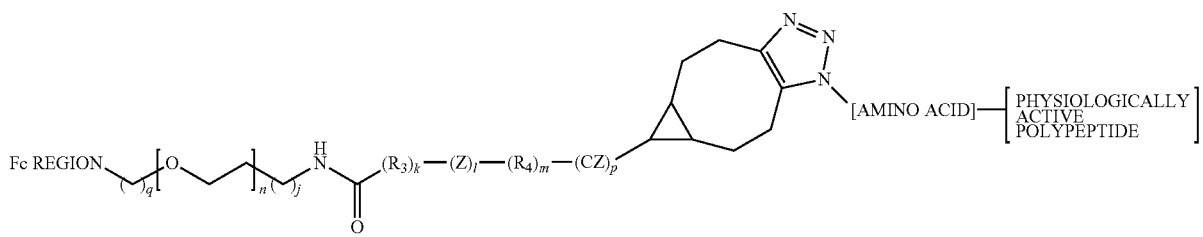

[Formula 5b]
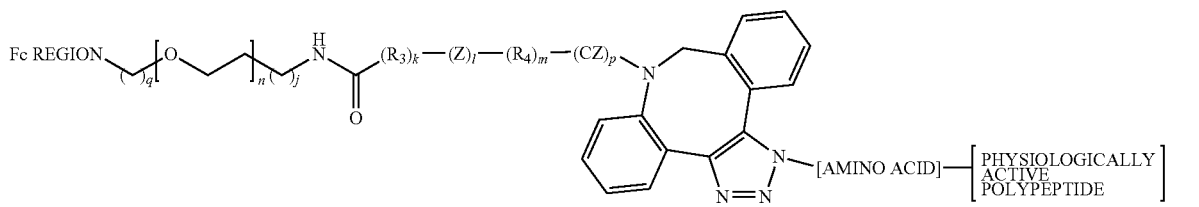

[Formula 5c]
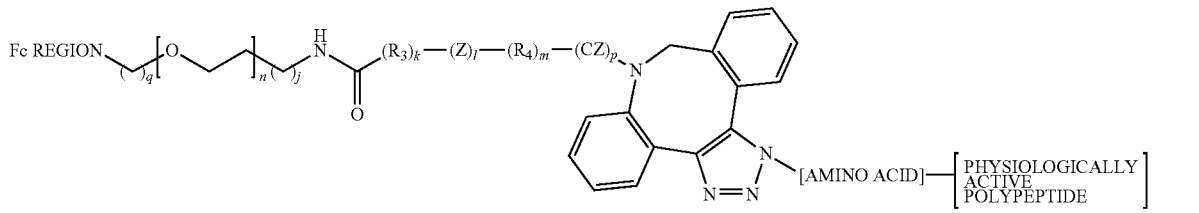

[Formula 5d]
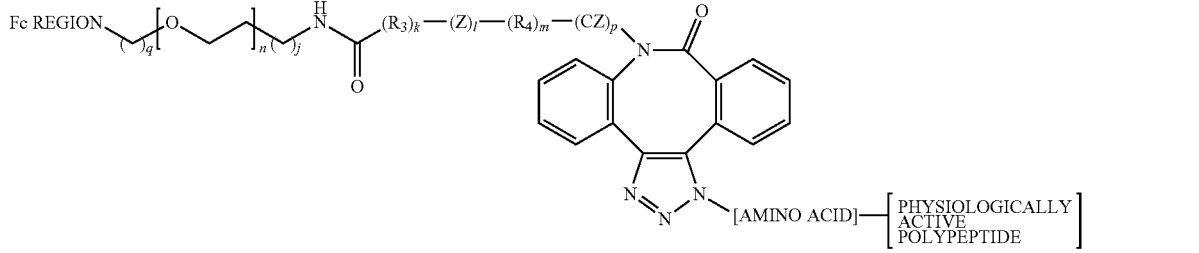

[Formula 5e]
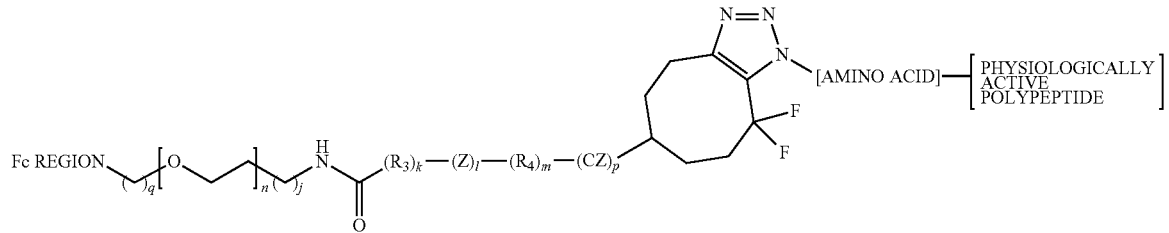
[Formula 5f]
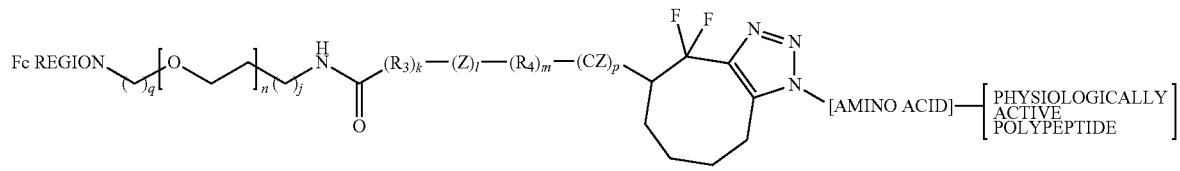
[Formula 5g]
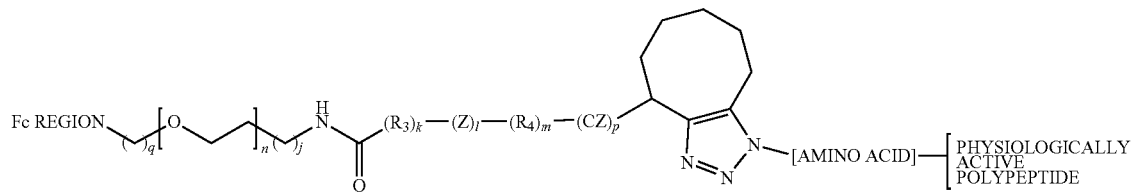
[Formula 5h]
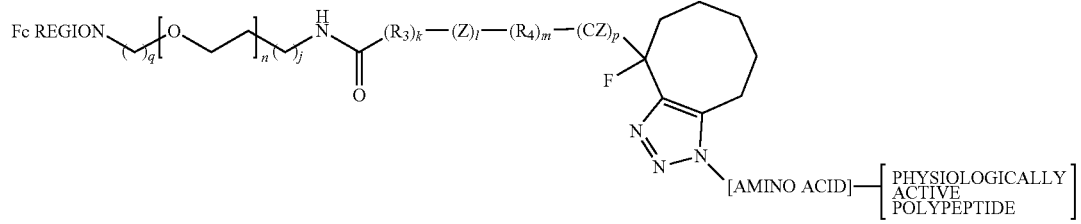
[Formula 5i]
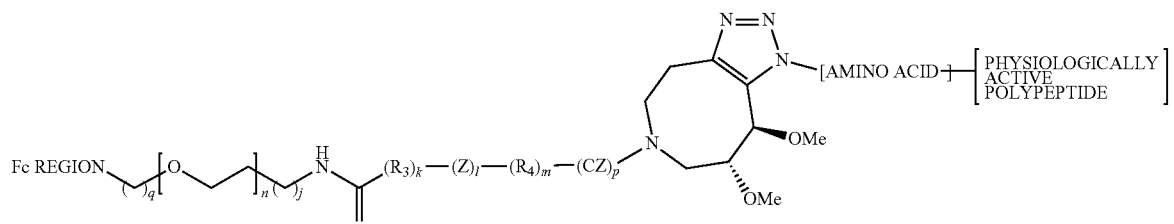
[Formula 5j]
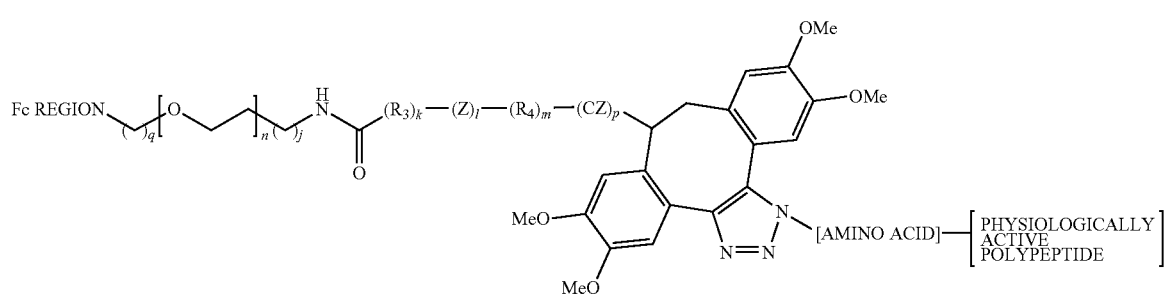

[Formula 5k]

[Formula 5l]

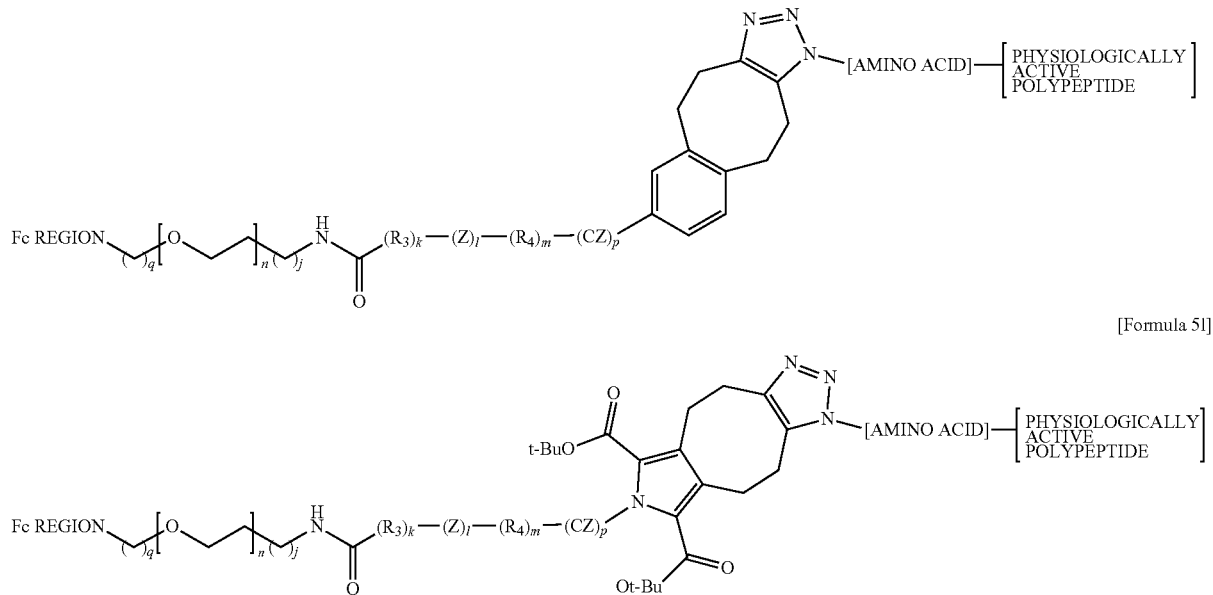

in Formulae 5a to 5l,

R3, R4, Z, j, k, l, m, n, and p are the same as defined in Formula 1a;

[amino acid] is any one of amino acids constituting the physiologically active polypeptide sequence of the natural form, or an added or substituted amino acid that does not belong thereto; and q is an integer of 1 to 6.

In a specific embodiment, [amino acid] of Formulae 5a to 5l is a moiety excluding the epsilon-amino group from the lysine residue of the natural sequence of the physiologically active polypeptide, and triazole nitrogen of Formulae 5a to 5l may be linked to epsilon carbon of the lysine side chain.

In another specific embodiment, [amino acid] of Formulae 5a to 5l is a moiety excluding an alpha-amino group from the N-terminal amino acid of the natural sequence of the physiologically active polypeptide, and triazole nitrogen of Formulae 5a to 5l may be linked to alpha carbon of the N-terminal amino acid.

In a specific embodiment, the physiologically active polypeptide conjugate may be a physiologically active polypeptide conjugate having any one structural formula of the following Formulae 6a to 6n:

[Formula 6a]

[Formula 6b]

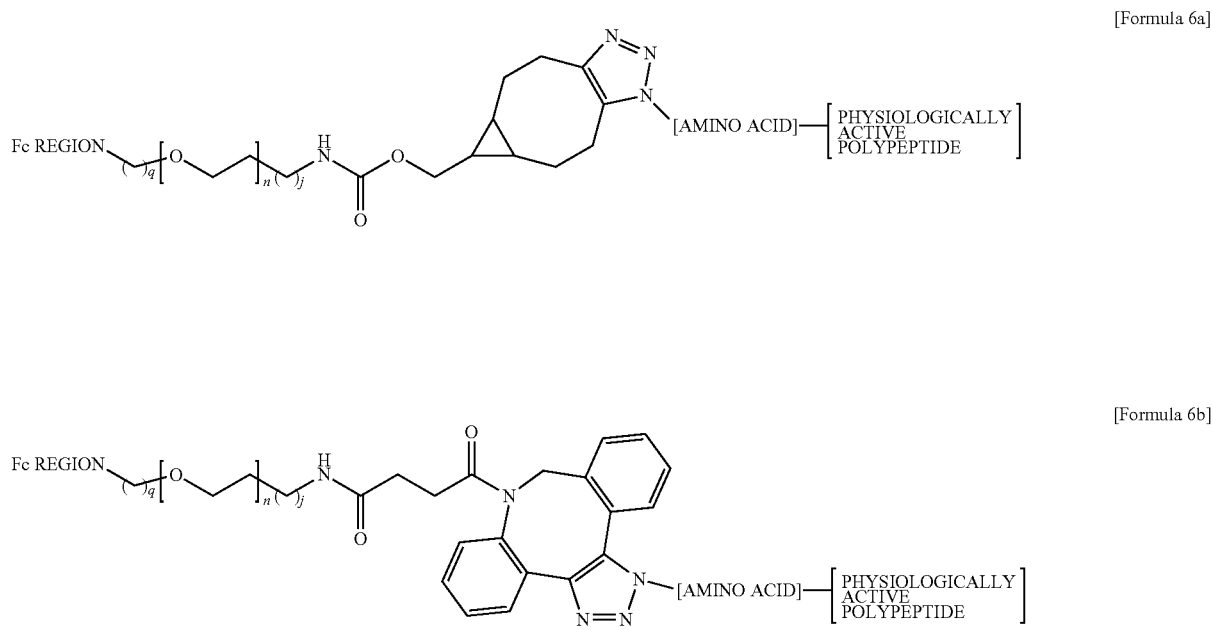

[Formula 6c]
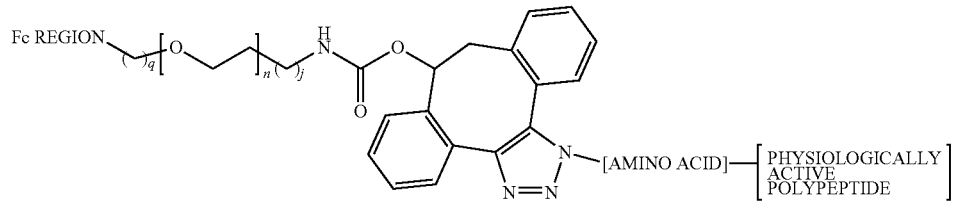
[Formula 6d]
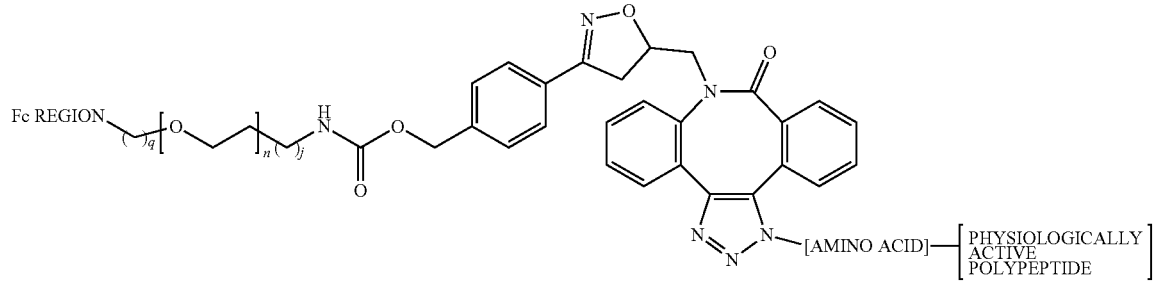
[Formula 6e]
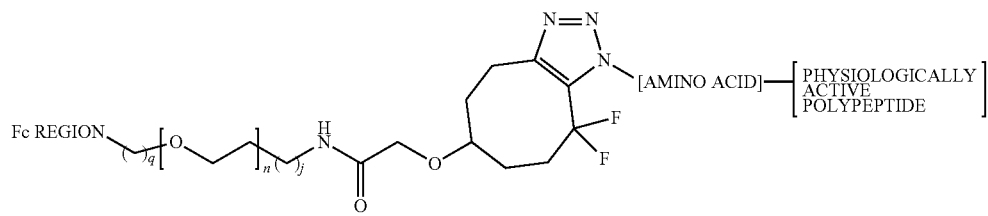
[Formula 6f]
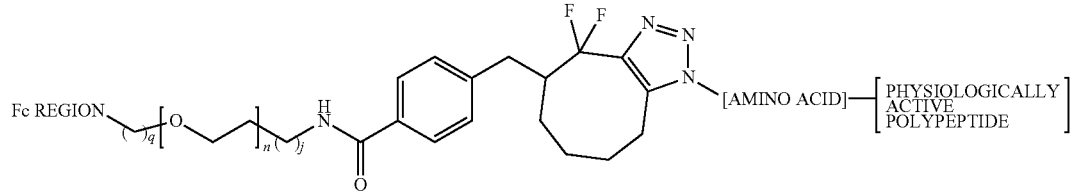
[Formula 6g]
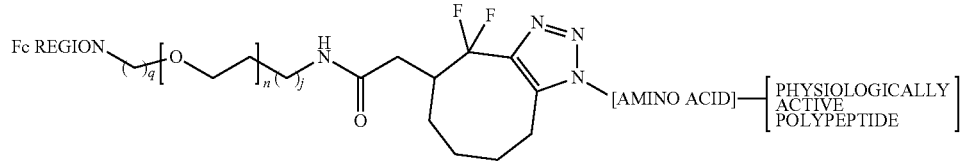
[Formula 6h]
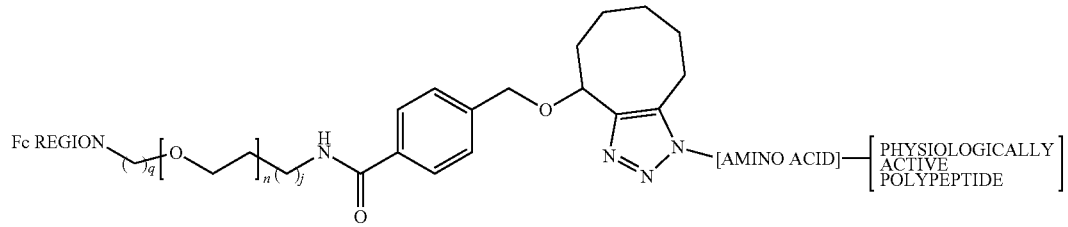
[Formula 6i]
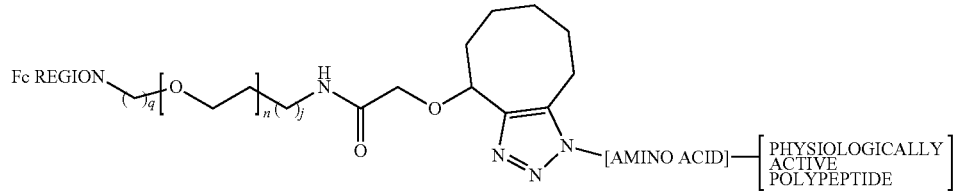

-continued

[Formula 6j]
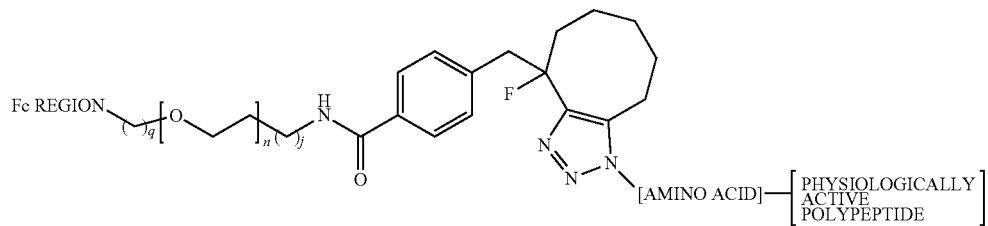

[Formula 6k]
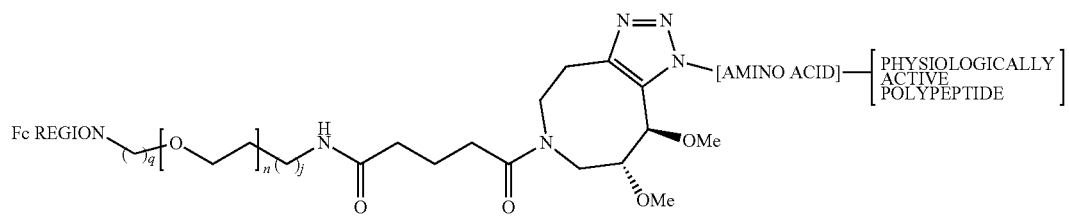

[Formula 6l]
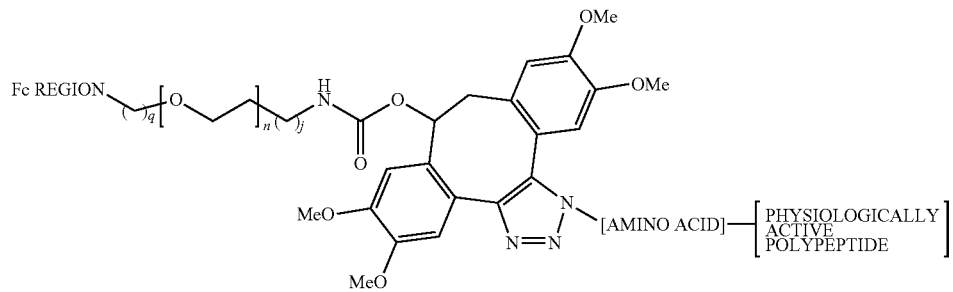

[Formula 6m]
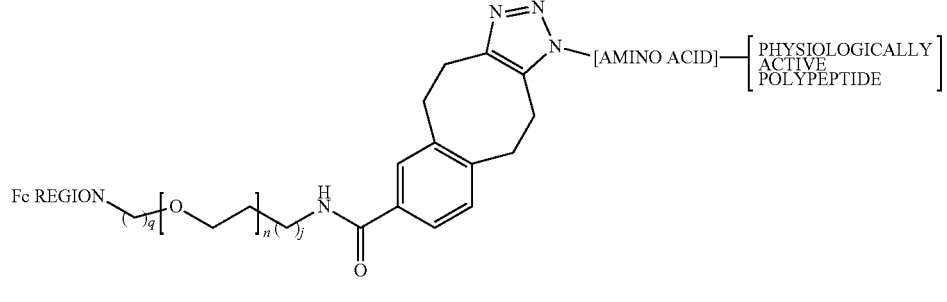

[Formula 6n]
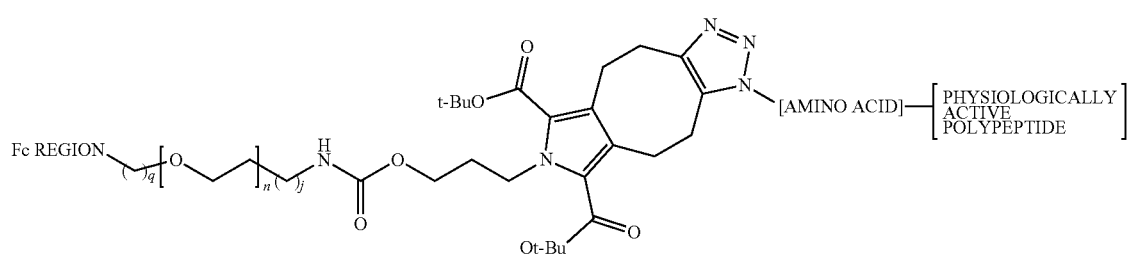

in Formulae 6a to 6n I, j and n are the same as defined in Formula 1a;

[amino acid] is any one of amino acids constituting the physiologically active polypeptide sequence of the natural form, or an added or substituted amino acid that does not belong thereto; and q is an integer of 1 to 6.

In a specific embodiment, [amino acid] of Formulae 6a to 6n is a moiety excluding the epsilon-amino group from the lysine residue of the natural sequence of the physiologically active polypeptide, and triazole nitrogen of Formulae 6a to 6n may be linked to epsilon carbon of the lysine side chain.

In another specific embodiment, [amino acid] of Formulae 6a to 6n is a moiety excluding the alpha-amino group from the N-terminal amino acid of the natural sequence of the physiologically active polypeptide, and triazole nitrogen of Formulae 6a to 6n may be linked to alpha carbon of the N-terminal amino acid.

As used herein, the term "physiologically active polypeptide" refers to any substance having a polypeptide structure exhibiting physiological activity in vivo, in particular, in the human body, and is a concept including precursors, analogs, derivatives, fragments, or variants of a polypeptide having the physiological activity of the corresponding polypeptide.

The physiologically active polypeptide may be selected from the group consisting of hormones, cytokines, enzymes, antibodies, growth factors, transcription regulatory factors, blood factors, vaccines, insulinotropic peptides, neuropeptides, pituitary hormones, anti-obesity peptides, antiviral peptides, physiologically active non-natural peptide derivatives, structural proteins, and receptors, but is not limited thereto.

The physiologically active polypeptide may be, for example, selected from the group consisting of glucagon, gastric inhibitory polypeptide (GIP), xenin, insulin, cholecystokinin (CCK), amylin, gastrin, ghrelin, incretins regulating blood glucose and body weight in stomach or intestine (e.g., peptide YY (PYY)), adipokines secreted by adipose (e.g., leptin, adiponectin, adipolin, apelin, cartonectin), neuropeptides (e.g., Kisspeptin, Nesfatin-1), peptides or proteins secreted by muscles (e.g., irisin, myonectin, decorin, follistatin, musclin), vasoactive intestinal peptides, natriuretic peptide, somatostatin, neuropeptide Y (NPY), glucagon-like peptide-1 (GLP-1), glucagon-like peptide-2 (GLP-2), exendin-4, oxyntomodulin, fibroblast growth factor, angiotensin, bradykinin, calcitonin, adrenocorticotropic hormone (corticotropin), eledoisin, oxytocin, vasopressin, luteinizing hormone, luteotrophic hormone, luteinizing hormone releasing hormone, follicle stimulating hormone, parathyroid hormone, secretin, sermorelin, human growth hormone (hGH), growth hormone-releasing peptides, granulocyte colony-stimulating factors (GCSF), interferons (IFN), interferon receptors, interleukins, interleukin receptors, interleukin-binding proteins, prolactin-releasing peptides, orexin, thyroid-releasing peptides, cholecystokinin, gastrin inhibitory peptides, calmodulin, gastric releasing peptides, motilin, vasoactiveintestinal peptide, atrial natriuretic peptide (ANP), B-type natriuretic peptide (BNP), C-type natriuretic peptide (CNP), neurokinin A, neuromedin, renin, endothelin, sarafotoxin peptide, carsomorphin peptide, dermorphin, dynorphin, endorphin, enkepalin, tumor necrosis factors, tumor necrosis factor receptors, urokinase receptors, tumor inhibitory factors, collagenase inhibitors, thymopoietin, thymulin, thymopentin, tymosin, thymichumoral factor, adrenomodullin, allatostatin, amyloid beta-protein fragment, antibacterial peptides, antioxidant peptides, bombesin, osteocalcin, CART peptides, E-selectin, ICAM-1, VCAM-1, leucokine, kringle-5, laminin, inhibin, galanin, fibronectin, pancreastatin, fuzeon, glucagon-like peptides, oxyntomodulin, G protein-coupled receptor, enzymes, cytokine-binding proteins, macrophage-activating factors, macrophage peptides, B cell factor, T cell factor, protein A, allergy inhibitors, cell necrosis glycoprotein, immunotoxin, lymphotoxin, metastasis-inducing factors, alpha-1-antitrypsin, albumin, α-lactalbumin, apolipoprotein-E, erythropoietin, highly glycosylated erythropoietin, angiopoietins, hemoglobin, thrombin, thrombin receptor-activating peptides, thrombomodulin, blood factors VII, VIIa, VIII, IX, and XIII, plasminogen-activating factors, fibrin-binding peptides, urokinase, streptokinase, hirudin, protein C, C-reactive protein, renin inhibitors, superoxide dismutase, platelet-derived growth factors, epidermal growth factors, epithelial cell growth factors, angiostatin, osteogenic growth factors, osteogenesis-promoting proteins, atriopeptin, cartilage-inducing factors, elcatonin, connective tissue-activating factors, tissue factor pathway inhibitors, nerve growth factor, relaxin, somatomedin, insulin-like growth factor, adrenocortical hormone, pancreatic polypeptides, gastrin-releasing peptides, corticotropin-releasing factor, thyroid-stimulating hormone, autotaxin, lactoferrin, myostatin, cell surface antigens, virus-derived vaccine antigens, monoclonal antibody, polyclonal antibody, antibody fragments, erythropoietin, leukopoietin, and analogs thereof, but is not limited thereto.

In a specific embodiment, the type of the physiologically active polypeptide is not limited, and may include, for example, a triple agonist having activities to all of glucagon, GLP-1, and GIP receptors disclosed in International Patent Publication No. WO 2017-116205 A1; glucagon analogs disclosed in International Patent Publication No. WO 2017-003191 A1, etc.

In a specific embodiment, the physiologically active polypeptide may include GLP-2 analogs. For example, the GLP-2 analogs may include a GLP-2 analog in which a thiol group (e.g., cysteine) is introduced to the C-terminus of natural GLP-2, alanine which is the $2^{nd}$ amino acid is replaced with glycine, and alpha carbon of a histidine residue which is the $1^{st}$ amino acid from the N-terminus is removed; a GLP-2 analog in which an amine group (e.g., lysine) is introduced to the C-terminus of natural GLP-2, alanine which is the $2^{nd}$ amino acid is replaced with glycine, and alpha carbon of a histidine residue which is the $1^{st}$ amino acid from the N-terminus is removed; a GLP-2 analog in which an amine group (e.g., lysine) is introduced to the C-terminus of natural GLP-2, alanine which is the $2^{nd}$ amino acid of natural GLP-2 is replaced with glycine, lysine which is the $30^{th}$ amino acid of natural GLP-2 is replaced with alginine, and alpha carbon of a histidine residue which is the $1^{st}$ amino acid from the N-terminus is removed; a GLP-2 analog in which an azide group (e.g., azidolysine) is introduced to the C-terminus of natural GLP-2, alanine which is the $2^{nd}$ amino acid is replaced with glycine, and alpha carbon of a histidine residue which is the $1^{st}$ amino acid from the N-terminus is removed, etc.

As used herein, the term "immunoglobulin Fc region" refers to a region having a constant sequence excluding a variable region that binds to an antigen and has many sequence variations in an immunoglobulin, and the corresponding portion is characterized to have effector functions such as activation of complement, ability to cross the placenta, or acting as a ligand for receptors of various immune cells. The immunoglobulin Fc region and "immunoglobulin constant region" may be used with the same meaning.

Specifically, the immunoglobulin Fc region refers to a protein that contains the heavy chain constant region 2 (CH2) and the heavy chain constant region 3 (CH3) of an immunoglobulin, excluding the heavy chain and light chain variable regions, the heavy chain constant region 1 (CH1) and the light chain constant region 1 (CL1) of an immunoglobulin. The immunoglobulin Fc region may further include a hinge region in the heavy chain constant region. Further, the immunoglobulin Fc region may be an extended Fc region that contains a portion or the whole of the heavy chain constant region 1 (CH1) and/or the light chain constant region 1 (CL1), except for the heavy chain and light chain variable regions, as long as it has effects substantially equal to or better than the native form. Further, the immunoglobulin Fc region may be a fragment having a deletion in a relatively long portion of the amino acid sequence of CH2 and/or CH3. In other words, the immunoglobulin Fc region may include 1) a CH1 domain, a CH2 domain, a CH3 domain, and a CH4 domain, 2) a CH1 domain and a CH2 domain, 3) a CH1 domain and a CH3 domain, 4) a CH2 domain and a CH3 domain, 5) a combination of one or two or more domains and an immunoglobulin hinge region (or a portion of the hinge region), or 6) a dimer of each domain of the heavy chain constant regions and the light chain constant region.

Further, the immunoglobulin Fc region may include not only a native amino acid sequence, but also a sequence derivative (mutant) thereof. As used herein, the term "amino acid sequence derivative" refers to a sequence that is different from the native amino acid sequence due to a deletion, insertion, non-conservative or conservative substitution or combinations thereof of one or more amino acid residues. For example, in the case of IgG Fc, amino acid residues at positions 214 to 238, 297 to 299, 318 to 322, or 327 to 331, known to be important in binding, may be used as a suitable target for modification.

In addition, various derivatives of the immunoglobulin Fc region are also possible, including derivatives having a deletion of a region capable of forming a disulfide bond, a deletion of several amino acid residues at the N-terminus of a native Fc, or an addition of methionine residue to the N-terminus of a native Fc. Furthermore, to eliminate effector functions, a complement-binding site, for example, a C1q-binding site, may be removed, and an antibody dependent cell mediated cytotoxicity (ADCC) site may also be removed. Techniques of preparing such sequence derivatives of the immunoglobulin Fc region are disclosed in International Patent Publication Nos. WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions. In some case, the immunoglobulin Fc region may also be modified by phosphorylation, sulfation, acrylation, glycosylation, methylation, farnesylation, acetylation, amidation, etc.

The sequence derivatives of the immunoglobulin Fc region are derivatives that exhibit the same biological activity as that of the immunoglobulin Fc region, but have improved structural stability against heat, pH, etc. The Fc immunoglobulin region may be obtained from native forms isolated from humans and animals including cows, goats, pigs, mice, rabbits, hamsters, rats, guinea pigs, etc., or may be recombinant forms or derivatives thereof, obtained from transformed animal cells or microorganisms. Herein, a method of obtaining the Fc immunoglobulin region from a native form may be a method of isolating a whole immunoglobulin from the living body of humans or animals and then treating it with protease. When the whole immunoglobulin is treated with papain, it is cleaved into Fab and Fc, and when it is treated with pepsin, it is cleaved into pF'c and F(ab)2. These fragments may be subjected to size-exclusion chromatography to isolate Fc or pF'c.

In a specific embodiment, the immunoglobulin Fc region may be a recombinant immunoglobulin Fc region obtained from a microorganism by using a human Fc region.

In addition, the immunoglobulin Fc region may be in the form of having native sugar chains, increased sugar chains as compared with a native form, or decreased sugar chains as compared with the native form, or may be in a deglycosylated form. The increase, decrease, or removal of sugar chains of the immunoglobulin Fc region may be performed using common methods, such as a chemical method, an enzymatic method, and a genetic engineering method using a microorganism. Here, the deglycosylated immunoglobulin Fc region may exhibit a sharp decrease in binding affinity for the complement (c1q) and a decrease or loss in antibody-dependent cell-mediated cytotoxicity or complement-dependent cytotoxicity, and thus does not induce unnecessary immune responses in vivo. In this regard, an immunoglobulin Fc region in a deglycosylated or aglycosylated form may be more suitable for use as a drug carrier.

As used herein, the term "deglycosylation" means an immunoglobulin Fc region from which sugar moieties are removed using an enzyme, and the term "aglycosylation" means an unglycosylated immunoglobulin Fc region that is produced in a prokaryote, specifically E. coli.

The immunoglobulin Fc region may originate from humans or animals such as cattle, goats, pigs, mice, rabbits, hamsters, rats, guinea pigs, etc. Specifically, it is of human origin.

In addition, the immunoglobulin Fc region may be an Fc region that is derived from IgG, IgA, IgD, IgE, IgM, or combinations thereof, or hybrids thereof. Specifically, it is derived from IgG or IgM, which is the most abundant proteins in the human blood, and most specifically, it is derived from IgG known to enhance the half-life of binding proteins.

As used herein, the term "combination" means that polypeptides encoding single-chain immunoglobulin Fc regions of the same origin are linked to a single-chain polypeptide of a different origin to form a dimer or multimer. In other words, a dimer or multimer may be formed from two or more fragments selected from the group consisting of IgG Fc, IgA Fc, IgM Fc, IgD Fc and IgE Fc fragments.

As used herein, the term "hybrid" means that sequences encoding two or more immunoglobulin Fc fragments of different origins are present in a single-chain immunoglobulin Fc region. Various types of hybrids are possible. In other words, domain hybrids may be composed of one to four domains selected from the group consisting of CH1, CH2, CH3 and CH4 of IgG Fc, IgM Fc, IgA Fc, IgE Fc, and IgD Fc, and optionally, may include a hinge region.

IgG may be divided into IgG1, IgG2, IgG3, and IgG4 subclasses, and combinations or hybrids thereof may be used as the immunoglobulin Fc region. The immunoglobulin Fc region is specifically IgG2 and IgG4 subclasses, and most specifically, the Fc fragment of IgG4 rarely having effector functions such as complement dependent cytotoxicity (CDC).

In a specific embodiment, the immunoglobulin Fc region may be a human IgG4-derived aglycosylated Fc region. The human-derived Fc region is suitable, as compared with a non-human Fc region which may act as an antigen in the human body and cause undesirable immune responses such as the production of a new antibody against the antigen.

Still another aspect of the present disclosure provides a method of preparing the physiologically active polypeptide conjugate in which the physiologically active polypeptide and the immunoglobulin Fc region are linked to each other via the compound of Formula 1 as a linker, the method including:

introducing the azide group to the physiologically active polypeptide;

forming 1,2,3-triazole by cycloaddition through click reaction of the azide group and the ethynylene group (—C≡C—) of R2 of the compound of the following Formula 1; and covalently linking an amino acid of the immunoglobulin Fc region with R1 of the compound of Formula 1.

R1-non-peptidyl polymer-X—R2     [Formula 1]

in Formula 1,

R1 is an aliphatic hydrocarbon group including a functional group selected from the group consisting of 2,5-dioxopyrrolidinyl, 2,5-dioxopyrrolyl, aldehyde, maleimide, $C_6$-$C_{20}$ aryl disulfide, $C_5$-$C_{20}$ heteroaryl disulfide, vinyl sulfone, thiol, halogenated acetamide, succinimide, p-nitrophenyl carbonate, and derivatives thereof;

X is —$(CH_2)_j$NHCO— or —$(CH_2)_j$NHCS—, wherein j is an integer of 0 to 6;

R2 is —$(R3)_k$-$(Z)_l$—$(R4)_m$-$(CZ)_p$—Y, wherein R3 and R4 are each independently $C_1$-$C_6$ alkylene, $C_6$-$C_{20}$ arylene, or $C_5$-$C_{20}$ heteroarylene having 1 to 3 heteroatoms selected from N, O, and S, Z is O or S, Y is $C_2$-$C_6$ alkynyl, cycloalkynyl, bicycloalkynyl, arylcycloalkynyl, diarylcycloalkynyl, heterocycloalkynyl, or diarylheterocycloalkynyl (wherein each cycloalkynyl has 3 to 8 carbon atoms, each aryl has 5 to 8 carbon atoms, and each heterocycloalkynyl is a saturated ring including 3 to 8 atoms and having heteroatoms selected from N, O, and S in 1 to 3 of ring atoms), k, l, m, and p are each independently an integer of 0 to 3, provided that all of them may not be 0 at the same time, and the alkynyl, cycloalkynyl, bicycloalkynyl, arylcycloalkynyl, diarylcycloalkynyl, heterocycloalkynyl, or diarylheterocycloalkynyl may be substituted or unsubstituted with $C_1$-$C_6$ alkyl, $C_1$-$C_6$ alkoxy, $C_1$-$C_6$ alkoxycarbonyl, oxo, or halogen.

The above description of the physiologically active polypeptide conjugate according to an aspect of the present disclosure may be applied as it is to the preparation method.

A method of introducing the azide group to the physiologically active polypeptide may be performed according to a method known in the organic chemistry field.

In a specific embodiment, the amino acid at the C-terminus of the physiologically active polypeptide may be replaced with lysine, and the azide group may be introduced to the replaced lysine position.

In a specific embodiment, azidolysine ($N_3$-lysine) may be linked to the C-terminus of the physiologically active polypeptide.

The cycloaddition through click reaction of the azide group and the ethynylene group of R2 of the compound of the following Formula 1 may be performed according to Copper(I)-Catalyzed Azide-Alkyne Cycloaddition (CuAAC) or Strain-promoted Azide-Alkyne Cycloaddition (SPAAC) widely known in the organic chemistry field, depending on the structure of R2. When Y of R2 is $C_2$-$C_6$ alkynyl, click reaction may be carried out according to CuAAC in the presence of a monovalent copper catalyst, and when Y of R2 has a ring structure such as cycloalkynyl, arylcycloalkynyl, heterocycloalkynyl, arylheterocycloalkynyl, diarylcycloalkynyl, diarylheterocycloalkynyl, etc., cycloaddition may be performed according to SPAAC in the absence of a monovalent copper catalyst.

In the click reaction of the azide group of the physiologically active polypeptide and the ethynylene group of R2 of the compound of Formula 1, a reaction molar ratio of the physiologically active polypeptide and the compound of Formula 1 may be selected from the range of 1:1 to 1:20, but is not limited thereto. In a specific embodiment, the reaction molar ratio of the physiologically active polypeptide and the compound of Formula 1 may be 1:2 to 1:20.

In the covalent linking of the amino acid of the immunoglobulin Fc region with R1 of the compound of Formula 1, R1 which is an aliphatic hydrocarbon group including a functional group selected from the group consisting of 2,5-dioxopyrrolidinyl, 2,5-dioxopyrrolyl, aldehyde, maleimide, $C_6$-$C_{20}$ aryl disulfide, $C_5$-$C_{20}$heteroaryl disulfide, vinyl sulfone, thiol, halogenated acetamide, succinimide, p-nitrophenyl carbonate, and derivatives thereof may be covalently linked to a functional group such as an amine group, an amino group, or a thiol group of the N-terminal amino acid of the immunoglobulin Fc region. In a specific embodiment, the amine group or amino group of the amino acid of the immunoglobulin Fc region may be covalently linked to R1 including an aldehyde functional group by reductive amination. In a specific embodiment, the N-terminal amino acid of the immunoglobulin Fc region may be covalently linked to R1 of the compound of Formula 1.

In the covalent linking of the amino acid of the immunoglobulin Fc region with R1 of the compound of Formula 1, a reaction molar ratio of the compound of Formula 1 linked with the physiologically active polypeptide and the immunoglobulin Fc may be selected from the range of 1:1 to 1:20, but is not limited thereto. In a specific embodiment, the reaction molar ratio of the compound of Formula 1 linked with the physiologically active polypeptide and the immunoglobulin Fc may be 1:2 to 1:20.

Still another aspect of the present disclosure provides a method of using a compound selected from the compound of Formula 1, a stereoisomer thereof, a solvate thereof, and a pharmaceutically acceptable salt thereof in the preparation of the physiologically active polypeptide linkage. In other words, provided is use of the compound of Formula 1, etc. in the preparation of physiologically active polypeptide linkage.

Still another aspect of the present disclosure provides a method of using a compound selected from the compound of Formula 1, a stereoisomer thereof, a solvate thereof, and a pharmaceutically acceptable salt thereof in the preparation of the physiologically active polypeptide conjugate. In other words, provided is use of the compound of Formula 1, etc. as a linker in the preparation of physiologically active polypeptide conjugate.

Hereinafter, the present disclosure will be described in more detail with reference to exemplary embodiments. However, these exemplary embodiments are for illustrative purposes only, and the scope of the present disclosure is not limited to these exemplary embodiments.

EXAMPLE 1

Preparation of Linker Compound (1)

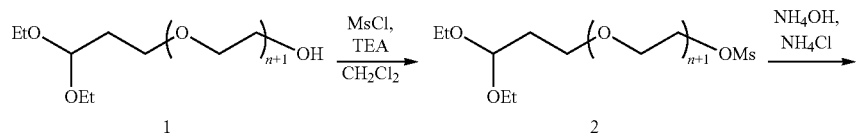

-continued

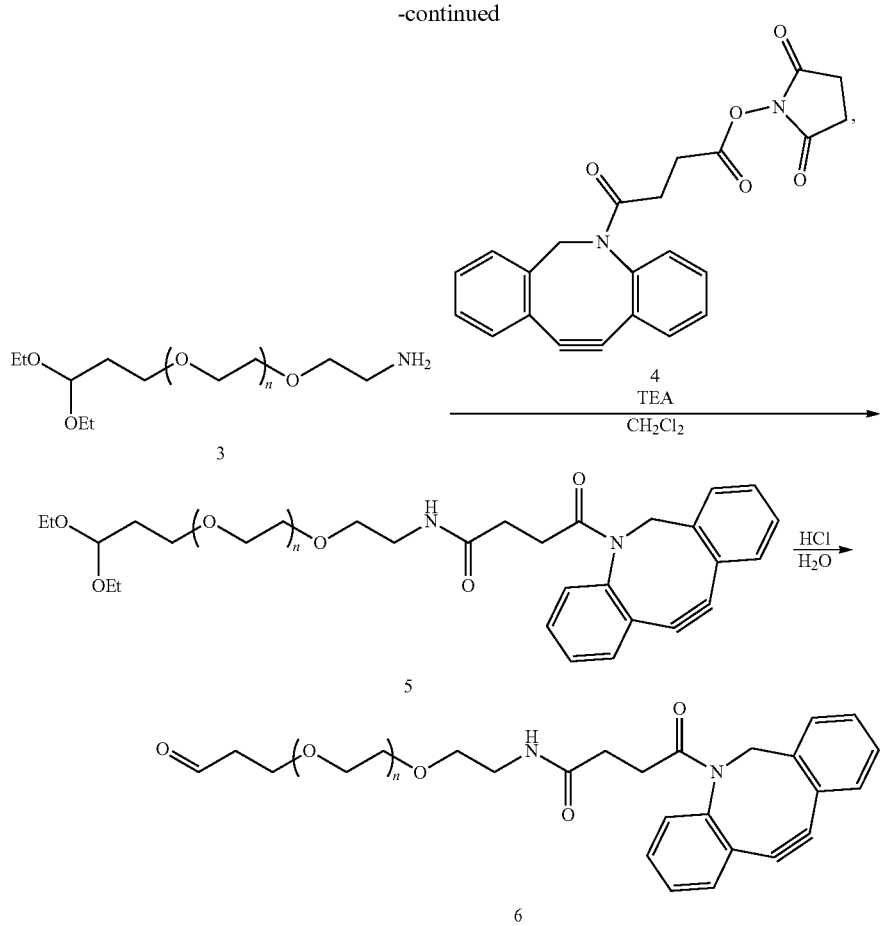

1-1: Preparation of Compound 2 (MW=10000)

20 g of compound 1 (MW=10000) and 60 mL of dichloromethane were introduced into a reactor. 1.11 g of triethylamine and 1.15 g of methanesulfonyl chloride were added thereto while maintaining a reaction temperature at 10° C. or less, followed by stirring at room temperature for 3 hours. After completing the reaction, 100 mL of water and 40 mL of dichloromethane were introduced, followed by stirring for 5 minutes. The obtained organic layer was separated, and then 100 mL of dichloromethane was added to an aqueous layer for further extraction. The organic layer was collected and washed with 100 mL of water, and dried over magnesium sulfate. Filtration was performed, and a remaining filtrate was distilled under reduced pressure. 20 mL of dichloromethane was added to the concentrate, which was then dissolved, and 300 mL of methyl t-butyl ether was added dropwise for 20 minutes. Resulting crystals were filtered and washed with methyl t-butyl ether, and then dried at room temperature under nitrogen to obtain 17.2 g of a compound (2) (MW=10000) which is a title compound.

1-2: Preparation of Compound 3 (MW=10000)

200 mL of an ammonia aqueous solution and 20 g of ammonium chloride were introduced into a reactor. 10 g of the compound 2 (MW=10000) was added, followed by stirring at room temperature for 4 days. After completing the reaction, 200 mL of dichloromethane was introduced, followed by stirring for 5 minutes. The obtained organic layer was separated, and then 200 mL of dichloromethane was added to an aqueous layer for further extraction. The organic layer was collected and washed with 200 mL of water, and dried over magnesium sulfate. Filtration was performed, and a remaining filtrate was distilled under reduced pressure. 10 mL of dichloromethane was added to the concentrate, which was then dissolved, and 150 mL of methyl t-butyl ether was added dropwise for 20 minutes. Resulting crystals were filtered and washed with methyl t-butyl ether, and then dried at room temperature under nitrogen to obtain 8.5 g of a compound (3) (MW=10000) which is a title compound.

1-3: Preparation of Compound 5 (MW=10000)

1.66 g of the compound 3 (MW=10000) and 17 mL of dichloromethane were introduced into a reactor. 200 mg of compound 4 and 50 mg of triethylamine were added, followed by stirring at room temperature for 3 hours. After completing the reaction, the solvent was distilled under reduced pressure and 35 mL of water was introduced to dissolve the product. Ethyl acetate (35 mL×3) was introduced and stirred for 5 minutes, and then an aqueous layer was separated and extracted twice using 35 mL of dichloromethane. The obtained organic layer was dried over magnesium sulfate. Filtration was performed, followed by distillation under reduced pressure. 2 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 1.0 g of a compound (5) (MW=10000) which is a title compound.

1-4: Preparation of Compound 6 (MW=10000)

0.8 g of compound 5 (MW=10000) and 14.4 mL of distilled water were introduced into a reactor. 1.6 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 20 mL of dichloromethane. The resultant was dried over magnesium sulfate, and filtered and distilled under reduced pressure. 1 mL of dichloromethane was added to the concentrate, which was then dissolved, and 15 mL of methyl t-butyl ether was added dropwise for 20 minutes. Resulting crystals were filtered and washed with methyl t-butyl ether, and then dried under nitrogen to obtain 498 mg of a compound (6) (MW=10000) which is a title compound. The compound 6 (MW=10000) was designated as ALD-PEG 10K-DBCO. FIG. 1 shows $^1$H NMR result of the linker compound 6 (MW=10000). $^1$H NMR (CDCl$_3$, 400 MHz) δ 9.78 (s, 1H), 7.65 (d, 1H), 7.51 (d, 1H), 7.38-7.25 (m, 6H), 6.11 (br s, 1H), 5.14 (d, 1H), 3.85-3.43 (m, 915H), 3.31 (m, 2H), 2.80 (m, 1H), 2.67 (t, 2H), 2.45 (m, 1H), 2.15 (m, 1H), 1.93 (m, 1H).

EXAMPLE 2

Preparation of Linker Compound (2)

2-1: Preparation of Compound 2 (MW=5000)

20 g of the compound 1 (MW=5000) and 60 mL of dichloromethane were introduced into a reactor. 2.23 g of triethylamine and 2.29 g of methanesulfonyl chloride were added thereto while maintaining a reaction temperature at 10° C. or less, followed by stirring at room temperature for 3 hours. After completing the reaction, 100 mL of water and 40 mL of dichloromethane were introduced, followed by stirring for 5 minutes. The obtained organic layer was separated, and then 100 mL of dichloromethane was added to an aqueous layer for further extraction. The organic layer was collected and washed with 100 mL of water, and dried over magnesium sulfate. Filtration was performed, and a remaining filtrate was distilled under reduced pressure. 20 mL of dichloromethane was added to the concentrate, which was then dissolved, and 300 mL of methyl t-butyl ether was added dropwise for 20 minutes. Resulting crystals were filtered and washed with methyl t-butyl ether, and then dried at room temperature under nitrogen to obtain 16.2 g of a compound (2) (MW=5000) which is a title compound.

2-2: Preparation of Compound 3 (MW=5000)

200 mL of an ammonia aqueous solution and 20 g of ammonium chloride were introduced into a reactor. 10 g of compound 2 (MW=5000) was added, followed by stirring at room temperature for 4 days. After completing the reaction, 200 mL of dichloromethane was introduced, followed by stirring for 5 minutes. The obtained organic layer was separated, and then 200 mL of dichloromethane was added to an aqueous layer for further extraction. The organic layer was collected and washed with 200 mL of water, and dried over magnesium sulfate. Filtration was performed, and a remaining filtrate was distilled under reduced pressure. 10 mL of dichloromethane was added to the concentrate, which was then dissolved, and 150 mL of methyl t-butyl ether was added dropwise for 20 minutes. Resulting crystals were filtered and washed with methyl t-butyl ether, and then dried at room temperature under nitrogen to obtain 8.1 g of a compound (3) (MW=5000) which is a title compound.

2-3: Preparation of Compound 5 (MW=5000)

2 g of the compound 3 (MW=5000) and 20 mL of dichloromethane were introduced into a reactor. 483 mg of the compound 4 and 122 mg of triethylamine were added, followed by stirring at room temperature for 3 hours. After completing the reaction, the solvent was distilled under reduced pressure and 30 mL of water was introduced to dissolve the product. Ethyl acetate (35 mL×3) was introduced and stirred for 5 minutes, and then an aqueous layer was separated and extracted twice using 30 mL of dichloromethane. The obtained organic layer was dried over magnesium sulfate. Filtration was performed, followed by distillation under reduced pressure. 2 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 1.2 g of a compound (5) (MW=5000) which is a title compound.

2-4: Preparation of Compound 6 (MW=5000)

Figure 2:
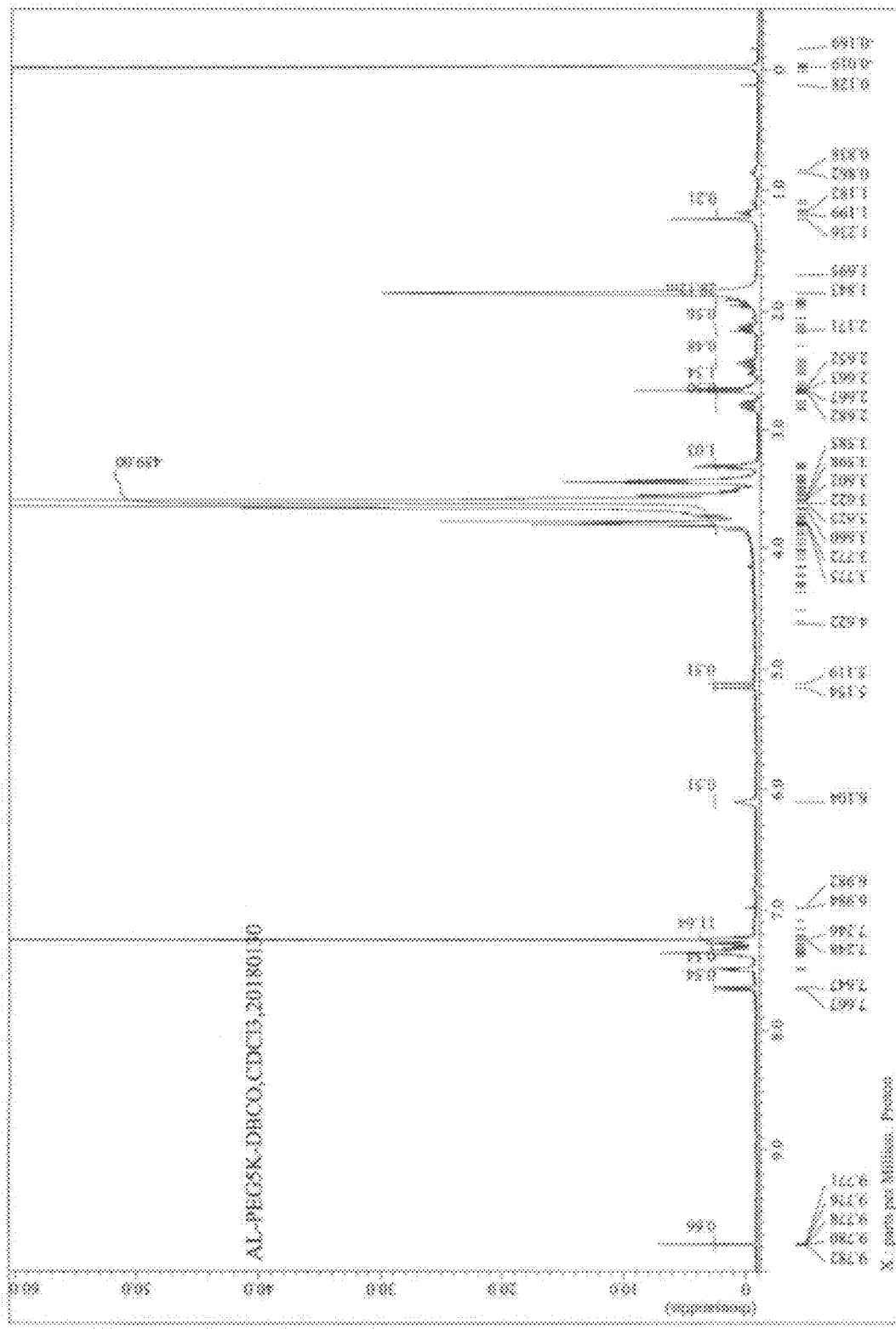
FIG. 2 shows $^1$H NMR result of a linker compound 6 (MW=5000) according to an embodiment.

0.8 g of the compound 5 (MW=10000) and 14.4 mL of distilled water were introduced into a reactor. 1.6 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 20 mL of dichloromethane. The resultant was dried over magnesium sulfate, and filtered and distilled under reduced pressure. 1 mL of dichloromethane was added to the concentrate, which was then dissolved, and 15 mL of methyl t-butyl ether was added dropwise for 20 minutes. Resulting crystals were filtered and washed with methyl t-butyl ether, and then dried under nitrogen to obtain 500 mg of a compound (6) (MW=5000) which is a title compound. The compound 6 (MW=5000) was designated as ALD-PEG 5K-DBCO. FIG. 2 shows $^1$H NMR result of the linker compound 6 (MW=5000). $^1$H NMR (CDCl$_3$, 400 MHz) δ 9.78 (s, 1H), 7.66 (d, 1H), 7.50 (d, 1H), 7.40-7.25 (m, 6H), 6.10 (br s, 1 H), 5.13 (d, 1 H), 3.82-3.41 (m, 459H), 3.32 (m, 2H), 2.80 (m, 1H), 2.67 (t, 2H), 2.45 (m, 1H), 2.16 (m, 1H), 1.92 (m, 1H).

EXAMPLE 3

Preparation of Linker Compound (3)

3-1: Preparation of Compound 2 (MW=3400)

20 g of compound 1 (MW=3400) and 60 mL of dichloromethane were introduced into a reactor. 3.27 g of triethylamine and 3.37 g of methanesulfonyl chloride were added thereto while maintaining a reaction temperature at 10° C. or less, followed by stirring at room temperature for 3 hours. After completing the reaction, 100 mL of water and 40 mL of dichloromethane were introduced, followed by stirring for 5 minutes. The obtained organic layer was separated, and then 100 mL of dichloromethane was added to an aqueous layer for further extraction. The organic layer was collected and washed with 100 mL of water, and dried over magnesium sulfate. Filtration was performed, and a remaining filtrate was distilled under reduced pressure. 40 mL of dichloromethane was added to the concentrate, which was then dissolved, and 400 mL of methyl t-butyl ether was added dropwise for 20 minutes. Resulting crystals were filtered and washed with methyl t-butyl ether, and then dried at room temperature under nitrogen to obtain 17.1 g of a compound (2) (MW=3400) which is a title compound.

3-2: Preparation of Compound 3 (MW=3400)

200 mL of an ammonia aqueous solution and 20 g of ammonium chloride were introduced into a reactor. 10 g of the compound 2 (MW=3400) was added, followed by stirring at room temperature for 4 days. After completing the reaction, 200 mL of dichloromethane was introduced, followed by stirring for 5 minutes. The obtained organic layer was separated, and then 200 mL of dichloromethane was added to an aqueous layer for further extraction. The organic layer was collected and washed with 200 mL of water, and dried over magnesium sulfate. Filtration was performed, and a remaining filtrate was distilled under reduced pressure. 20 mL of dichloromethane was added to the concentrate, which was then dissolved, and 200 mL of methyl t-butyl ether was added dropwise for 20 minutes. Resulting crystals were filtered and washed with methyl t-butyl ether, and then dried at room temperature under nitrogen to obtain 8.7 g of a compound (3) (MW=3400) which is a title compound.

3-3: Preparation of Compound 5 (MW=3400)

1.7 g of the compound 3 (MW=3400) and 17 mL of dichloromethane were introduced into a reactor. 604 mg of compound 4 and 152 mg of triethylamine were added, followed by stirring at room temperature for 3 hours. After completing the reaction, the solvent was distilled under reduced pressure and 35 mL of water was introduced to dissolve the product. Ethyl acetate (35 mL×3) was introduced and stirred for 5 minutes, and then an aqueous layer was separated and extracted twice using 35 mL of dichloromethane. The obtained organic layer was dried over magnesium sulfate. Filtration was performed, followed by distillation under reduced pressure. 3.5 mL of dichloromethane was added to the concentrate, which was then dissolved, and 35 mL of methyl t-butyl ether was added dropwise for 20 minutes. Resulting crystals were filtered and washed with methyl t-butyl ether, and then dried under nitrogen to obtain 1.1 g of a compound (5) (MW=3400) which is a title compound.

3-4: Preparation of Compound 6 (MW=3400)

Figure 3:
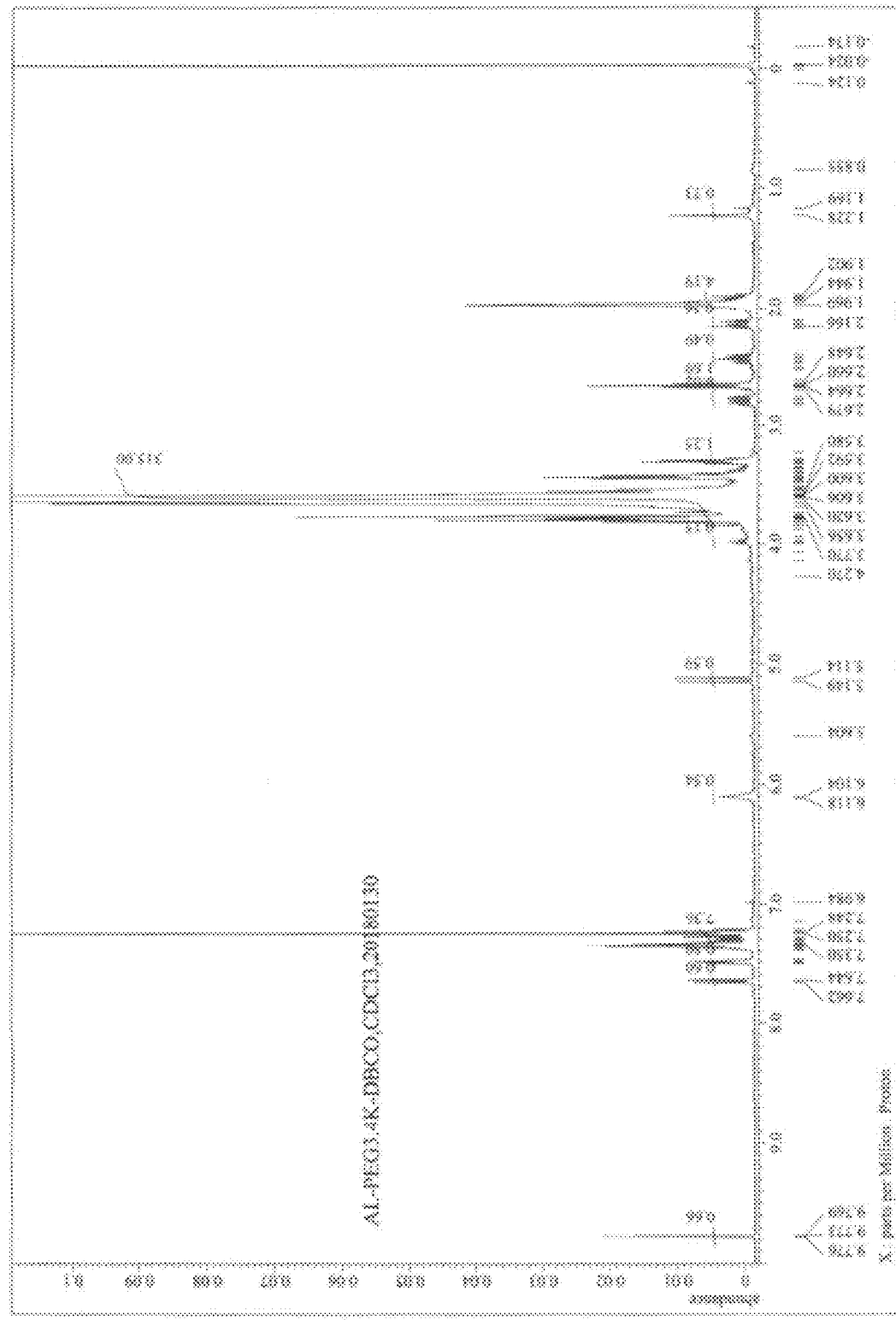
FIG. 3 shows $^1$H NMR result of a linker compound 6 (MW=3400) according to an embodiment.

0.9 g of the compound 5 (MW=10000) and 16.2 mL of distilled water were introduced into a reactor. 1.8 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 20 mL of dichloromethane. The resultant was dried over magnesium sulfate, and filtered and distilled under reduced pressure. 2 mL of dichloromethane was added to the concentrate, which was then dissolved, and 20 mL of methyl t-butyl ether was added dropwise for 20 minutes. Resulting crystals were filtered and washed with methyl t-butyl ether, and then dried under nitrogen to obtain 590 mg of a compound (6) (MW=3400) which is a title compound. The compound 6 (MW=5000) was designated as ALD-PEG 3.4K-DBCO. FIG. 3 shows $^1$H NMR result of the linker compound 6 (MW=3400). $^1$H NMR (CDCl$_3$, 400 MHz) δ 9.77 (s, 1H), 7.65 (d, 1H), 7.50 (d, 1H), 7.38-7.24 (m, 6H), 6.11 (br s, 1 H), 5.13 (d, 1 H), 3.80-3.39 (m, 315H), 3.32 (m, 2H), 2.80 (m, 1H), 2.66 (t, 2H), 2.44 (m, 1H), 2.15 (m, 1H), 1.92 (m, 1H).

EXAMPLE 4

Preparation of Linker Compound (4)

4-1: Preparation of Compound 2 (MW=2000)

29.3 g of the compound 1 (MW=2000) and 90 mL of dichloromethane were introduced into a reactor. 8.2 g of triethylamine and 8.4 g of methanesulfonyl chloride were added thereto while maintaining a reaction temperature at 10° C. or less, followed by stirring at room temperature for 3 hours. After completing the reaction, 150 mL of water and 60 mL of dichloromethane were introduced, followed by stirring for 5 minutes. The obtained organic layer was separated, and then 150 mL of dichloromethane was added to an aqueous layer for further extraction. The organic layer was collected and washed with 150 mL of water, and dried over magnesium sulfate. Filtration was performed, and a remaining filtrate was distilled under reduced pressure. 30 mL of dichloromethane was added to the concentrate, which was then dissolved, and 900 mL of methyl t-butyl ether was added dropwise for 20 minutes. Resulting crystals were filtered and washed with methyl t-butyl ether, and then dried at room temperature under nitrogen to obtain 23.0 g of a compound (2) (MW=2000) which is a title compound.

4-2: Preparation of Compound 3 (MW=2000)

200 mL of an ammonia aqueous solution and 20 g of ammonium chloride were introduced into a reactor. 10 g of the compound 2 (MW=2000) was added, followed by stirring at room temperature for 4 days. After completing the reaction, 200 mL of dichloromethane was introduced, followed by stirring for 5 minutes. The obtained organic layer was separated, and then 200 mL of dichloromethane was added to an aqueous layer for further extraction. The organic layer was collected and washed with 200 mL of distilled water, and dried over magnesium sulfate. Filtration was performed, and a remaining filtrate was distilled under reduced pressure. 10 mL of dichloromethane was added to the concentrate, which was then dissolved, and 300 mL of methyl t-butyl ether was added dropwise for 20 minutes. Resulting crystals were filtered and washed with methyl t-butyl ether, and then dried at room temperature under nitrogen to obtain 8.1 g of a compound (3) (MW=2000) which is a title compound.

4-3: Preparation of Compound 5 (MW=2000)

1.5 g of the compound 3 (MW=2000) and 15 mL of dichloromethane were introduced into a reactor. 905 mg of the compound 4 and 228 mg of triethylamine were added, followed by stirring at room temperature for 3 hours. After completing the reaction, the solvent was distilled under reduced pressure and 30 mL of water was introduced to dissolve the product. Ethyl acetate (30 mL×3) was introduced and stirred for 5 minutes, and then an aqueous layer was separated and extracted twice using 30 mL of dichloromethane. The obtained organic layer was dried over magnesium sulfate. Filtration was performed, followed by distillation under reduced pressure. 2 mL of dichloromethane was added to the concentrate, which was then dissolved, and 60 mL of methyl t-butyl ether was added dropwise for 20 minutes. Resulting crystals were filtered and washed with methyl t-butyl ether, and then dried under nitrogen to obtain 1.0 g of a compound (5) (MW=2000) which is a title compound.

4-4: Preparation of Compound 6 (MW=2000)

Figure 4:
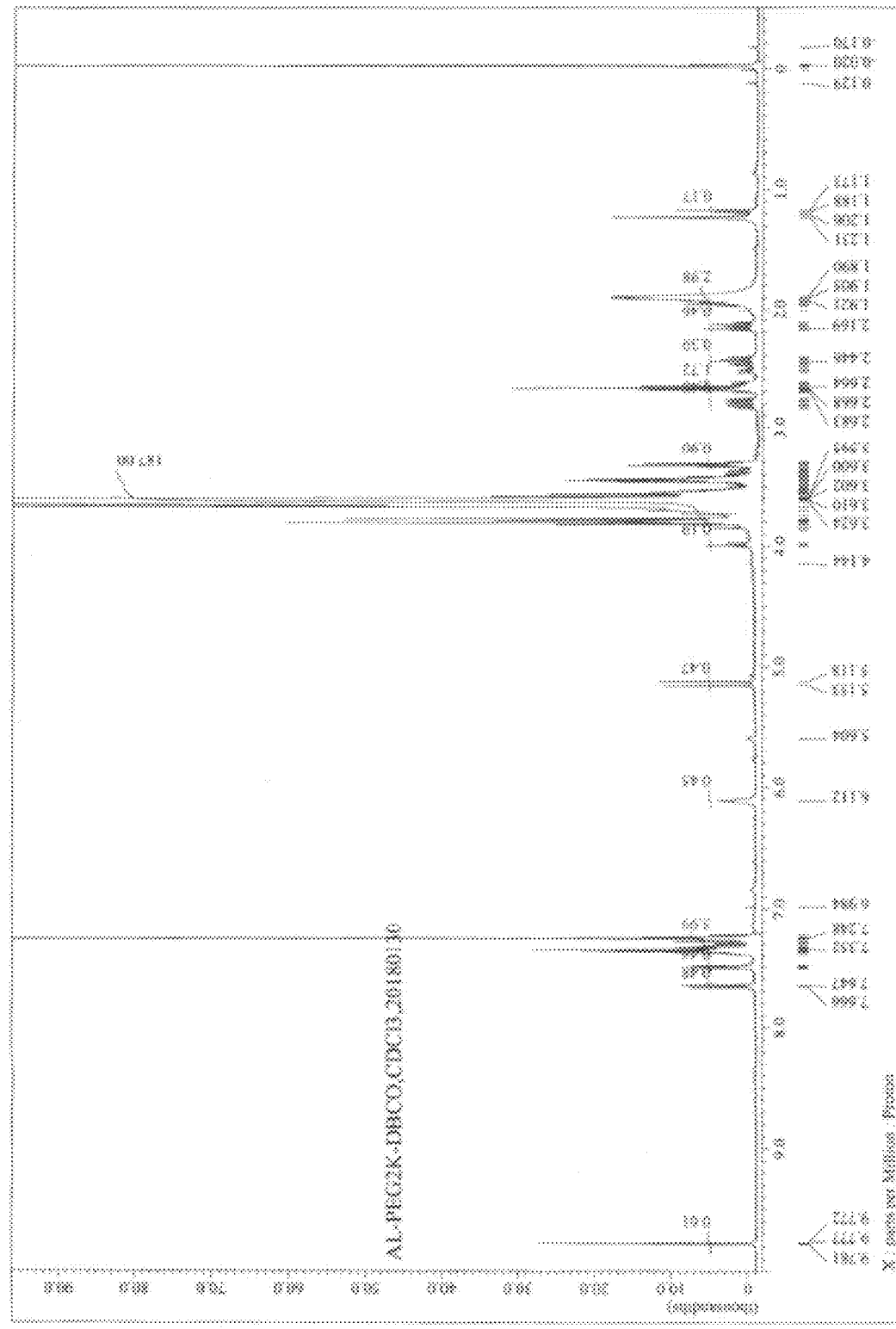
FIG. 4 shows $^1$H NMR result of a linker compound 6 (MW=2000) according to an embodiment.

0.65 g of the compound 5 (MW=10000) and 12.6 mL of distilled water were introduced into a reactor. 1.6 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 20 mL of dichloromethane. The resultant was dried over magnesium sulfate, and filtered and distilled under reduced pressure. 1 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 140 mg of a compound (6) (MW=2000) which is a title compound. The compound 6 (MW=2000) was designated as ALD-PEG 2K-DBCO. FIG. 4 shows $^1$H NMR result of the linker compound 6 (MW=2000). $^1$H NMR (CDCl$_3$, 400 MHz) δ 9.78 (s, 1H), 7.65 (d, 1H), 7.51 (d, 1H), 7.38-7.24 (m, 6H), 6.11 (br s, 1 H), 5.13 (d, 1 H), 3.82-3.37 (m, 187H), 3.32 (m, 2H), 2.67 (m, 1H), 2.67 (t, 2H), 2.45 (m, 1H), 2.15 (m, 1H), 1.93 (m, 1H).

EXAMPLE 5

Preparation of Linker Compound (5)

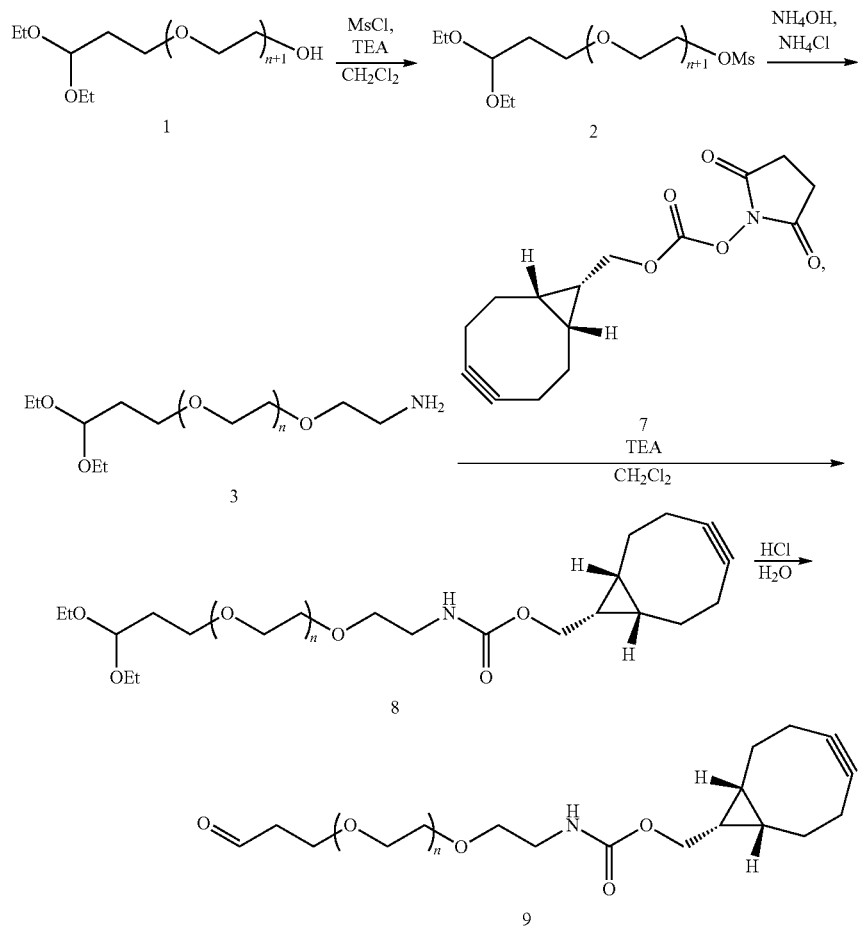

5-1: Preparation of Compound 2 (MW=10000)

A compound 2 (MW=10000) was obtained in the same manner as in Example 1-1.

5-2: Preparation of Compound 3 (MW=10000)

A compound 3 (MW=10000) was obtained in the same manner as in Example 1-2.

5-3: Preparation of Compound 8 (MW=10000)

1.76 g of the compound 3 (MW=10000) and 17 mL of dichloromethane were introduced into a reactor. 154 mg of the compound 7 and 54 mg of triethylamine were added, followed by stirring at room temperature for 3 hours. After completing the reaction, the solvent was distilled under reduced pressure and 35 mL of distilled water was introduced to dissolve the product. Ethyl acetate (35 mL×3) was introduced and stirred for 5 minutes, and then an aqueous layer was separated and extracted twice using 35 mL of dichloromethane. The obtained organic layer was dried over magnesium sulfate. Filtration was performed, followed by distillation under reduced pressure. 2 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 1.0 g of a compound (8) (MW=10000) which is a title compound.

5-4: Preparation of Compound 9 (MW=10000)

Figure 5:
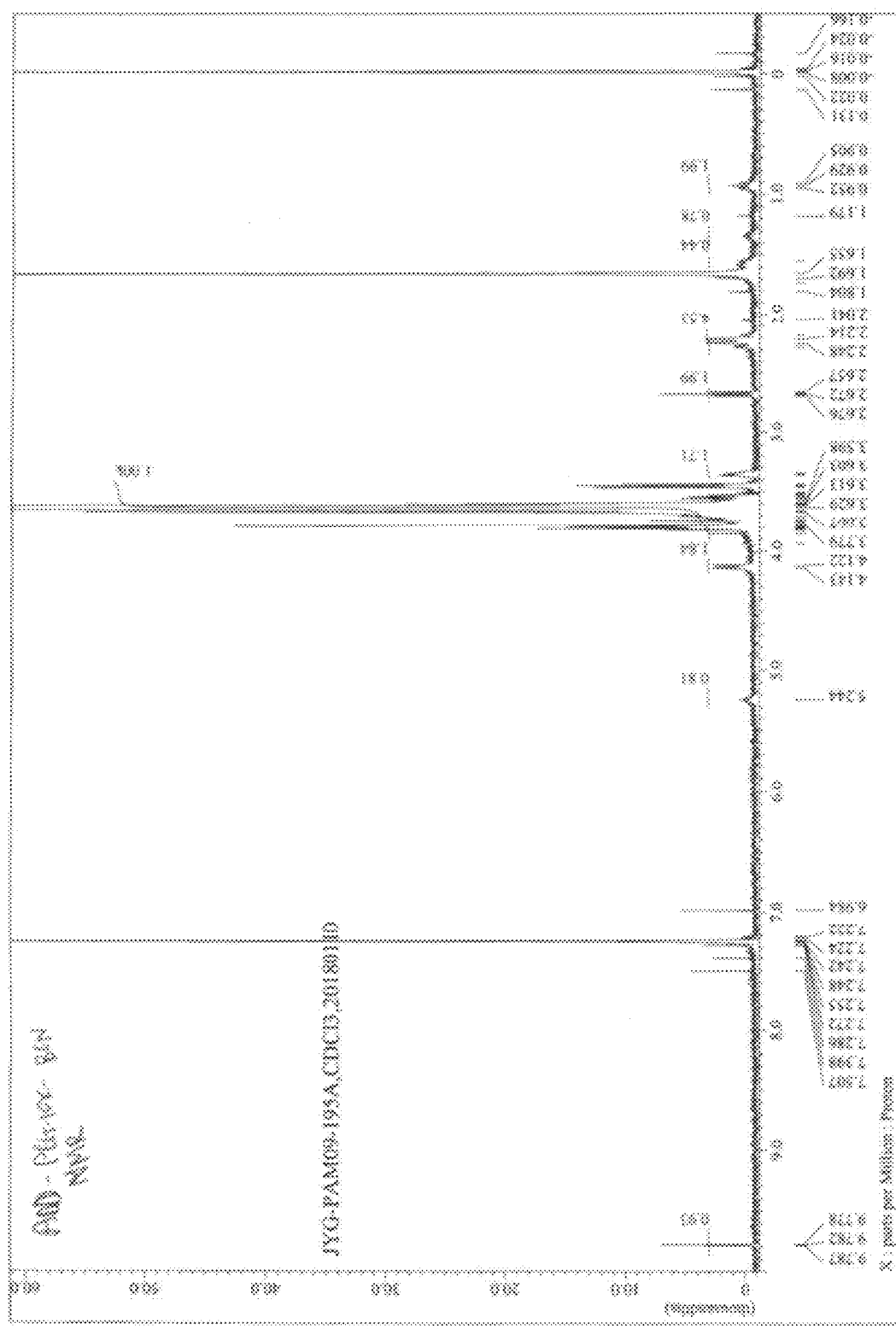
FIG. 5 shows $^1$H NMR result of a linker compound 9 (MW=10000) according to an embodiment.

0.4 g of the compound 5 (MW=10000) and 7.2 mL of distilled water were introduced into a reactor. 0.8 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 10 mL of dichloromethane. The resultant was dried over magnesium sulfate, and filtered and distilled under reduced pressure. 1 mL of dichloromethane was added to the concentrate, which was then dissolved, and 15 mL of methyl t-butyl ether was added dropwise for 20 minutes. Resulting crystals were filtered and washed with methyl t-butyl ether, and then dried under nitrogen to obtain 260 mg of a compound (9) (MW=10000) which is a title compound. The compound 9 (MW=10000) was designated as ALD-PEG 10K-BCN. FIG. 5 shows $^1$H NMR result of the linker compound 9 (MW=10000). $^1$H NMR (CDCl$_3$, 400 MHz) δ 9.78 (s, 1H), 5.23 (br s, 1H), 4.13 (d, 2H), 3.81-3.41 (m, 914H), 3.36 (m, 2H), 2.67 (t, 2H), 2.26-2.18 (m, 6H), 1.57 (m, 2H), 1.35 (m, 1H), 0.93 (m, 2H).

EXAMPLE 6

Preparation of Linker Compound (6)

6-1: Preparation of Compound 2 (MW=5000)

A compound 2 (MW=5000) was obtained in the same manner as in Example 2-1.

6-2: Preparation of Compound 3 (MW=5000)

A compound 3 (MW=5000) was obtained in the same manner as in Example 2-2.

6-3: Preparation of Compound 8 (MW=5000)

3 g of the compound 3 (MW=5000) and 30 mL of dichloromethane were introduced into a reactor. 524 mg of the compound 7 and 182 mg of triethylamine were added, followed by stirring at room temperature for 3 hours. After completing the reaction, the solvent was distilled under reduced pressure and 30 mL of water was introduced to dissolve the product. Ethyl acetate (30 mL×3) was introduced and stirred for 5 minutes, and then an aqueous layer was separated and extracted twice using 30 mL of dichloromethane. The obtained organic layer was dried over magnesium sulfate. Filtration was performed, followed by distillation under reduced pressure. 3 mL of dichloromethane was added to the concentrate, which was then dissolved, and 45 mL of methyl t-butyl ether was added dropwise for 20 minutes. Resulting crystals were filtered and washed with methyl t-butyl ether, and then dried under nitrogen to obtain 2.0 g of a compound (8) (MW=5000) which is a title compound.

6-4: Preparation of Compound 9 (MW=5000)

1.7 g of the compound 5 (MW=5000) and 30.6 mL of distilled water were introduced into a reactor. 3.4 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 34 mL of dichloromethane. The resultant was dried over magnesium sulfate, and filtered and distilled under reduced pressure. 2 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 1.25 g of a compound (9) (MW=5000) which is a title compound. The compound 9 (MW=5000) was designated as ALD-PEG 5K-BCN. $^1$H NMR (CDCl$_3$, 400 MHz) δ 9.78 (s, 1H), 5.26 (br s, 1H), 4.15 (d, 2H), 3.81-3.41 (m, 458H), 3.36 (m, 2H), 2.68 (t, 2H), 2.26-2.18 (m, 6H), 1.57 (m, 2H), 1.37 (m, 1 H), 0.93 (m, 2H).

EXAMPLE 7

Preparation of Linker Compound (7)

7-1: Preparation of Compound 2 (MW=3400)

A compound 2 (MW=3400) was obtained in the same manner as in Example 3-1.

7-2: Preparation of Compound 3 (MW=3400)

A compound 3 (MW=3400) was obtained in the same manner as in Example 3-2.

7-3: Preparation of Compound 8 (MW=3400)

2.5 g of the compound 3 (MW=3400) and 50 mL of dichloromethane were introduced into a reactor. 643 mg of the compound 7 and 223 mg of triethylamine were added, followed by stirring at room temperature for 3 hours. After completing the reaction, the solvent was distilled under reduced pressure and 50 mL of water was introduced to dissolve the product. Ethyl acetate (50 mL×3) was introduced and stirred for 5 minutes, and then an aqueous layer was separated and extracted twice using 50 mL of dichloromethane. The obtained organic layer was dried over magnesium sulfate. Filtration was performed, followed by distillation under reduced pressure. 5 mL of dichloromethane was added to the concentrate, which was then dissolved, and 50 mL of methyl t-butyl ether was added dropwise for 20 minutes. Resulting crystals were filtered and washed with methyl t-butyl ether, and then dried under nitrogen to obtain 1.4 g of a compound (8) (MW=3400) which is a title compound.

7-4: Preparation of Compound 9 (MW=3400)

1 g of the compound 5 (MW=3400) and 18 mL of distilled water were introduced into a reactor. 2 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 20 mL of dichloromethane. The resultant was dried over magnesium sulfate, and filtered and distilled under reduced pressure. 2 mL of dichloromethane was added to the concentrate, which was then dissolved, and 20 mL of methyl t-butyl ether was added dropwise for 20 minutes. Resulting crystals were filtered and washed with methyl t-butyl ether, and then dried under nitrogen to obtain 630 mg of a compound (9) (MW=3400) which is a title compound. The compound 9 (MW=3400) was designated as ALD-PEG 3.4K-BCN. $^1$H NMR (CDCl$_3$, 400 MHz) δ 9.78 (s, 1 H), 5.26 (br s, 1H), 4.15 (d, 2H), 3.81-3.41 (m, 314H), 3.36 (m, 2H), 2.68 (t, 2H), 2.26-2.18 (m, 6H), 1.57 (m, 2H), 1.37 (m, 1 H), 0.93 (m, 2H).

EXAMPLE 8

Preparation of Linker Compound (8)

8-1: Preparation of Compound 2 (MW=2000)

A compound 2 (MW=2000) was obtained in the same manner as in Example 4-1.

8-2: Preparation of Compound 3 (MW=2000)

A compound 3 (MW=2000) was obtained in the same manner as in Example 4-2.

8-3: Preparation of Compound 8 (MW=2000)

1.5 g of the compound 3 (MW=2000) and 30 mL of dichloromethane were introduced into a reactor. 655 mg of the compound 7 and 230 mg of triethylamine were added, followed by stirring at room temperature for 3 hours. After completing the reaction, the solvent was distilled under reduced pressure and 30 mL of water was introduced to dissolve the product. Ethyl acetate (30 mL×3) was introduced and stirred for 5 minutes, and then an aqueous layer was separated and extracted twice using 30 mL of dichloromethane. The obtained organic layer was dried over magnesium sulfate. Filtration was performed, followed by distillation under reduced pressure. 3 mL of dichloromethane was added to the concentrate, which was then dissolved, and 90 mL of methyl t-butyl ether was added dropwise for 20 minutes. Resulting crystals were filtered and washed with methyl t-butyl ether, and then dried under nitrogen to obtain 900 mg of a compound (8) (MW=2000) which is a title compound.

8-4: Preparation of Compound 9 (MW=2000)

0.8 g of the compound 5 (MW=2000) and 14.4 mL of distilled water were introduced into a reactor. 1.6 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 20 mL of dichloromethane. The resultant was dried over magnesium sulfate, and filtered and distilled under reduced pressure. 2 mL of dichloromethane was added to the concentrate, which was then dissolved, and 60 mL of methyl t-butyl ether was added dropwise for 20 minutes. Resulting crystals were filtered and washed with methyl t-butyl ether, and then dried under nitrogen to obtain 549 mg of a compound (9) (MW=2000) which is a title compound. The compound 9 (MW=2000) was designated as ALD-PEG 2K-BCN. $^1$H NMR (CDCl$_3$, 400 MHz) δ 9.78 (s, 1H), 5.26 (br s, 1H), 4.15 (d, 2H), 3.81-3.41 (m, 186H), 3.36 (m, 2H), 2.68 (t, 2H), 2.26-2.18 (m, 6H), 1.57 (m, 2H), 1.37 (m, 1 H), 0.93 (m, 2H).

EXAMPLE 9

Preparation of Linker Compound (9)

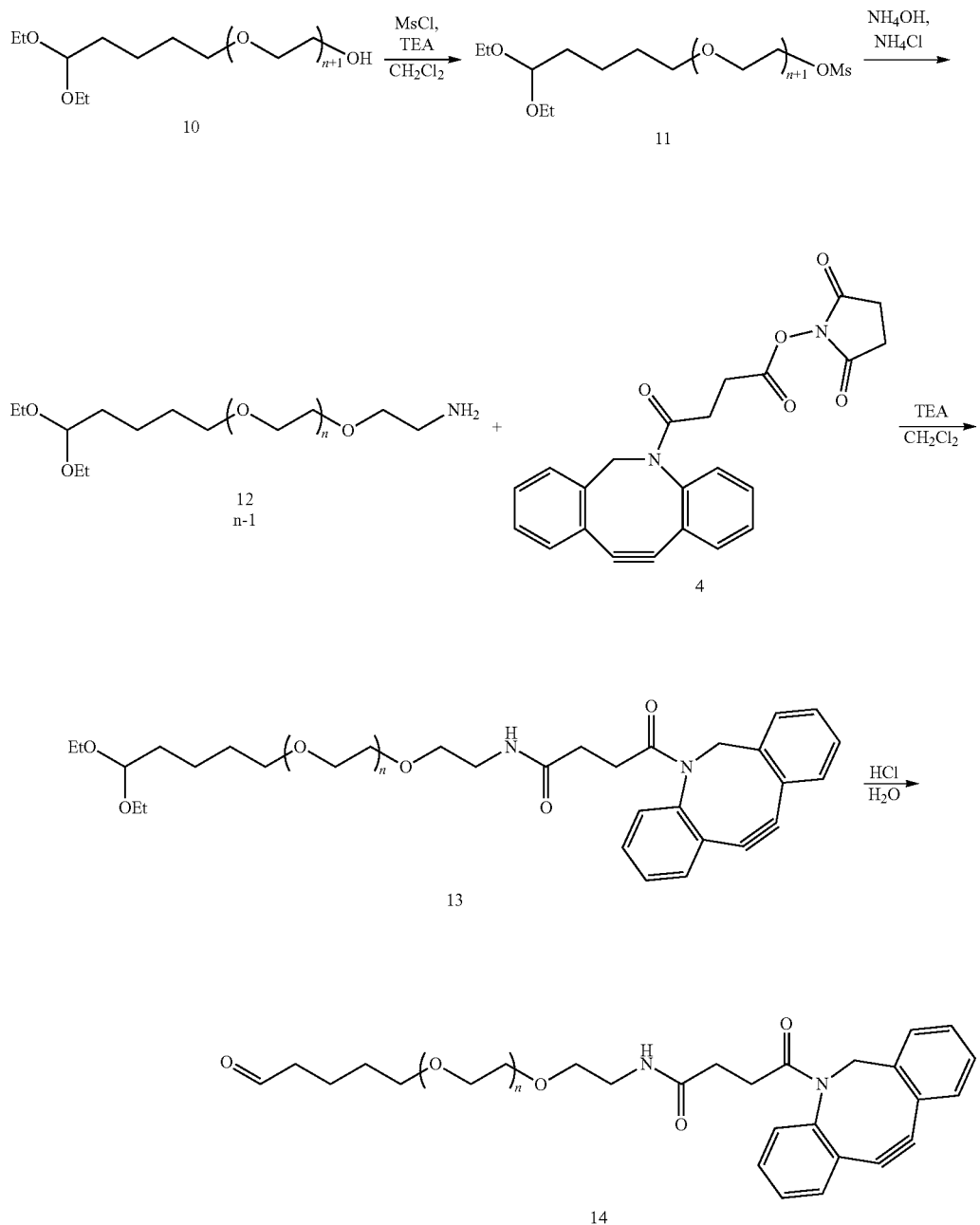

9-1: Preparation of Compound 11 (MW=10000)

27.7 g of the compound 10 (MW=10000) and 83 mL of dichloromethane were introduced into a reactor. 1.54 g of triethylamine and 1.59 g of methanesulfonyl chloride were added thereto while maintaining a reaction temperature at 10° C. or less, followed by stirring at room temperature for 3 hours. After completing the reaction, 140 mL of water and 57 mL of dichloromethane were introduced, followed by stirring for 5 minutes. The obtained organic layer was separated, and then 140 mL of dichloromethane was added to an aqueous layer for further extraction. The organic layer was collected and washed with 140 mL of water, and dried over magnesium sulfate. Filtration was performed, and a remaining filtrate was distilled under reduced pressure. 30 mL of dichloromethane was added to the concentrate, which was then dissolved, and 450 mL of methyl t-butyl ether was added dropwise for 20 minutes. Resulting crystals were filtered and washed with methyl t-butyl ether, and then dried at room temperature under nitrogen to obtain 25.5 g of a compound (11) (MW=10000) which is a title compound.

9-2: Preparation of Compound 12 (MW=10000)

200 mL of an ammonia aqueous solution and 20 g of ammonium chloride were introduced into a reactor. 10 g of compound 11 (MW=10000) was added, followed by stirring at room temperature for 4 days. After completing the reaction, 200 mL of dichloromethane was introduced, followed by stirring for 5 minutes. The obtained organic layer was separated, and then 200 mL of dichloromethane was added to an aqueous layer for further extraction. The organic layer was collected and washed with 200 mL of distilled water, and dried over magnesium sulfate. Filtration was performed, and a remaining filtrate was distilled under reduced pressure. 10 mL of dichloromethane was added to the concentrate, which was then dissolved, and 150 mL of methyl t-butyl ether was added dropwise for 20 minutes. Resulting crystals were filtered and washed with methyl t-butyl ether, and then dried at room temperature under nitrogen to obtain 8.1 g of a compound (12) (MW=10000) which is a title compound.

9-3: Preparation of Compound 13 (MW=10000)

3 g of the compound 12 (MW=10000) and 30 mL of dichloromethane were introduced into a reactor. 362 mg of the compound 4 and 91 mg of triethylamine were added, followed by stirring at room temperature for 3 hours. After completing the reaction, the solvent was distilled under reduced pressure and 30 mL of water was introduced to dissolve the product. Ethyl acetate (30 mL×3) was introduced and stirred for 5 minutes, and then an aqueous layer was separated and extracted twice using 30 mL of dichloromethane. The obtained organic layer was dried over magnesium sulfate. Filtration was performed, followed by distillation under reduced pressure. 3 mL of dichloromethane was added to the concentrate, which was then dissolved, and 45 mL of methyl t-butyl ether was added dropwise for 20 minutes. Resulting crystals were filtered and washed with methyl t-butyl ether, and then dried under nitrogen to obtain 1.7 g of a compound (13) (MW=10000) which is a title compound.

9-4: Preparation of Compound 14 (MW=10000)

Figure 6:
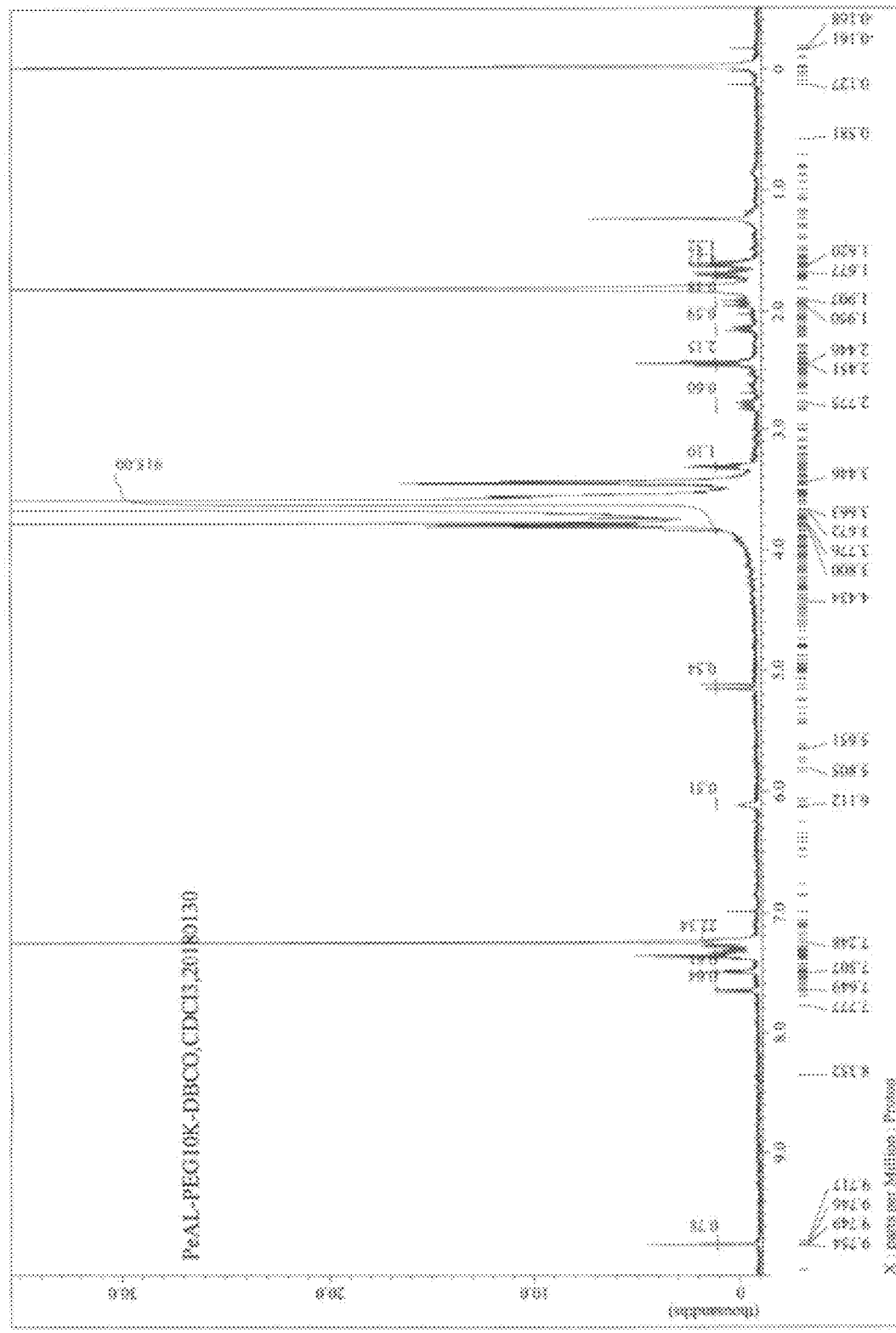
FIG. 6 shows $^1$H NMR result of a linker compound 14 (MW=10000) according to an embodiment.

1.6 g of the compound 5 (MW=10000) and 28.8 mL of distilled water were introduced into a reactor. 3.2 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 32 mL of dichloromethane. The resultant was dried over magnesium sulfate, and filtered and distilled under reduced pressure. 2 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 1.2 g of a compound (14) (MW=10000) which is a title compound. The compound 14 (MW=10000) was designated as PeAL-PEG 10K-DBCO. FIG. 6 shows $^1$H NMR result of the linker compound 14 (MW=10000). $^1$H NMR (CDCl$_3$, 400 MHz) δ 9.75 (s, 1H), 7.65 (d, 1H), 7.51 (d, 1 H), 7.37-7.19 (m, 6H), 6.11 (br s, 1 H), 5.12 (d, 1 H), 3.85-3.42 (m, 915H), 3.32 (m, 2H), 2.80 (m, 1H), 2.47-2.41 (m, 3H), 2.16 (m, 1H), 1.92 (m, 1H), 1.70 (m, 2H), 1.61 (m, 2H).

EXAMPLE 10

Preparation of Linker Compound (10)

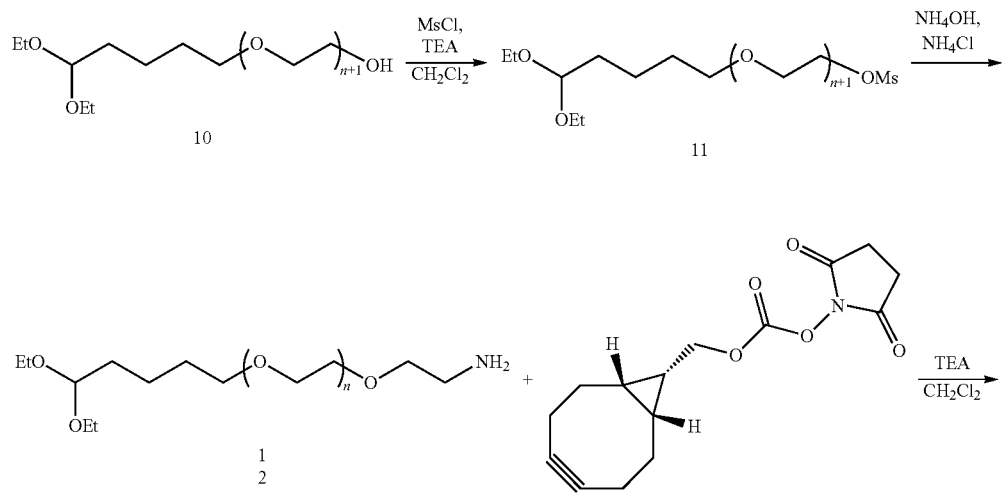

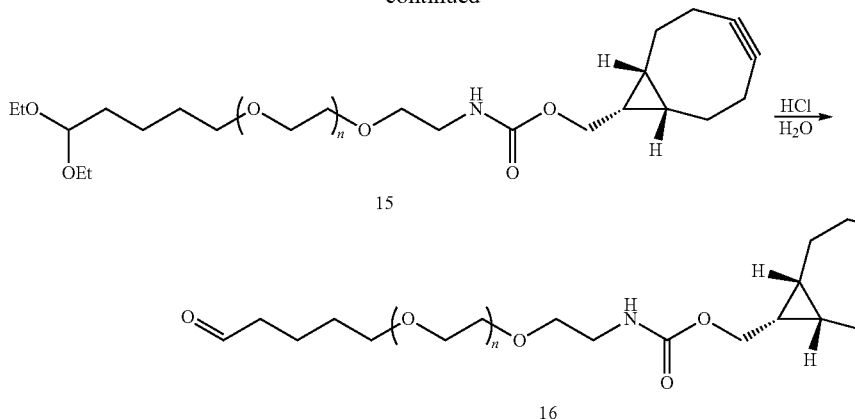

10-1: Preparation of Compound 11 (MW=10000)

A compound 11 (MW=10000) was obtained in the same manner as in Example 9-1.

10-2: Preparation of Compound 12 (MW=10000)

A compound 12 (MW=10000) was obtained in the same manner as in Example 9-2.

10-3: Preparation of Compound 15 (MW=10000)

3 g of the compound 12 (MW=10000) and 30 mL of dichloromethane were introduced into a reactor. 262 mg of the compound 7 and 91 mg of triethylamine were added, followed by stirring at room temperature for 3 hours. After completing the reaction, the solvent was distilled under reduced pressure and 30 mL of water was introduced to dissolve the product. Ethyl acetate (30 mL×3) was introduced and stirred for 5 minutes, and then an aqueous layer was separated and extracted twice using 30 mL of dichloromethane. The obtained organic layer was dried over magnesium sulfate. Filtration was performed, followed by distillation under reduced pressure. 3 mL of dichloromethane was added to the concentrate, which was then dissolved, and 45 mL of methyl t-butyl ether was added dropwise for 20 minutes. Resulting crystals were filtered and washed with methyl t-butyl ether, and then dried under nitrogen to obtain 1.6 g of a compound (15) (MW=10000) which is a title compound.

10-4: Preparation of Compound 16 (MW=10000)

Figure 7:
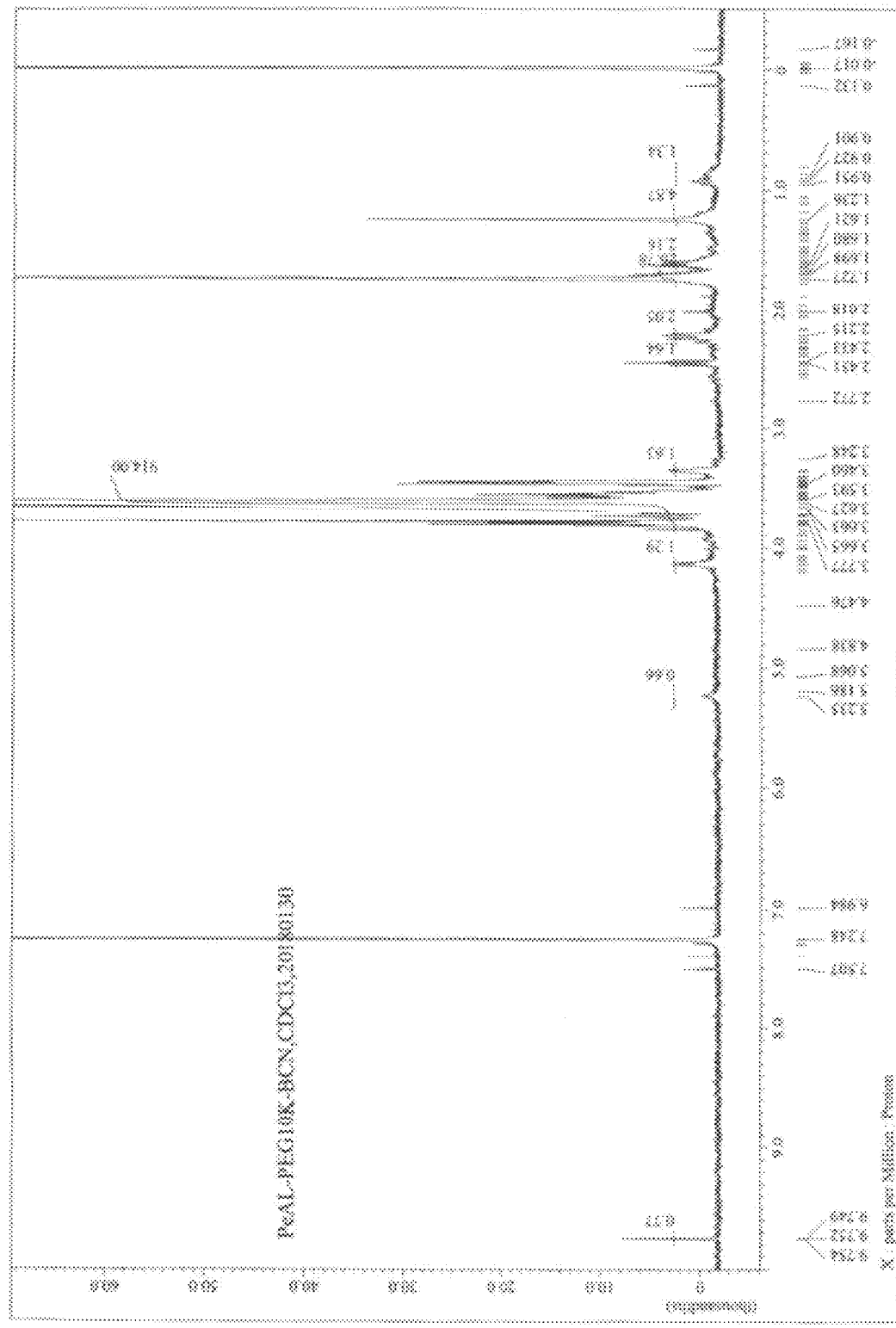
FIG. 7 shows $^1$H NMR result of a linker compound 16 (MW=10000) according to an embodiment.

1.5 g of the compound 5 (MW=10000) and 27 mL of distilled water were introduced into a reactor. 3 mL of 0.1 N HCl was added thereto and stirred at room temperature for 2 hours. Then, completion of the reaction was confirmed by NMR. The reaction solution was neutralized with a 5% (w/v) sodium bicarbonate aqueous solution, and extraction was performed twice using 30 mL of dichloromethane. The resultant was dried over magnesium sulfate, and filtered and distilled under reduced pressure. 2 mL of dichloromethane was added to the concentrate, which was then dissolved, and 30 mL of methyl t-butyl ether was added dropwise for 20 minutes. Resulting crystals were filtered and washed with methyl t-butyl ether, and then dried under nitrogen to obtain 1.1 g of a compound (16) (MW=10000) which is a title compound. The compound 16 (MW=10000) was designated as PeAL-PEG 10K-BCN. FIG. 7 shows $^1$H NMR result of the linker compound 16 (MW=10000). $^1$H NMR (CDCl$_3$, 400 MHz) δ 9.75 (s, 1 H), 5.20 (br s, 1 H), 4.12 (d, 2H), 3.85-3.44 (m, 914H), 3.36 (m, 2H), 2.45 (t, 2H), 2.28-2.16 (m, 6H), 1.70 (m, 2H), 1.62-1.59 (m, 4H), 1.18 (m, 1H), 0.93 (m, 2H).

EXPERIMENTAL EXAMPLE 1

Mass Spectrometry of Linker Compounds

Mass spectrometry of the linker compounds prepared in Examples was performed using a MALDI-TOF mass spectrometer. Results were analyzed using a Polytool software.

Figure 8:
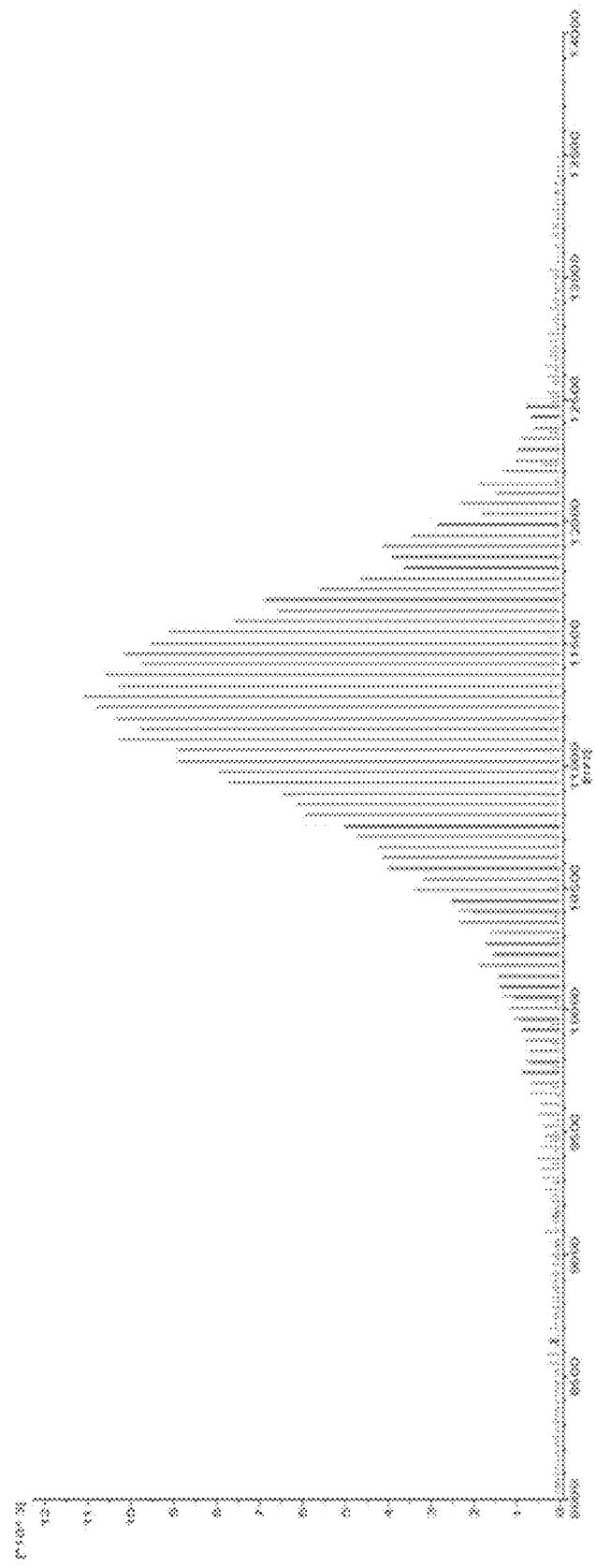
FIG. 8 shows a result of mass spectrometry of a linker compound ALD-PEG 10K-DBCO.

FIG. 8 shows a result of mass spectrometry of the linker compound ALD-PEG 10K-DBCO.

Figure 9:
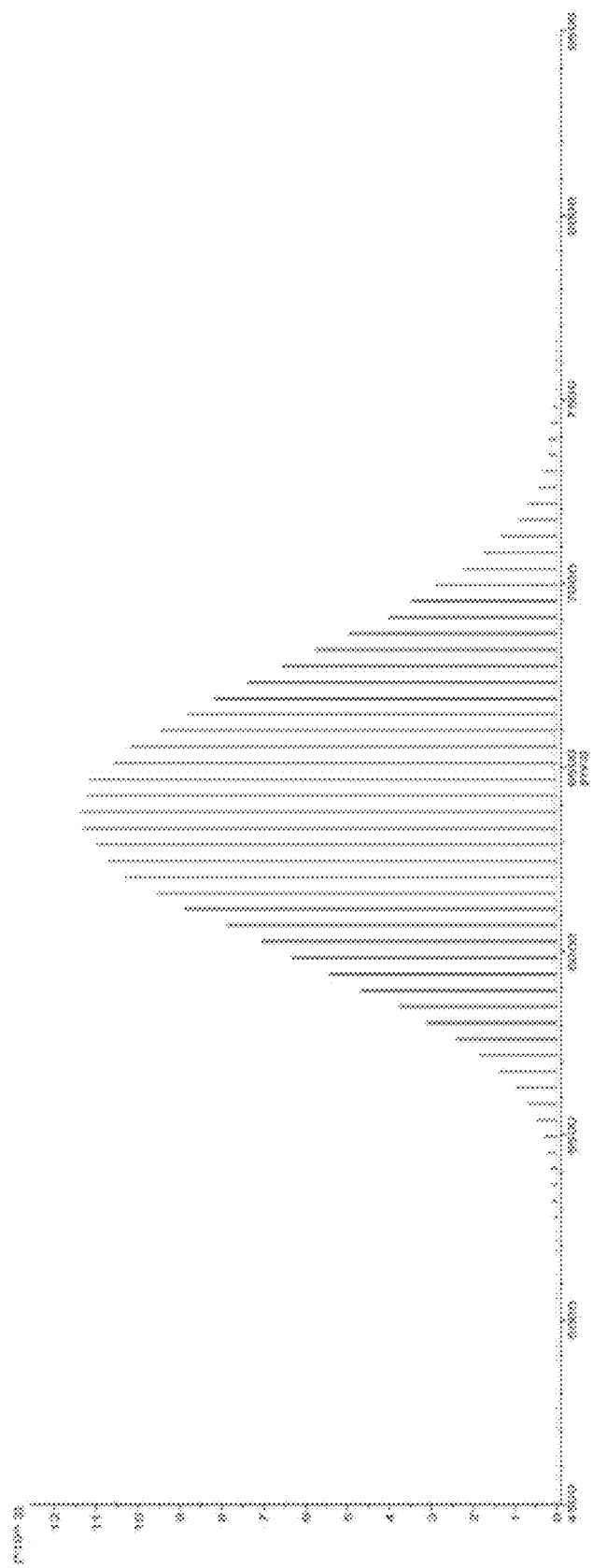
FIG. 9 shows a result of mass spectrometry of a linker compound ALD-PEG 5K-DBCO.

FIG. 9 shows a result of mass spectrometry of the linker compound ALD-PEG 5K-DBCO.

Figure 10:
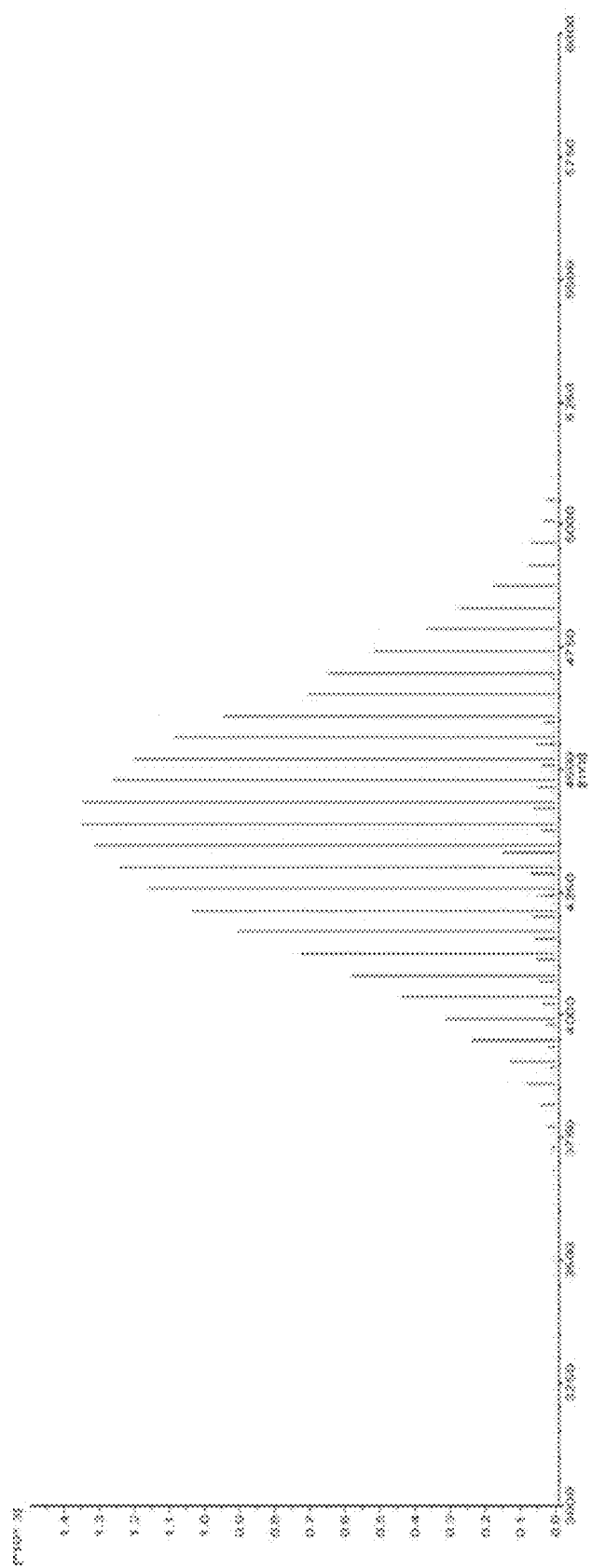
FIG. 10 shows a result of mass spectrometry of a linker compound ALD-PEG 3.4K-DBCO.

FIG. 10 shows a result of mass spectrometry of the linker compound ALD-PEG 3.4K-DBCO.

Figure 11:
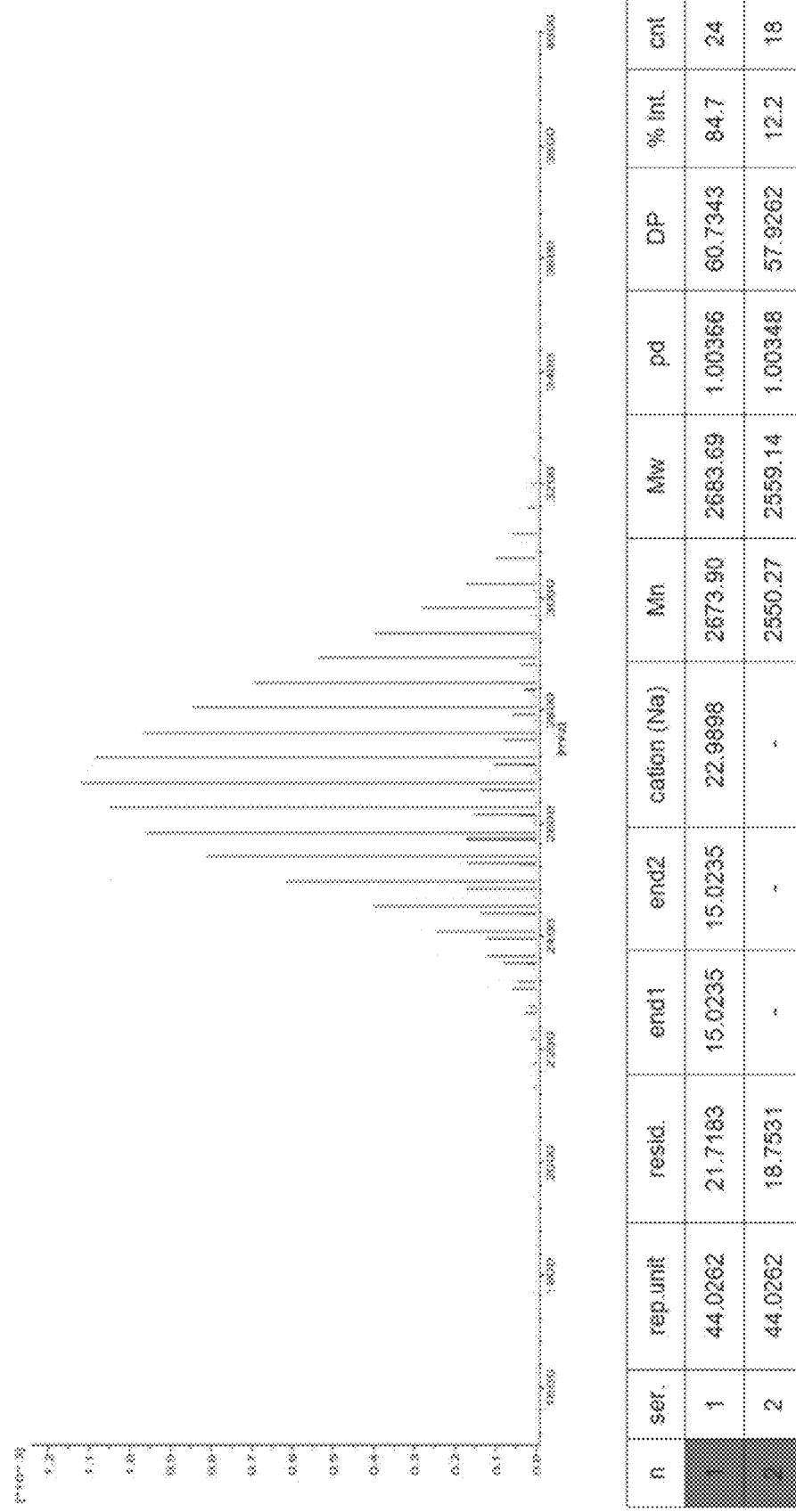
FIG. 11 shows a result of mass spectrometry of a linker compound ALD-PEG 2K-DBCO.

FIG. 11 shows a result of mass spectrometry of the linker compound ALD-PEG 2K-DBCO.

Figure 12:
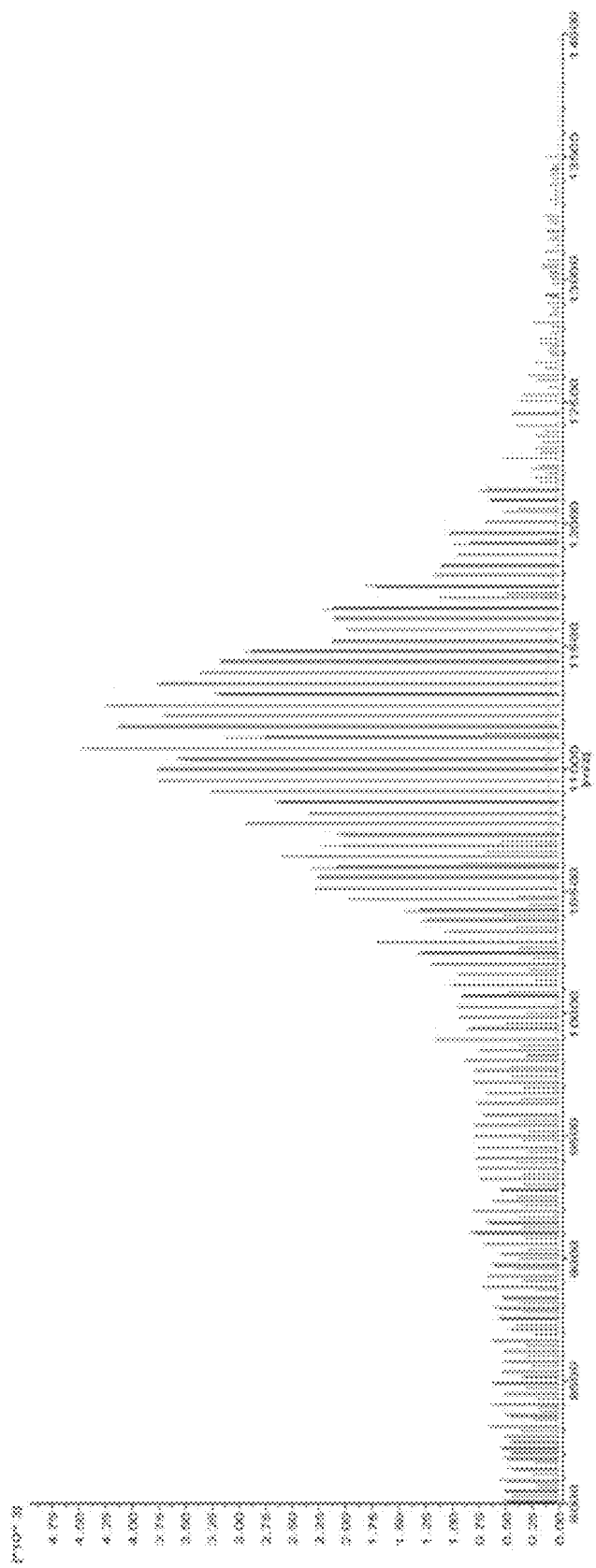
FIG. 12 shows a result of mass spectrometry of a linker compound PeALD-PEG 10K-BCN.

FIG. 12 shows a result of mass spectrometry of the linker compound PeALD-PEG 10K-BCN.

Figure 13:
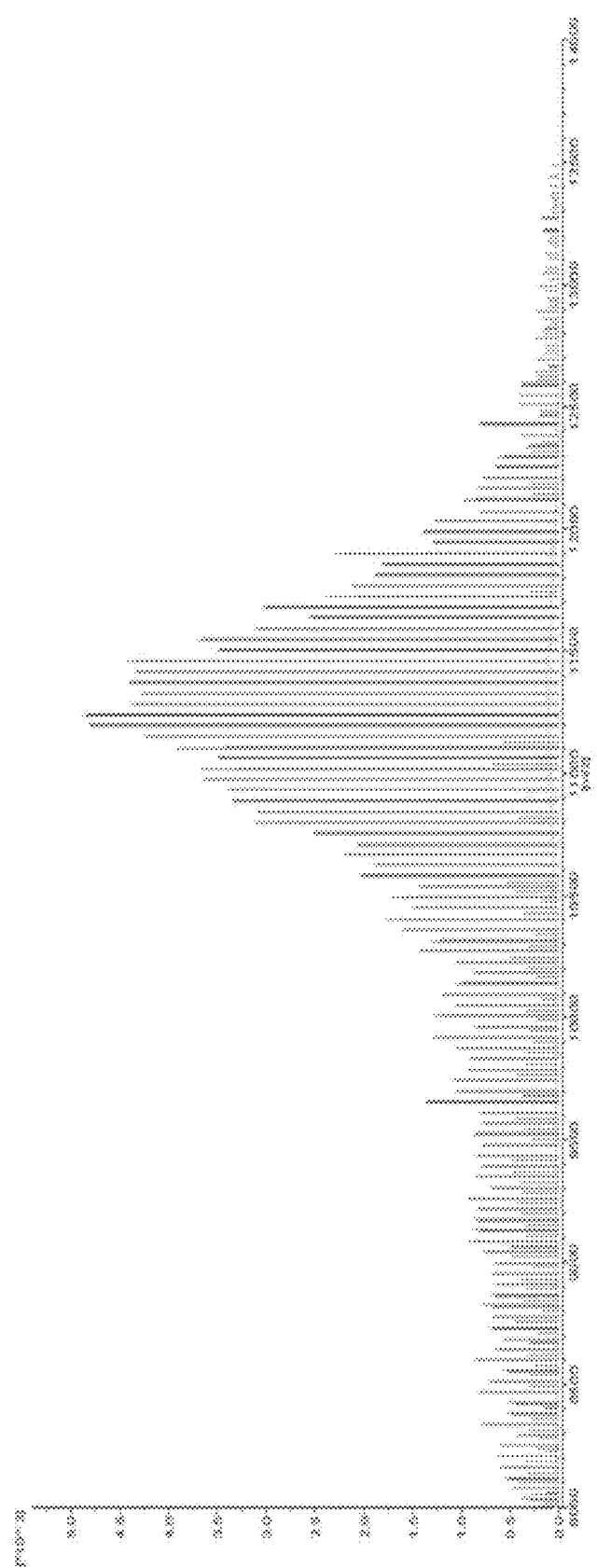
FIG. 13 shows a result of mass spectrometry of a linker compound PeALD-PEG 10K-DBCO.

FIG. 13 shows a result of mass spectrometry of the linker compound PeALD-PEG 10K-DBCO.

Figure 14:
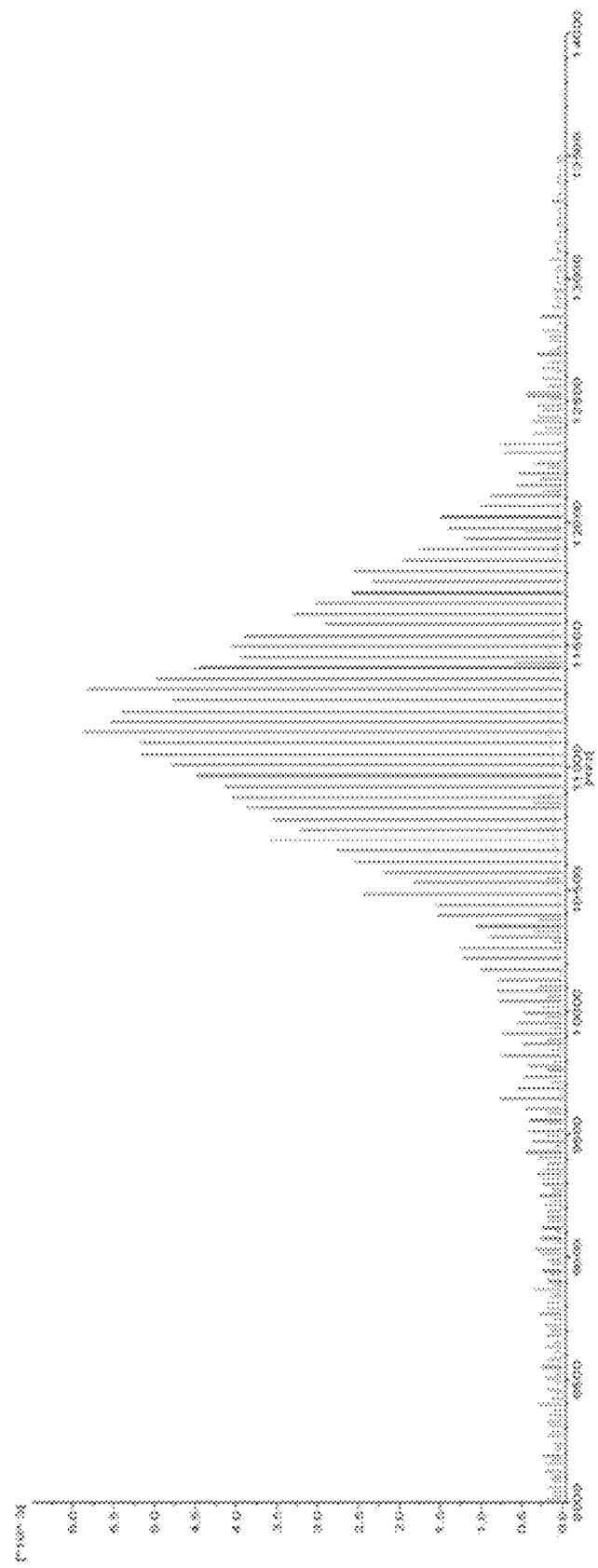
FIG. 14 shows a result of mass spectrometry of a linker compound ALD-PEG 10K-BCN.

FIG. 14 shows a result of mass spectrometry of the linker compound ALD-PEG 10K-BCN.

EXAMPLE 11

Preparation of Physiologically Active Polypeptide Linkage (1)

A physiologically active polypeptide linkage was prepared by linking a physiologically active polypeptide to the ALD-PEG 10K-BCN linker of Example 5.

In detail, the physiologically active polypeptide was a triple agonist having activities to all of glucagon, GLP-1, and GIP receptors, disclosed as SEQ ID NO: 42 in WO 2017/116205 A1. The C-terminal amino acid of the triple agonist was replaced with lysine, to which an azide group was introduced, thereby preparing an azide-introduced triple agonist, which was designated as HMT211-azido.

The prepared HMT211-azido powder was dissolved in 10% (v/v) 10 mM HCl, and then HMT211-azido was prepared at a final concentration of 5 mg/ml such that a molar ratio of the HMT211-azido and the ALD-PEG 10K-BCN linker of Example 5 was 1:5, and allowed to react at 4° C. for about 2 hours. At this time, the reaction was allowed in a mixed solvent of 50 mM sodium citrate buffer (pH 7.5) and 60% (v/v) isopropanol.

The reaction solution was purified using a SP-HP (GE Healthcare) column with a concentration gradient of KCl in a buffer containing sodium citrate (pH 3.0) and 45% (v/v) EtOH. As a result, mono-PEGylated HMT211-azido-PEG was obtained.

EXAMPLE 12

Preparation of Physiologically Active Polypeptide Conjugate (1)

Next, mono-PEGylated HMT211-azido-PEG purified in Example 11 and an immunoglobulin Fc were reacted at a molar ratio of 1:4 at a final concentration of 10 mg/ml at 25° C. for about 15 hours. At this time, to the reaction solution, 10 mM potassium phosphate (pH 6.0) and 20 mM sodium cyanoborohydride as a reducing agent were added.

After completing the reaction, the reaction solution was applied to a S.15Q (GE, USA) column using a concentration gradient of NaCl in Tris-HCl (pH 7.5) buffer, thereby purifying a HMT211-azido-PEG-immunoglobulin Fc conjugate.

Purity of the eluted HMT211-azido-PEG-immunoglobulin Fc conjugate was analyzed by SDS-PAGE.

Figure 15:
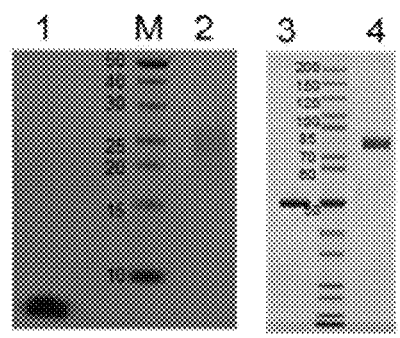
FIG. 15 shows a result of SDS-PAGE purity analysis of an HMT211-azido-PEG-immunoglobulin Fc conjugate, wherein M: Marker, 1: HMT211-azido peptide, 2: mono-PEGylated HMT211-azido-PEG, 3: immunoglobulin Fc, 4: HMT211-azido-PEG-immunoglobulin FC conjugate prepared by linking HMT211-azido with an immunoglobulin Fc via the ALD-PEG 10K-BCN linker.

FIG. 15 shows a result of SDS-PAGE purity analysis of the HMT211-azido-PEG-immunoglobulin Fc conjugate. M: Marker, 1: HMT211-azido peptide, 2: mono-PEGylated HMT211-azido-PEG, 3: immunoglobulin Fc, 4: HMT211-azido-PEG-immunoglobulin FC conjugate prepared by linking HMT211-azido with an immunoglobulin Fc via the ALD-PEG 10K-BCN linker.

As shown in FIG. 15, it was confirmed that when the linker compound according to Example 5 is used, the physiologically active polypeptide conjugate, of which both ends are linked with the physiologically active polypeptide and the immunoglobulin Fc, may be obtained in a high yield.

EXAMPLE 13

Preparation of Physiologically Active Polypeptide Linkage (2)

A physiologically active polypeptide linkage was prepared by linking a physiologically active polypeptide to the ALD-PEG 10K-DBCO linker of Example 1.

In detail, the physiologically active polypeptide was GLP-2 derivative-azido, in which azido-lysine was introduced to the C-terminus of GLP-2. For example, GLP-2 derivative-azido in this Example was prepared by introducing azido-lysine to the C-terminus of natural GLP-2, substituting glycine for alanine which is the second amino acid, and removing alpha carbon of a histidine residue which is the first amino acid from the N-terminus.

To PEGylate the ALD-PEG 10K-DBCO (10 kDa) of Example 1 to the GLP-2 derivative-azido, GLP-2 derivative-azido was prepared at a concentration of 5 mg/ml such that a molar ratio of GLP-2 derivative-azido powder:ALD-PEG 10K-DBCO was 1:5, and allowed to react at 4° C. for about 4 hours. At this time, the reaction was allowed in a mixed solvent of 50 mM sodium phosphate buffer (pH 7.5) and 60% (v/v) isopropanol.

Figure 16:
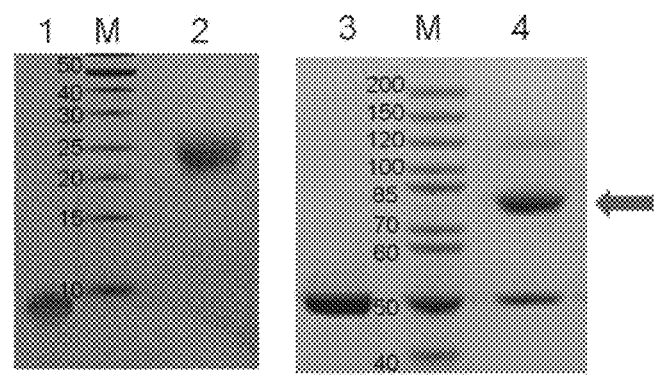
FIG. 16 shows a result of non-reducing SDS-PAGE purity analysis of a GLP-2 analog-azido-PEG-immunoglobulin Fc conjugate, wherein M: Marker, 1: GLP-2 analog, 2: mono-PEGylated GLP-2 analog, 3: immunoglobulin Fc, 4: GLP-2 analog-PEG-immunoglobulin Fc conjugate prepared by linking GLP-2 analog-azido with an immunoglobulin Fc via the ALD-PEG 10K-DBCO linker.

The reaction solution was purified by applying it to a Q Sepharose High Performance (GE Healthcare, USA) column using a concentration gradient of sodium chloride in Bis-Tris (pH 6.2). As a result, SDS-PAGE analysis confirmed that mono-PEGylated GLP-2 derivative-azido-PEG was purified (FIG. 16).

EXAMPLE 14

Preparation of Physiologically Active Polypeptide Conjugate (2)

Next, mono-PEGylated GLP-2 analog-azido-PEG purified in Example 13 and an immunoglobulin Fc were reacted at a molar ratio of 1:4 at a final concentration of 10 mg/ml at 2° C. to 8° C. for about 12 hours to 18 hours. At this time, to the reaction solution, 10 mM potassium phosphate and 20% (v/v) isopropanol (pH 6.0), 20 mM sodium cyanoborohydride as a reducing agent were added, and under this environment, the reaction was allowed.

After completing the reaction, the reaction solution was applied to a Butyl Sepharose 4 Fast Flow (GE Healthcare, USA) column using a concentration gradient of sodium chloride in Tris (pH 7.5) and isopropanol buffer, thereby purifying a GLP-2 analog-azido-PEG-immunoglobulin Fc conjugate.

Purity of the eluted GLP-2 analog-azido-PEG-immunoglobulin Fc conjugate was analyzed by SDS-PAGE.

FIG. 16 shows a result of non-reducing SDS-PAGE purity analysis of the GLP-2 analog-azido-PEG-immunoglobulin Fc conjugate. M: Marker, 1: GLP-2 analog, 2: mono-PEGylated GLP-2 analog, 3: immunoglobulin Fc, 4: GLP-2 analog-PEG-immunoglobulin Fc conjugate prepared by linking GLP-2 analog-azido with the immunoglobulin Fc via the ALD-PEG 10K-DBCO linker.

As shown in FIG. 16, it was confirmed that when the linker compound according to Example 1 is used, the physiologically active polypeptide conjugate, of which both ends are linked with the physiologically active polypeptide and the immunoglobulin Fc, may be obtained in a high yield.

EXAMPLE 15

Preparation of Physiologically Active Polypeptide Linkage (3)

A physiologically active polypeptide linkage was prepared by linking a physiologically active polypeptide to the PeAL-PEG 10K-BCN linker of Example 10.

In detail, the physiologically active polypeptide was a glucagon analog, disclosed as SEQ ID NO: 37 in WO 2017/003191 A1. The C-terminal amino acid of the glucagon analog was replaced with lysine, to which an azide group was introduced, thereby preparing an azide-introduced glucagon analog, which was designated as glucagon analog-azido.

To PEGylate the PeAL-PEG 10K-BCN (10 kDa) of Example 10 to the glucagon analog-azido, glucagon analog-azido was prepared at a concentration of 5 mg/ml such that a molar ratio of glucagon analog-azido:PeAL-PEG 10K-BCN was 1:5, and allowed to react at 4° C. for about 4 hours. At this time, the reaction was allowed in a mixed solvent of 50 mM sodium phosphate buffer (pH 7.5), 60% (v/v) isopropanol, and 20% (v/v) DMSO.

Figure 17:
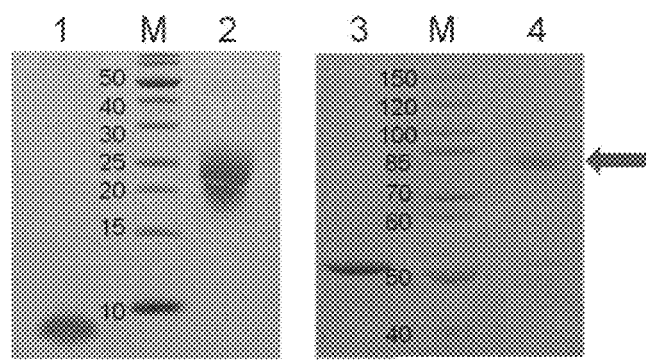
FIG. 17 shows a result of non-reducing SDS-PAGE purity analysis of a glucagon analog-azido-PEG-immunoglobulin Fc conjugate, wherein M: Marker, 1: glucagon analog, 2: mono-PEGylated glucagon analog, 3: immunoglobulin Fc, 4: glucagon analog-PEG-immunoglobulin Fc conjugate prepared by linking glucagon analog-azido with an immunoglobulin Fc via a PeAL-PEG 10K-BCN linker.

The reaction solution was purified by applying it to a SP Sepharose High Performance (GE Healthcare, USA) column using a concentration gradient of potassium chloride in sodium citrate (pH 3.0) and 45% (v/v) ethanol. As a result, SDS-PAGE analysis confirmed that mono-PEGylated glucagon analog-azido-PEG was purified (FIG. 17).

EXAMPLE 16

Preparation of Physiologically Active Polypeptide Conjugate (3)

Next, mono-PEGylated glucagon analog-azido-PEG purified in Example 15 and an immunoglobulin Fc were reacted at a molar ratio of 1:4 at a final concentration of 10 mg/ml at 2° C. to 8° C. for about 12 hours to 18 hours. At this time, to the reaction solution, 100 mM potassium phosphate and 20% (v/v) isopropanol (pH 6.0), 20 mM sodium cyanoborohydride (NaCNBH$_3$) as a reducing agent were added, and under this environment, the reaction was allowed.

After completing the reaction, the reaction solution was applied to a Source 15Q (GE Healthcare, USA) column using a concentration gradient of sodium chloride in Tris (pH 7.5), thereby purifying a glucagon analog-azido-PEG-immunoglobulin Fc conjugate.

Purity of the eluted glucagon analog-azido-PEG-immunoglobulin Fc conjugate was analyzed by SDS-PAGE.

FIG. 17 shows a result of non-reducing SDS-PAGE purity analysis of the glucagon analog-azido-PEG-immunoglobulin Fc conjugate. M: Marker, 1: glucagon analog, 2: mono-PEGylated glucagon analog, 3: immunoglobulin Fc, 4: glucagon analog-PEG-immunoglobulin Fc conjugate prepared by linking glucagon analog-azido with the immunoglobulin Fc via the PeAL-PEG 10K-BCN linker.

As shown in FIG. 17, it was confirmed that when the linker compound according to Example 10 is used, the physiologically active polypeptide conjugate, of which both ends are linked with the physiologically active polypeptide and the immunoglobulin Fc, may be obtained in a high yield.

The present disclosure has been shown and described with reference to exemplary embodiments. It will be understood by those skilled in the art that various modifications may be made without departing from the fundamental characteristics of the present disclosure. Therefore, it should be understood that embodiments described herein should be considered in a descriptive sense only and not for purposes of limitation. The scope of the present disclosure is defined by the appended claims rather than by the foregoing description, and all differences within the scope of equivalents thereof should be construed as being included in the present disclosure.

The invention claimed is:

1. A compound selected from a compound of the following Formula 1a, a stereoisomer thereof, a solvate thereof, and a pharmaceutically acceptable salt thereof:

[Formula 1a]
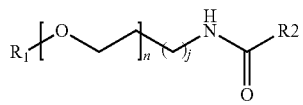

in Formula 1a,
n is an integer of 20 to 1000;
j is an integer of 0 to 6;
R1 is an aliphatic hydrocarbon group comprising an aldehyde group;
R2 is —(R3)$_k$-(Z)$_l$—(R4)$_m$-(CZ)$_p$—Y,
wherein R3 and R4 are each independently C$_1$-C$_6$ alkylene, C$_6$-C$_{20}$ arylene, or C$_5$-C$_{20}$ heteroarylene having 1 to 3 heteroatoms selected from N, O, and S, Z is O or S, Y is selected from the group consisting of bicyclo[6.1.0]nonyne (BCN), dibenzocyclooctyne (DBCO), difluorinated cyclooctyne (DIFO), DIFO2, DIFO3, dibenzo-annulated cyclooctyne (DIBO), biarylazacyclooctynone (BARAC), cyclooctyne (OCT), aryl-less cyclooctyne (ALO), monofluorinated cyclooctyne (MOFO), dimethoxyazacyclooctyne (DIMAC), 2,3,6,7-tetramethoxy-DIBO (TMDIBO), carboxymethylmonobenzocyclooctyne (COMBO), pyrrolocyclooctyne (PYRROC), dibenzo-aza-cyclooctyne (DIBAC), 3,3,6,6-tetramethylthiacycloheptyne (TMTH), Sondheimer diyne, and sulfonylated DIBO (S-DIBO), and k, l, m, and p are each independently an integer of 0 to 3, provided that all of them are not 0 at the same time.

2. The compound of claim 1, wherein Formula 1a is any one of the following Formulae 2a to 2n:

[Formula 2a]
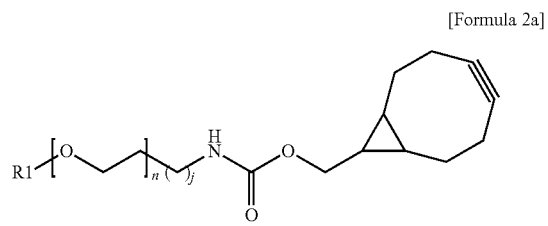

[Formula 2b]
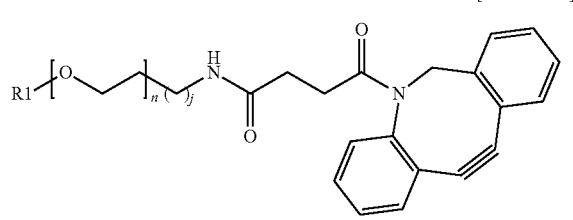

[Formula 2c]
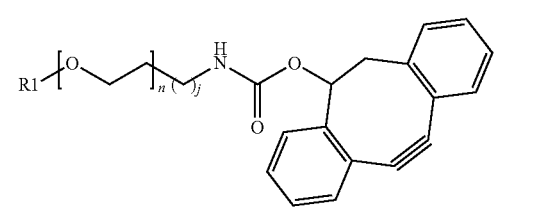

[Formula 2d]
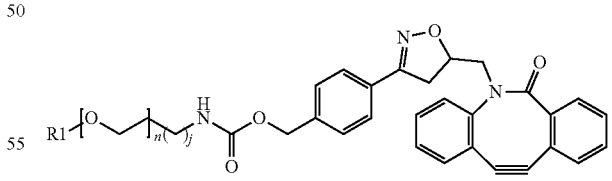

[Formula 2e]
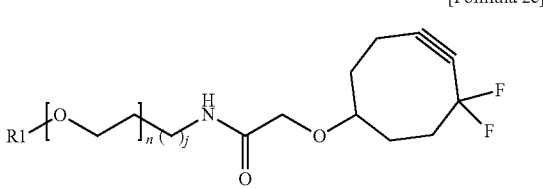

[Formula 2f]
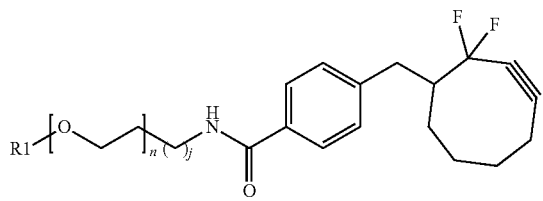

[Formula 2g]
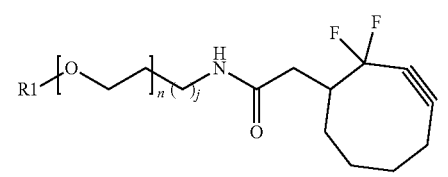

[Formula 2h]
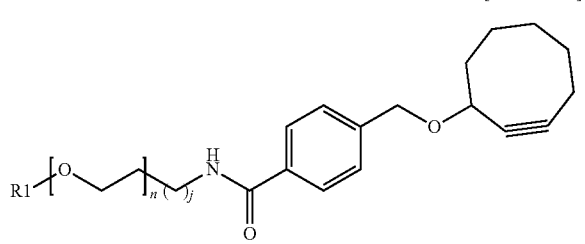

[Formula 2i]
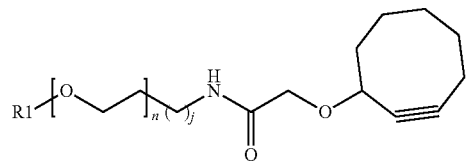

[Formula 2j]
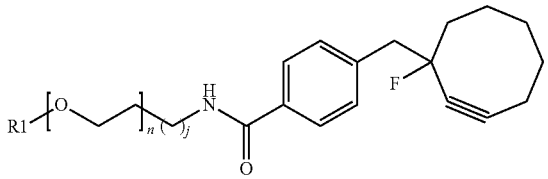

[Formula 2k]
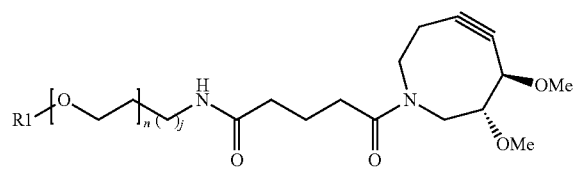

[Formula 2l]
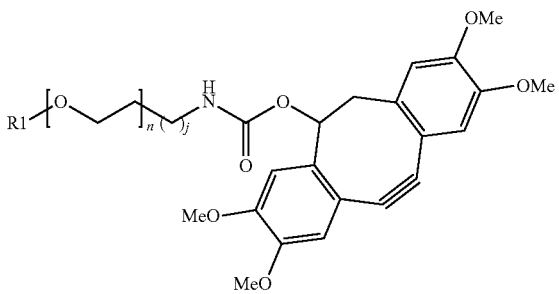

[Formula 2m]
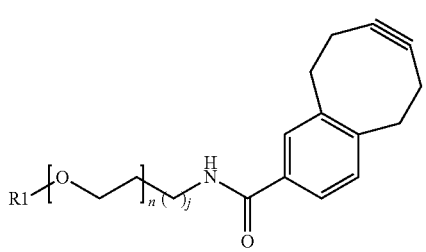

[Formula 2n]
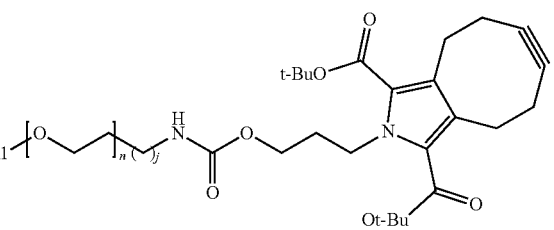

in Formulae 2a to 2n,
n is an integer of 20 to 1000;
j is an integer of 0 to 6; and
R1 is a $C_1$-$C_6$ aliphatic hydrocarbon group comprising an aldehyde group.

3. A method of preparing the compound of claim 1, the method comprising:
introducing an amino group (—NH$_2$) at one end of the polyethylene glycol, and introducing R2 at one end of the polyethylene glycol by an amide bond with the amino group, wherein R2 is the same as defined in claim; and
introducing an aliphatic hydrocarbon group comprising an aldehyde group at the other end of the polyethylene glycol to which R2 is introduced.

* * * * *